(12) United States Patent
Tamura et al.

(10) Patent No.: US 10,406,140 B2
(45) Date of Patent: Sep. 10, 2019

(54) 5-SUBSTITUTED BENZIMIDAZOLE AND 5-SUBSTITUTED AZABENZIMIDAZOLE DERIVATIVE BOTH HAVING AMPK ACTIVATION EFFECT

(71) Applicant: Shionogi & Co., Ltd., Osaka-shi, Osaka (JP)

(72) Inventors: Yuusuke Tamura, Osaka (JP); Toshihiro Wada, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/099,574

(22) PCT Filed: May 19, 2017

(86) PCT No.: PCT/JP2017/018761
§ 371 (c)(1),
(2) Date: Nov. 7, 2018

(87) PCT Pub. No.: WO2017/200068
PCT Pub. Date: Nov. 23, 2017

(65) Prior Publication Data
US 2019/0183866 A1    Jun. 20, 2019

(30) Foreign Application Priority Data

May 20, 2016 (JP) ................. 2016-101056

(51) Int. Cl.
*A61K 31/437* (2006.01)
*A61P 3/10* (2006.01)

(52) U.S. Cl.
CPC .............. *A61K 31/437* (2013.01); *A61P 3/10* (2018.01)

(58) Field of Classification Search
CPC ................................ A61K 31/437; A61P 3/10
See application file for complete search history.

(56) References Cited

U.S. PATENT DOCUMENTS

| | | | |
|---|---|---|---|
| 2013/0184240 A1 | 7/2013 | Tonogaki et al. | |
| 2014/0194420 A1 | 7/2014 | Kojima et al. | |
| 2015/0119393 A1* | 4/2015 | Wagner | C07D 493/04 514/234.2 |
| 2015/0203450 A1 | 7/2015 | Tamura et al. | |
| 2016/0039846 A1 | 2/2016 | Langkopf et al. | |
| 2017/0273955 A1 | 9/2017 | Tamura et al. | |
| 2017/0333398 A1 | 11/2017 | Kojima et al. | |

FOREIGN PATENT DOCUMENTS

| | | |
|---|---|---|
| WO | 2009/100130 | 8/2009 |
| WO | 2010/036613 | 4/2010 |
| WO | 2010/047982 | 4/2010 |
| WO | 2010/051176 | 5/2010 |
| WO | 2010/051206 | 5/2010 |
| WO | 2011/106273 | 9/2011 |
| WO | 2012/116145 | 8/2012 |
| WO | 2014/031441 | 2/2014 |
| WO | 2014/031445 | 2/2014 |
| WO | 2014/031465 | 2/2014 |
| WO | 2014/031468 | 2/2014 |
| WO | 2014/031515 | 2/2014 |
| WO | 2014/031517 | 2/2014 |
| WO | 2014/069426 | 5/2014 |
| WO | 2014/139388 | 9/2014 |
| WO | 2014/175330 | 10/2014 |
| WO | 2015/007669 | 1/2015 |
| WO | 2015/063011 | 5/2015 |
| WO | 2016/023789 | 2/2016 |
| WO | 2016/113299 | 7/2016 |
| WO | 2016/113300 | 7/2016 |
| WO | 2017/146186 | 8/2017 |
| WO | 2017/188288 | 11/2017 |

OTHER PUBLICATIONS

International Search Report dated Jul. 4, 2017 in International Application No. PCT/JP2017/018761.
Bei B. Zhang et al., "AMPK: An Emerging Drug Target for Diabetes and the Metabolic Syndrome", Cell Metabolism, vol. 9, Issue 5, pp. 407-416, 2009.
International Preliminary Report on Patentability dated Nov. 29, 2018 in International Application No. PCT/JP2017/018761.

* cited by examiner

*Primary Examiner* — Timothy R Rozof
(74) *Attorney, Agent, or Firm* — Wenderoth, Lind & Ponack, L.L.P.

(57) ABSTRACT

Provided is a compound which is useful as an AMPK activator, represented by formula:

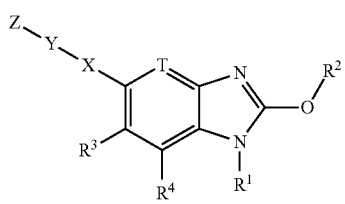

wherein the symbols are defined in the specification.

29 Claims, No Drawings

5-SUBSTITUTED BENZIMIDAZOLE AND 5-SUBSTITUTED AZABENZIMIDAZOLE DERIVATIVE BOTH HAVING AMPK ACTIVATION EFFECT

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in hepatic and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 18 disclose a variety of compounds having an AMPK activating effect. However, a benzimidazole or an azabenzimidazole derivative like the compound of the present invention is not disclosed in any of the documents.

Patent Documents 19 to 21 describe, as a compound having an AMPK activating effect, for example, compounds in which the 5-end of azabenzimidazole as shown below is substituted with a sulfoximine group, a carbamate group or the like, the 2-position is substituted with an isomannide group, and the 6-position is substituted with chloro.

[Chemical formula 1]

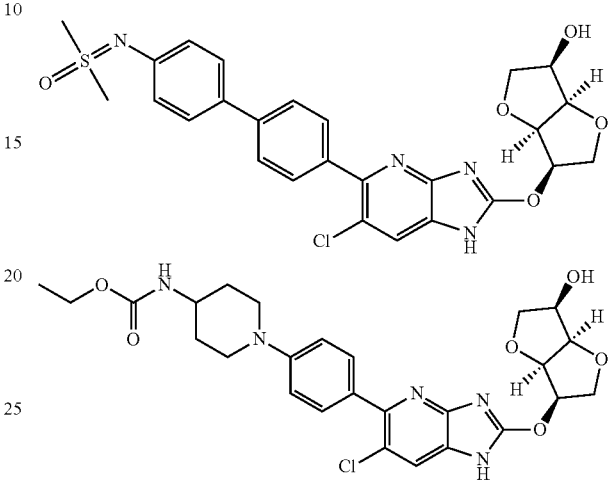

Patent Document 22 describes, for example, the compounds shown below as a compound having an AMPK activating effect.

[Chemical formula 2]

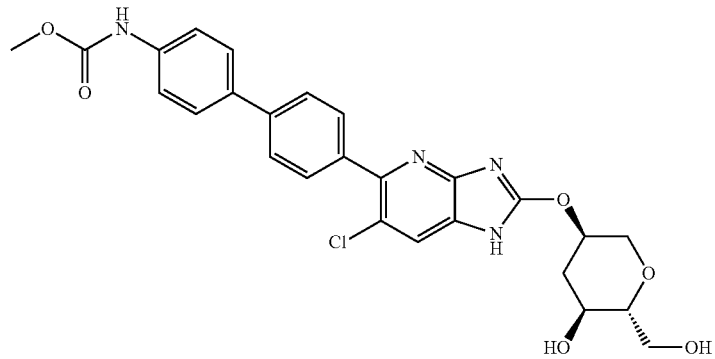

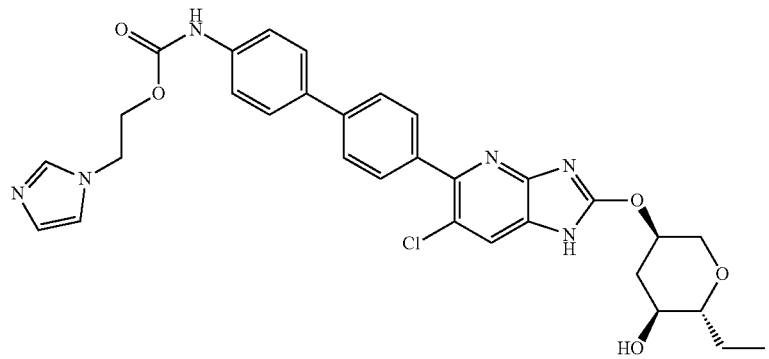

-continued
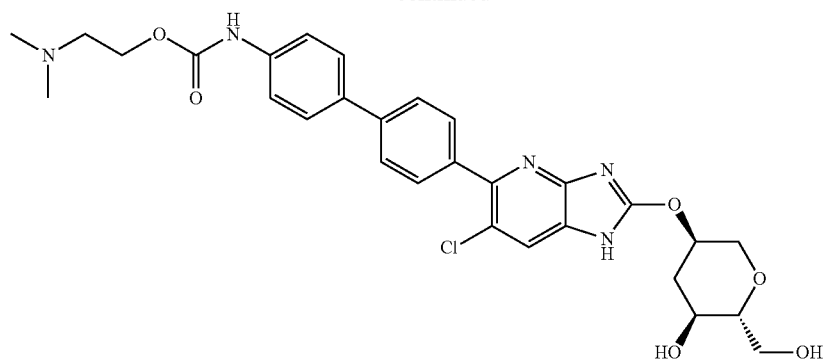
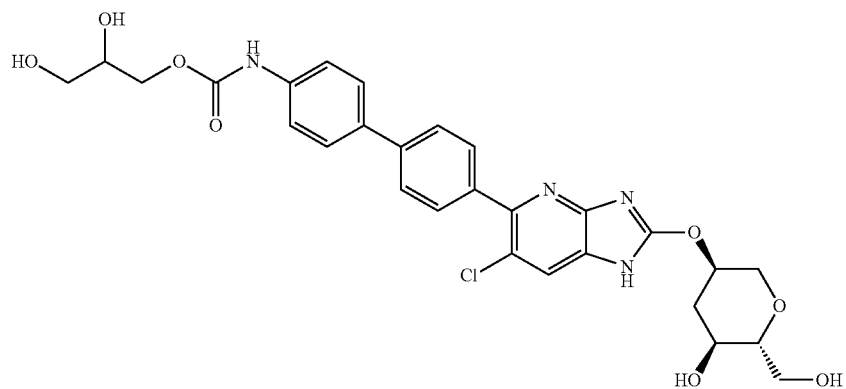
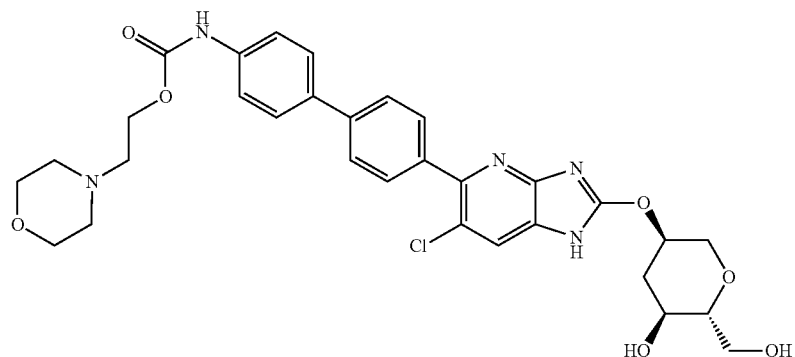 [SMILES: O=C(Nc1ccc(-c2ccc(-c3nc4nc(O[C@H]5CO[C@H](CO)[C@@H](O)C5)[nH]c4cc3Cl)cc2)cc1)OCCN1CCOCC1]

Patent Document 23 describes, for example, the compounds shown below as a compound having an AMPK activating effect.

[Chemical formula 3]

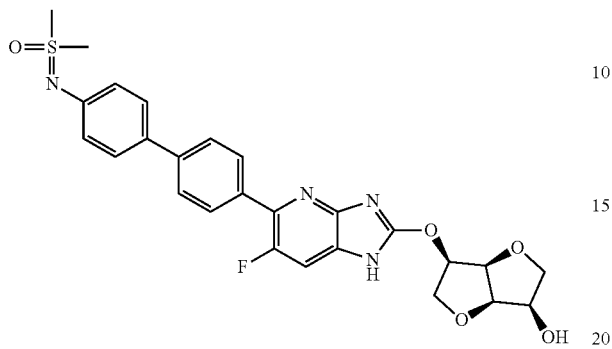

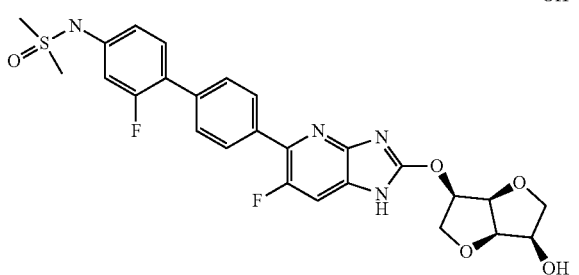

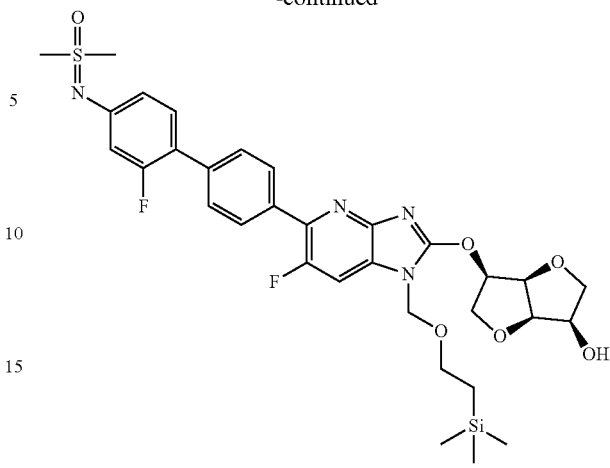

PRIOR ART DOCUMENT

Patent Document

Patent Document 1: WO 2010/036613
Patent Document 2: WO 2010/047982
Patent Document 3: WO 2010/051176
Patent Document 4: WO 2010/051206
Patent Document 5: WO 2011/106273
Patent Document 6: WO 2012/116145
Patent Document 7: WO 2012/033149
Patent Document 8: WO 2013/011932
Patent Document 9: WO 2014/031441
Patent Document 10: WO 2014/031445
Patent Document 11: WO 2014/031468
Patent Document 12: WO 2014/031517
Patent Document 13: WO 2014/031515
Patent Document 14: WO 2014/069426
Patent Document 15: WO 2014/139388
Patent Document 16: WO 2014/133008
Patent Document 17: WO 2014/175330
Patent Document 18: WO 2016/068099
Patent Document 19: WO 2015/007669
Patent Document 20: WO 2015/063011
Patent Document 21: WO 2016/023789
Patent Document 22: WO 2014/031465
Patent Document 23: WO 2016/113299

Non-Patent Document

Non-Patent Document 1: Cell Metabolism Vol. 9, Issue 5, 407-416, 2009

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.

The present invention relates to the following.

(1) A compound represented by the formula (I):

[Chemical formula 4]

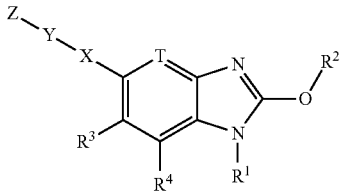

or its pharmaceutically acceptable salt,
wherein, $R^1$ is hydrogen, or substituted or unsubstituted alkyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

T is $-CR^5=$ or $-N=$;

X is a single bond, substituted or unsubstituted aryl, substituted or unsubstituted heteroaryl, substituted or unsubstituted cycloalkyl, substituted or unsubstituted cycloalkenyl, or substituted or unsubstituted heterocyclyl;

Y is substituted or unsubstituted aryl, substituted or unsubstituted heteroaryl, substituted or unsubstituted cycloalkyl, substituted or unsubstituted cycloalkenyl, or substituted or unsubstituted heterocyclyl;

Z is $R^S R^{S'}(O=)S=N-$, $R^S R^{S'}(O=)S=N-R^{2f}-$, $R^S R^{S'}(O=)S=N-C(=O)-$, $(R^N)N=S(=O)(R^S)-$, $(R^N)N=S(=O)(R^S)-R^{2f}-$, $R^S R^{S'}(R^{N'}-N=)S=N-$, $((R^N)N=)_2S(R^{S''})-$, $(R^N R^{N'})N-C(=O)-O-$, $R^O O-C(=O)-N(R^N)-$, $R^O O-C(=O)-O-$, $R^S(R^N R^{N'} N)(O=)S=N-$, $R^S(R^N R^{N'} N)(O=)S=N-R^{2f}-$, $(R^{N''})N=S(=O)(NR^N R^{N'})-$, $(R^{N''})N=S(=O)(NR^N R^{N'})-R^{2f}-$, $R^{P1} R^{P2}(O=)P-$,

[Chemical formula 5]

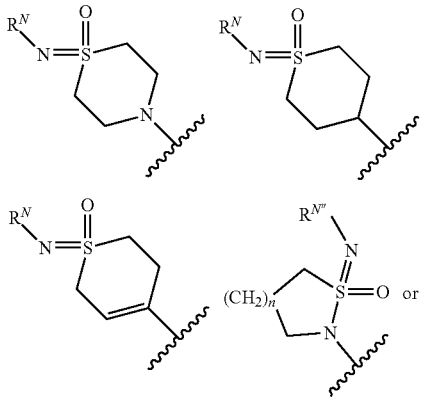

n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{S''}$ is hydrogen, substituted or unsubstituted alkyl, substituted or unsubstituted cycloalkyl, substituted or unsubstituted heterocyclyl, substituted or unsubstituted aryl, or substituted or unsubstituted heteroaryl;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

two $(R^N)N=$ bound to the same sulfur atom may form a substituted or unsubstituted ring together with the sulfur atom when Z is $((R^N)N=)_2 S(R^{S''})-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ and $R^{N'}$ bound to the same nitrogen atom may form a substituted or unsubstituted ring together with the nitrogen atom;

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{P1}$ and $R^{P2}$ are each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^3$, $R^4$ and $R^5$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that, when $R^2$ is

[Chemical formula 6]

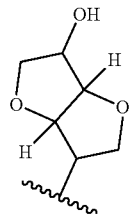

and T is —N═, $R^3$ is fluoro, cyano, substituted or unsubstituted alkyl, or substituted or unsubstituted alkyloxy; and compounds shown below are excluded

[Chemical formula 7]

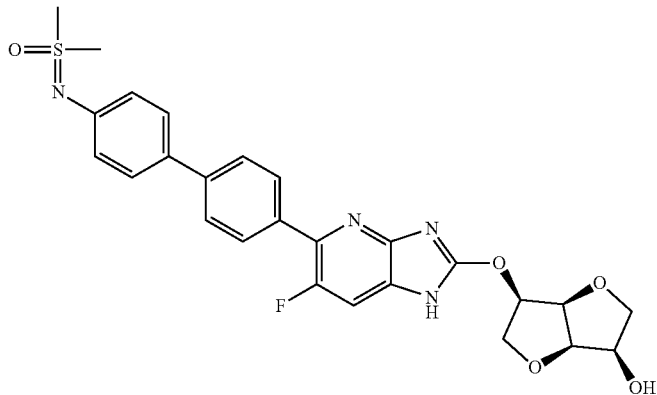

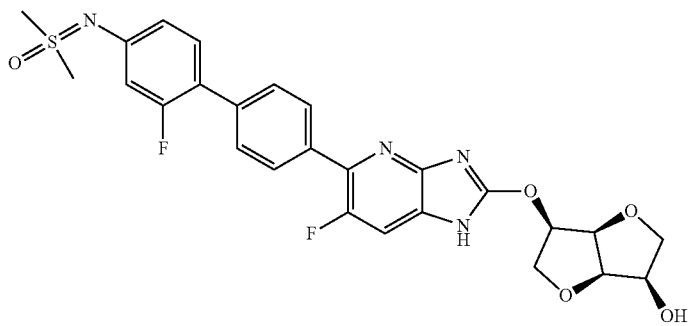

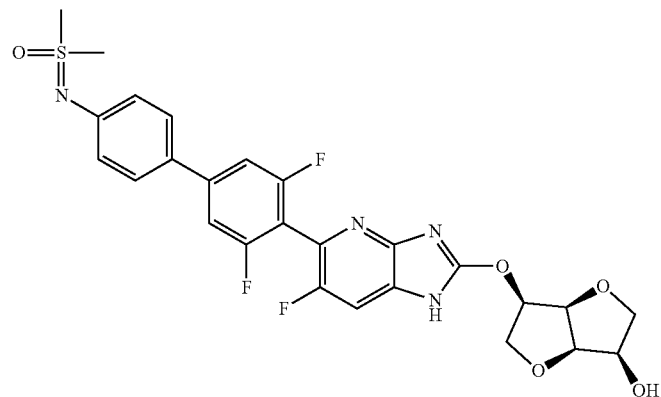
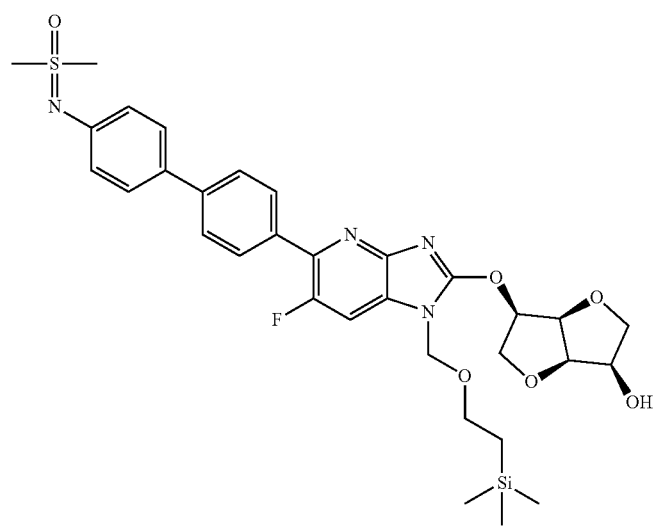
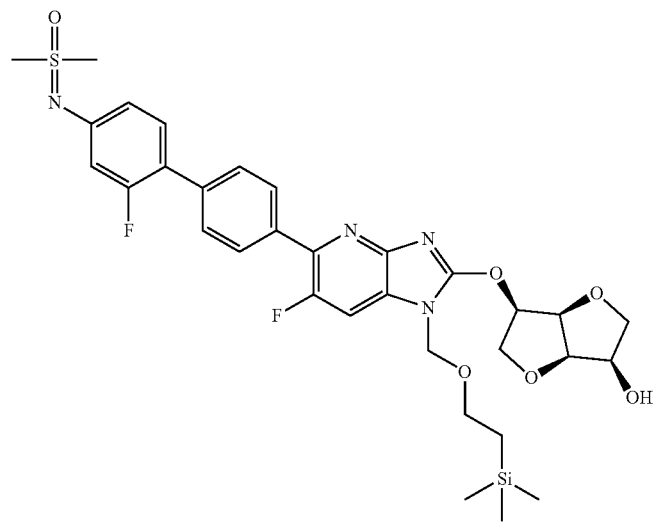 [SMILES: C[Si](C)(C)CCOCn1c(O[C@@H]2CO[C@H]3[C@@H]2OC[C@H]3O)nc2nc(-c3ccc(-c4ccc(N=S(C)(C)=O)cc4F)cc3)c(F)cc21]

-continued
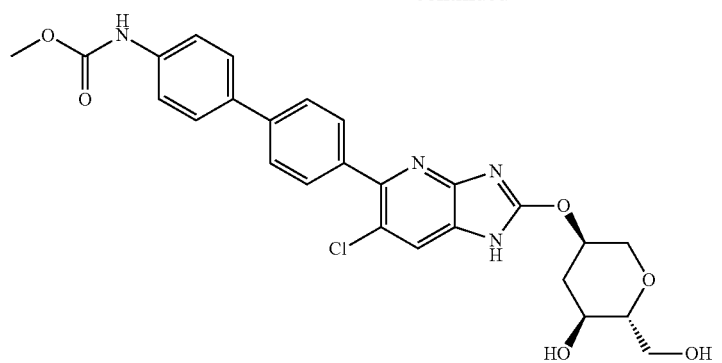
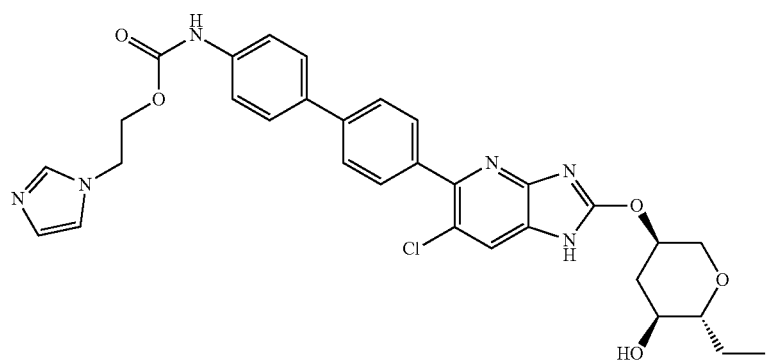
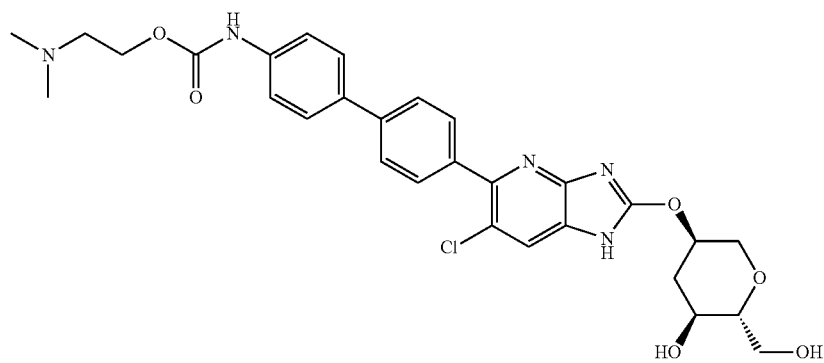
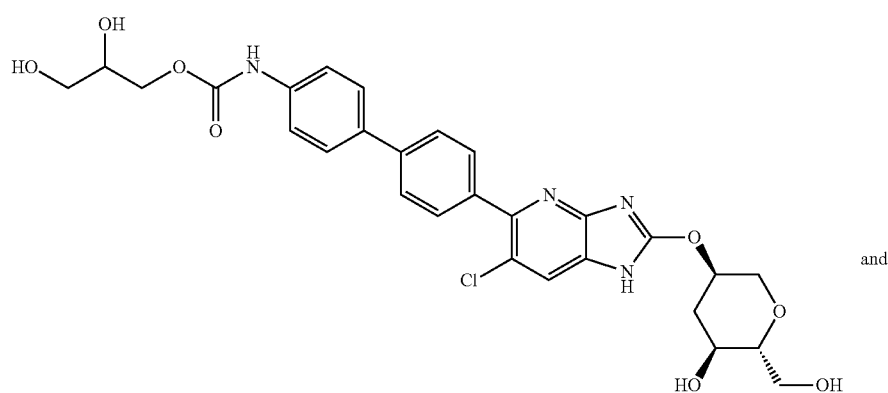
and

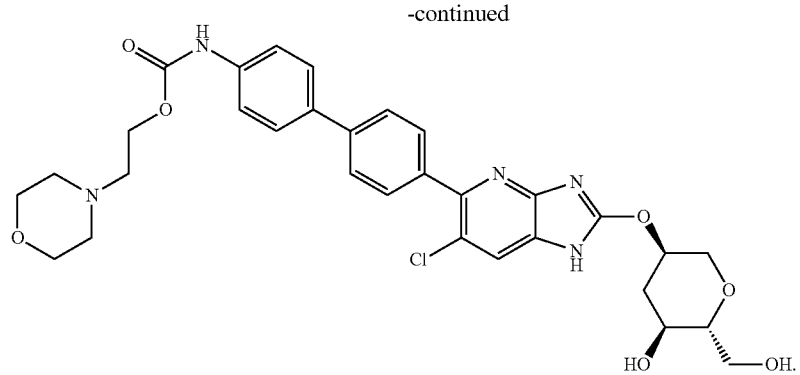

(2)

The compound according to the above (1) or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(3)

The compound according to the above (2) or its pharmaceutically acceptable salt, wherein $R^2$ is substituted or unsubstituted cycloalkyl, or substituted or unsubstituted heterocyclyl.

(4)

The compound according to the above (2) or its pharmaceutically acceptable salt, wherein $R^2$ is aryl, heteroaryl, cycloalkyl, cycloalkenyl or heterocyclyl substituted with at least one group selected from halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(5)

The compound according to the above (4) or its pharmaceutically acceptable salt, wherein $R^2$ is cycloalkyl or heterocyclyl substituted with at least one group selected from halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(6)

The compound according to the above (2) or its pharmaceutically acceptable salt, wherein $R^2$ is aryl, heteroaryl, cycloalkyl, cycloalkenyl or heterocyclyl substituted with at least one halogen, and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(7)

The compound according to the above (6) or its pharmaceutically acceptable salt, wherein $R^2$ is cycloalkyl or heterocyclyl substituted with at least one halogen, and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(8)

The compound according to the above (5) or its pharmaceutically acceptable salt,
wherein $R^2$ is

[Chemical formula 8]

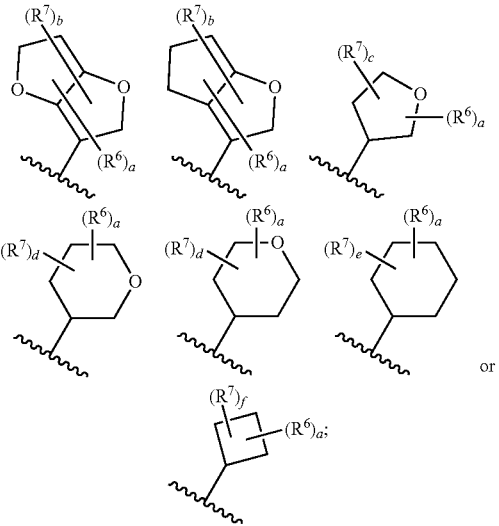

wherein R⁶ is each independently halogen, —PO(OH)₂, substituted or unsubstituted heteroaryl, substituted or unsubstituted heterocyclyl, substituted or unsubstituted alkylthio, substituted or unsubstituted carbamoyl, substituted or unsubstituted sulfamoyl, or substituted or unsubstituted amino;

a is an integer from 1 to 3;

R⁷ is each independently hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl;

b is an integer from 0 to 8;

c is an integer from 0 to 6;

d is an integer from 0 to 8;

e is an integer from 0 to 10;

f is an integer from 0 to 6.

(9)

The compound according to the above (8) or its pharmaceutically acceptable salt, wherein R² is

[Chemical formula 9]

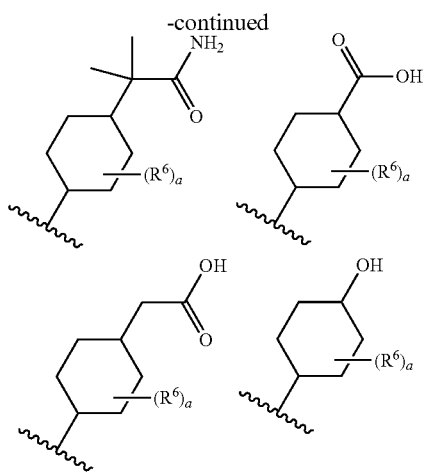

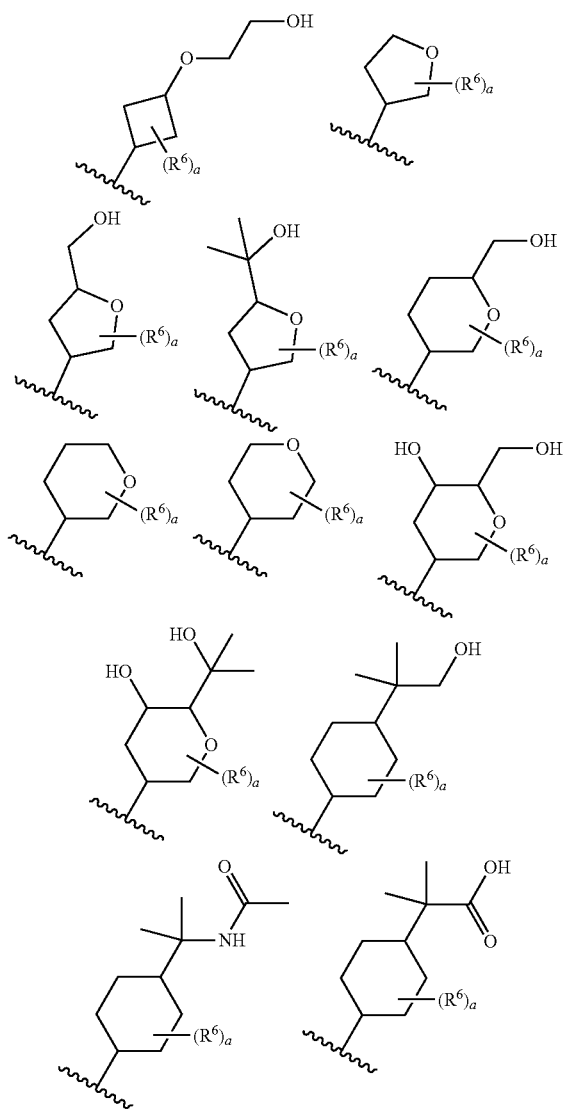

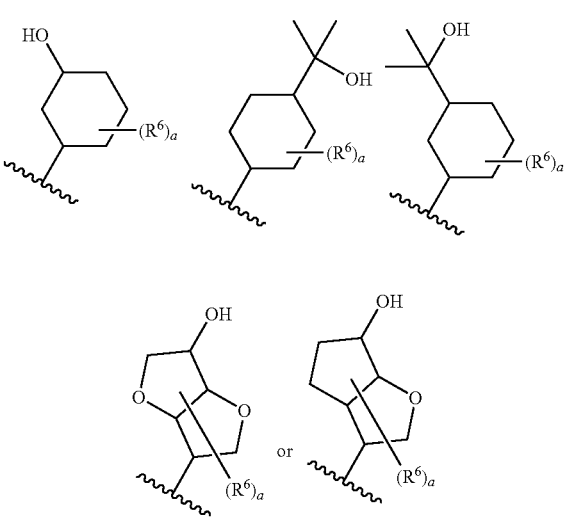

wherein R⁶ and a are as defined in the above (8).

(10)

The compound according to the above (8) or its pharmaceutically acceptable salt, wherein a is 1 or 2; and R⁶ is each independently halogen.

(11)

The compound according to the above (9) or its pharmaceutically acceptable salt, wherein a is 1 or 2; and R⁶ is each independently halogen.

(12)

The compound according to any one of the above (1) to (11) or its pharmaceutically acceptable salt, wherein R³ is halogen, cyano, substituted or unsubstituted alkyl, or substituted or unsubstituted alkyloxy.

(13)

The compound according to the above (12) or its pharmaceutically acceptable salt, wherein R³ is halogen.

(14)

The compound according to the above (1) or its pharmaceutically acceptable salt, wherein R² is substituted or unsubstituted cycloalkyl, or substituted or unsubstituted heterocyclyl; and R³ is fluoro, cyano, substituted or unsubstituted alkyl, or substituted or unsubstituted alkyloxy.

(15)
The compound according to the above (14) or its pharmaceutically acceptable salt, wherein $R^2$ is

[Chemical formula 10]

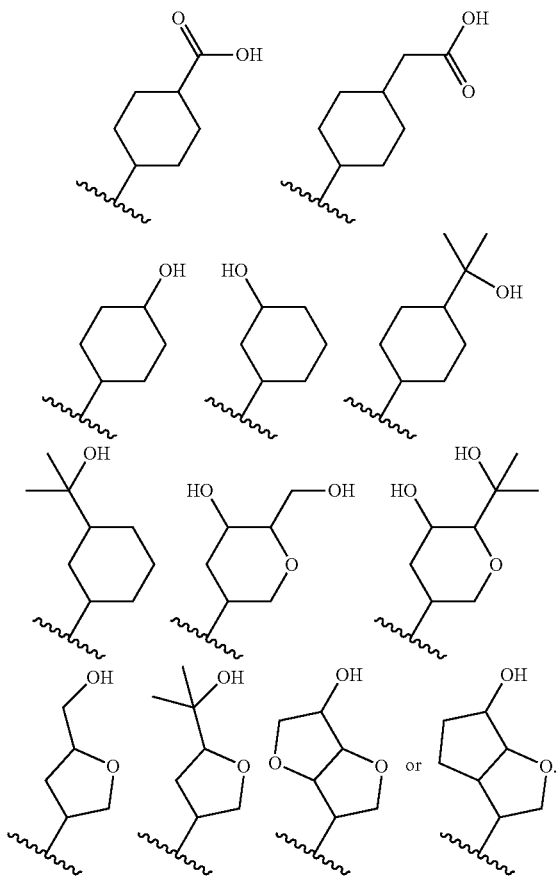

(16)
The compound according to the above (14) or (15), or its pharmaceutically acceptable salt, wherein $R^3$ is fluoro.
(17)
The compound according to any one of the above (1) to (16) or its pharmaceutically acceptable salt, wherein X is a single bond, substituted or unsubstituted aryl, substituted or unsubstituted heteroaryl, or substituted or unsubstituted heterocyclyl.
(18)
The compound according to any one of the above (1) to (17) or its pharmaceutically acceptable salt, wherein Y is substituted or unsubstituted aryl, substituted or unsubstituted cycloalkenyl, or substituted or unsubstituted heterocyclyl.
(19)
The compound according to any one of the above (1) to (18) or its pharmaceutically acceptable salt, wherein Z is $R^S R^{S'}(O=)S=N-$, $(R^N)N=S(=O)(R^S)-$, $R^O O-C(=O)-N(R^N)-$, or $R^S(R^N R^{N'}N)(O=)S=N-$.
(20)
The compound according to any one of the above (1) to (19) or its pharmaceutically acceptable salt, wherein T is $-N=$.
(21)
The compound according to any one of the above (1) to (20) or its pharmaceutically acceptable salt, wherein $R^1$ is hydrogen.

(22)
The compound according to any one of the above (1) to (21) or its pharmaceutically acceptable salt, wherein $R^4$ is hydrogen.
(23)
The compound according to the above (1) or its pharmaceutically acceptable salt, wherein the compound is selected from compound (I-1-2), (I-1-3), (I-1-4), (I-1-5), (I-1-6), (I-1-7), (I-1-8), (I-1-9), (I-1-10), (I-1-11), or (I-1-12).
(24)
The compound according to the above (1) or its pharmaceutically acceptable salt, wherein the compound is selected from compound (I-2-1), (I-2-2), (I-2-3), (I-2-4), (I-2-5), (I-2-6), (I-2-7), (I-2-8), (I-2-9), (I-2-10), (I-2-11), (I-2-12), (I-2-13), (I-2-14), or (I-2-15).
(25)
A pharmaceutical composition comprising the compound according to any one of the above (1) to (24) or its pharmaceutically acceptable salt.
(26)
The pharmaceutical composition according to the above (25), which has an activating effect on adenosine monophosphate-activated protein kinase.
(27)
The pharmaceutical composition according to the above (25) or (26), for the treatment and/or prevention of diabetes.
(28)
A method for preventing or treating diabetes, comprising administering the compound according to any one of the above (1) to (24), or its pharmaceutically acceptable salt.
(29)
The compound according to any one of the above (1) to (24), or its pharmaceutically acceptable salt, for the treatment and/or prevention of diabetes.
(30)
A pharmaceutical composition for oral administration, comprising a compound represented by formula (I), or its pharmaceutically acceptable salt,
(31)
The pharmaceutical composition according to the above (30), which is a tablet, powder, granule, capsule, pill, film, suspension, emulsion, elixir, syrup, lemonade, spirit, aromatic water, extract, decoction or tincture.
(32)
The pharmaceutical composition according to the above (31), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.
(33)
A pharmaceutical composition for parenteral administration, comprising a compound represented by formula (I), or its pharmaceutically acceptable salt.
(34)
The pharmaceutical composition according to the above (33), for dermal, subcutaneous, intravenous, intraarterial, intramuscular, intraperitoneal, transmucosal, inhalation, transnasal, ophthalmic, inner ear or vaginal administration.
(35)
The pharmaceutical composition according to the above (33) or (34), which is injection, infusion, ophthalmic drop, nose drop, ear drop, aerosol, inhalation, lotion, impregnation, liniment, mouthwash, enema, ointment, plaster, jelly, cream, patch, cataplasm, external powder or suppository.

(36)

A pharmaceutical composition for a pediatric or geriatric patient, comprising a compound represented by formula (I), or its pharmaceutically acceptable salt.

(37)

A pharmaceutical composition consisting of a combination of a compound represented by formula (I) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(38)

A pharmaceutical composition comprising a compound represented by formula (I) or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(1A)

A compound represented by the formula (I):

[Chemical formula 11]

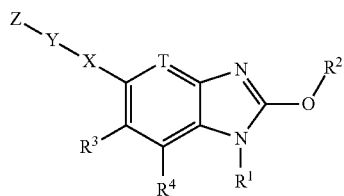

(I)

or its pharmaceutically acceptable salt, wherein, $R^1$ is hydrogen, or substituted or unsubstituted alkyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

T is —$CR^5$= or —N=;

X is a single bond, substituted or unsubstituted aryl, substituted or unsubstituted heteroaryl, substituted or unsubstituted cycloalkyl, substituted or unsubstituted cycloalkenyl, or substituted or unsubstituted heterocyclyl;

Y is substituted or unsubstituted aryl, substituted or unsubstituted heteroaryl, substituted or unsubstituted cycloalkyl, substituted or unsubstituted cycloalkenyl, or substituted or unsubstituted heterocyclyl;

Z is $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}—$, $R^SR^{S'}(R^{N'}—N=)S=N—$, $((R^N)N=)_2S(R^{S''})—$, $(R^NR^{N'})N—C(=O)—O—$, $R^OO—C(=O)—N(R^N)—$, $R^OO—C(=O)—O—$, $R^S(R^NR^{N'}N)(O=)S=N—$, $R^S(R^NR^{N'}N)(O=)S=N—R^{2f}—$, $(R^{N''})N=S(=O)(NR^NR^{N'})—$, $(R^{N''})N=S(=O)(NR^NR^{N'})—R^{2f}—$,

[Chemical formula 12]

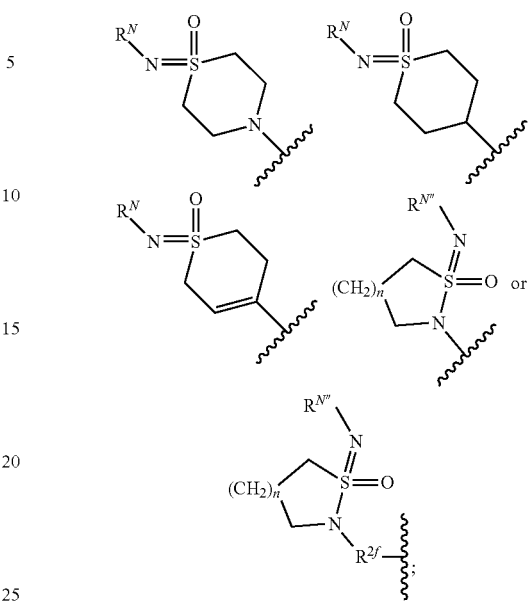

n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{S''}$ is hydrogen, substituted or unsubstituted alkyl, substituted or unsubstituted cycloalkyl, substituted or unsubstituted heterocyclyl, substituted or unsubstituted aryl, or substituted or unsubstituted heteroaryl;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

two $(R^N)N=$ bound to the same sulfur atom may form a substituted or unsubstituted ring together with the sulfur atom when Z is $((R^N)N=)_2S(R^{S''})—$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ and $R^{N'}$ bound to the same nitrogen atom may form a substituted or unsubstituted ring together with the nitrogen atom;

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^3$, $R^4$ and $R^5$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substitute d or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that, when $R^2$ is

[Chemical formula 13]

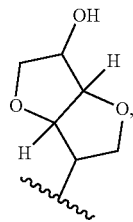

and T is —N=, $R^3$ is fluoro, cyano, substituted or unsubstituted alkyl, or substituted or unsubstituted alkyloxy.

(2A)

The compound according to the above (1A), or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(3A)

The compound according to the above (2A), or its pharmaceutically acceptable salt, wherein $R^2$ is substituted or unsubstituted cycloalkyl, or substituted or unsubstituted heterocyclyl.

(4A)

The compound according to the above (2A), or its pharmaceutically acceptable salt, wherein $R^2$ is aryl, heteroaryl, cycloalkyl, cycloalkenyl or heterocyclyl substituted with at least one group selected from halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(5A)

The compound according to the above (4A), or its pharmaceutically acceptable salt, wherein $R^2$ is cycloalkyl or heterocyclyl substituted with at least one group selected from halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(6A)

The compound according to the above (2A), or its pharmaceutically acceptable salt, wherein $R^2$ is aryl, heteroaryl, cycloalkyl, cycloalkenyl or heterocyclyl substituted with at least one halogen, and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(7A)

The compound according to the above (6A), or its pharmaceutically acceptable salt, wherein $R^2$ is cycloalkyl or heterocyclyl substituted with at least one halogen, and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

(8A)

The compound according to the above (7A), or its pharmaceutically acceptable salt, wherein $R^2$ is

[Chemical formula 14]

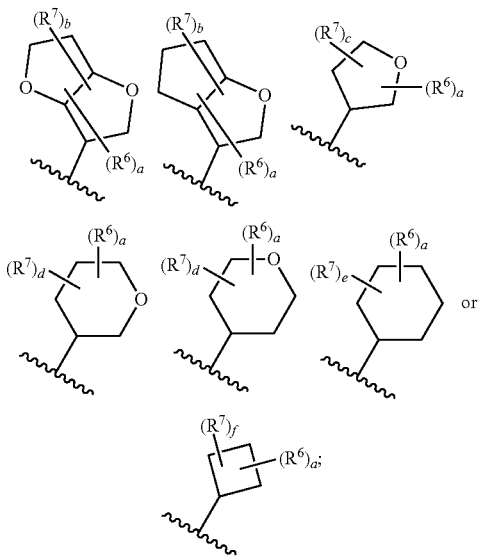

wherein $R^6$ is each independently halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, or substituted or unsubstituted amino;

a is an integer from 1 to 3;

$R^7$ is each independently hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl;

b is an integer from 0 to 8;

c is an integer from 0 to 6;

d is an integer from 0 to 8;

e is an integer from 0 to 10;

f is an integer from 0 to 6.

(9A)

The compound according to the above (8A), or its pharmaceutically acceptable salt, wherein $R^2$ is

[Chemical formula 15]

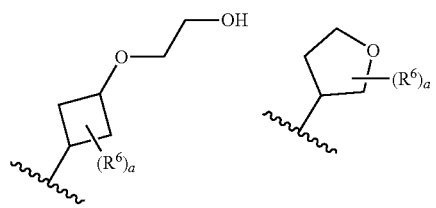

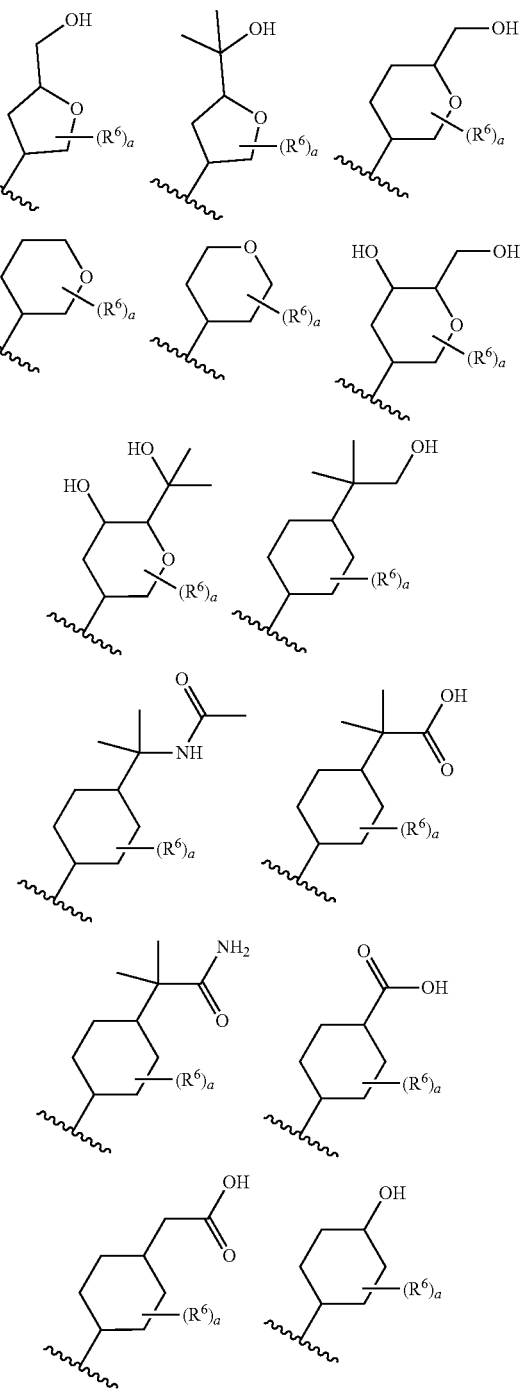

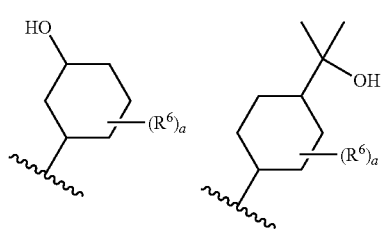

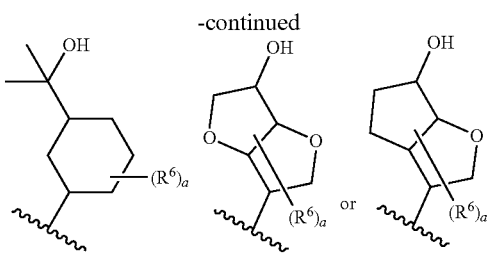

wherein R⁶ and a are as defined in the above (8A).

(10A) The compound according to the above (8A), or its pharmaceutically acceptable salt, wherein a is 1 or 2; and R⁶ is each independently halogen.

(11A) The compound according to the above (9A), or its pharmaceutically acceptable salt, wherein a is 1 or 2; and R⁶ is each independently halogen.

(12A) The compound according to any one of the above (1A) to (11A), or its pharmaceutically acceptable salt, wherein $R^3$ is halogen, cyano, substituted or unsubstituted alkyl, or substituted or unsubstituted alkyloxy.

(13A) The compound according to the above (12A), or its pharmaceutically acceptable salt, wherein $R^3$ is halogen.

(14A) The compound according to the above (1A), or its pharmaceutically acceptable salt, wherein $R^2$ is substituted or unsubstituted cycloalkyl, or substituted or unsubstituted heterocyclyl; and $R^3$ is fluoro, cyano, substituted or unsubstituted alkyl, or substituted or unsubstituted alkyloxy.

(15A) The compound according to the above (14A), or its pharmaceutically acceptable salt, wherein $R^2$ is

[Chemical formula 16]

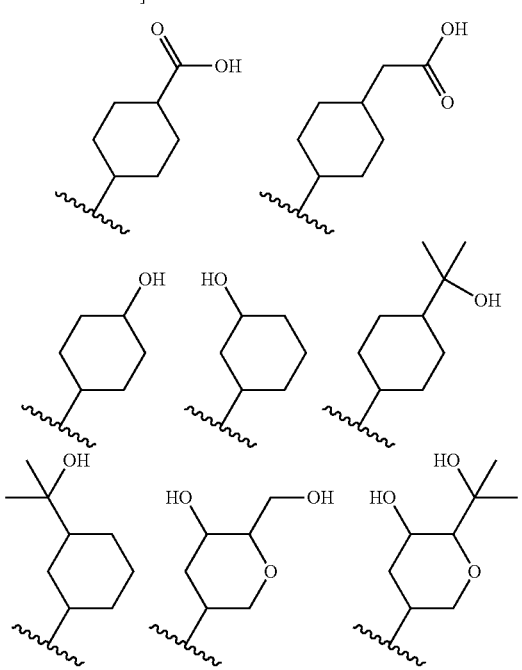

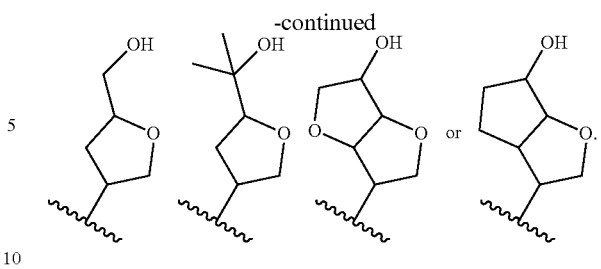

(16A) The compound according to the above (14A) or (15A), or its pharmaceutically acceptable salt, wherein $R^3$ is fluoro.

(17A) The compound according to any one of the above (1A) to (16A), or its pharmaceutically acceptable salt, wherein X is a single bond, substituted or unsubstituted aryl, substituted or unsubstituted heteroaryl, or substituted or unsubstituted heterocyclyl.

(18A) The compound according to any one of the above (1A) to (17A), or its pharmaceutically acceptable salt, wherein Y is substituted or unsubstituted aryl, substituted or unsubstituted cycloalkenyl, or substituted or unsubstituted heterocyclyl.

(19A) The compound according to any one of the above (1A) to (18A), or its pharmaceutically acceptable salt, wherein Z is $R^S R^{S'}(O=)S=N-$, $(R^N)N=S(=O)(R^S)-$, $R^O O-C(=O)-N(R^N)-$, or $R^S(R^N R^{N'}N)(O=)S=N-$.

(20A) The compound according to any one of the above (1A) to (19A), or its pharmaceutically acceptable salt, wherein T is $-N=$.

(21A) The compound according to any one of the above (1A) to (20A), or its pharmaceutically acceptable salt, wherein $R^1$ is hydrogen.

(22A) The compound according to any one of the above (1A) to (21A), or its pharmaceutically acceptable salt, wherein $R^4$ is hydrogen.

(23A) The compound according to the above (1A), or its pharmaceutically acceptable salt, wherein the compound is selected from compound (I-1-1), (I-1-2), (I-1-3), (I-1-4), (I-1-5), (I-1-6), (I-1-7), (I-1-8), (I-1-9), (I-1-10), (I-1-11), or (I-1-12).

(24A) A pharmaceutical composition comprising the compound according to any one of the above (1A) to (23A), or its pharmaceutically acceptable salt.

(25A) The pharmaceutical composition according to the above (24A), which has an activating effect on adenosine monophosphate-activated protein kinase.

(26A) A method for preventing or treating diabetes, comprising administering the compound according to any one of the above (1A) to (23A), or its pharmaceutically acceptable salt.

(27A) The compound according to any one of the above (1A) to (23A), or its pharmaceutically acceptable salt, for the treatment and/or prevention of diabetes.

(28A)
The pharmaceutical composition according to the above (24A) or (25A), for the treatment and/or prevention of diabetes.
(29A)
A pharmaceutical composition for oral administration, comprising a compound represented by formula (I), or its pharmaceutically acceptable salt.
(30A)
The pharmaceutical composition according to the above (29A), which is a tablet, powder, granule, capsule, pill, film, suspension, emulsion, elixir, syrup, lemonade, spirit, aromatic water, extract, decoction or tincture.
(31A)
The pharmaceutical composition according to the above (30A), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.
(32A)
A pharmaceutical composition for parenteral administration, comprising a compound represented by formula (I), or its pharmaceutically acceptable salt.
(33A)
The pharmaceutical composition according to the above (32A), for dermal, subcutaneous, intravenous, intraarterial, intramuscular, intraperitoneal, transmucosal, inhalation, transnasal, ophthalmic, inner ear or vaginal administration.
(34A)
The pharmaceutical composition according to the above (32A) or (33A), which is injection, infusion, ophthalmic drop, nose drop, ear drop, aerosol, inhalation, lotion, impregnation, liniment, mouthwash, enema, ointment, plaster, jelly, cream, patch, cataplasm, external powder or suppository.
(35A)
A pharmaceutical composition for a pediatric or geriatric patient, comprising a compound represented by formula (I), or its pharmaceutically acceptable salt.
(36A)
A pharmaceutical composition consisting of a combination of a compound represented by formula (I) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.
(37A)
A pharmaceutical composition comprising a compound represented by formula (I) or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

Effect of the Invention

The compound of the present invention has an AMPK activating effect, and thus a pharmaceutical composition comprising a compound of the pre sent invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral absorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin $A_{1C}$ (HbA1c), the effect of improving fatty hepatic or the like.

MODE FOR CARRYING OUT THE INVENTION

Each term used in this description will be described below. In this description, even when each term is used individually or used with other terms, the term has the same meaning.

"Halogen" includes fluorine, chlorine, bromine and iodine.

"Alkyl" means a C1 to C10 straight or branched alkyl group, and examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl and the like. Preferable examples include C1 to C6 or C1 to C4 alkyl, and examples thereof include methyl, ethyl, n-propyl, isopropyl, n-butyl, isobutyl, sec-butyl, tert-butyl, n-pentyl, isopentyl, neopentyl, n-hexyl and isohexyl.

"Alkenyl" means C2 to C8 straight or branched alkenyl having one or more double bond(s) in the above "alkyl", and examples thereof include vinyl, 1-propenyl, 2-propenyl, 1-butenyl, 2-butenyl, 3-butenyl, 1,3-butadienyl, 3-methyl-2-butenyl and the like.

"Alkynyl" means C2 to C8 straight or branched alkynyl having one or more triple bond(s) in the above "alkyl", and examples thereof include ethynyl, propynyl, butynyl and the like. Furthermore, an "alkynyl" may have a double bond.

"Cycloalkyl" means a C3 to C15 cyclic saturated hydrocarbon group, and examples thereof include cyclopropyl, cyclobutyl, cyclopentyl, cyclohexyl, cycloheptyl, cyclooctyl, bridged cyclic hydrocarbon group, spiro hydrocarbon group and the like. Preferable examples include cyclopropyl, cyclobutyl, cyclopentyl, cyclohexyl or bridged cyclic hydrocarbon group.

A "bridged cyclic hydrocarbon group" includes a group which is derived by removing one hydrogen from a C5 to C8 aliphatic cycle which consists of two or more rings that share two or more atoms. Specific examples thereof include bicyclo[2.1.0]pentyl, bicyclo[2.2.1]heptyl, bicyclo[2.2.2]octyl, bicyclo[3.2.1]octyl, tricyclo[2.2.1.0]heptyl and the like.

A "spiro hydrocarbon group" includes a group which is derived by removing one hydrogen from a cycle which consists of two hydrocarbon rings that share one carbon atom. Specific examples thereof include spiro[3.4]octyl and the like.

"Cycloalkenyl" means C3 to C10 cyclic unsaturated aliphatic hydrocarbon group, and examples thereof include cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl and 3-cyclopenten-1-yl), cyclohexenyl (e.g., 1-cyclohexen-1-yl, 2-cyclohexen-1-yl and 3-cyclohexen-1-yl), cycloheptenyl (e.g., 1-cycloheptenyl), cyclooctenyl (e.g., 1-cyclooctenyl) and the like. Preferable is cyclopropenyl, cyclobutenyl, cyclopentenyl or cyclohexenyl. Cycloalkenyls also include bridged cyclic hydrocarbon group and spiro hydrocarbon group which both have an unsaturated bond in the ring. Cycloalkenyls also include cyclic groups in which cycloalkene or a benzene ring is condensed with the cycloalkyl. For examples, cycloalkenyls also include the groups shown below.

[Chemical formula 17]

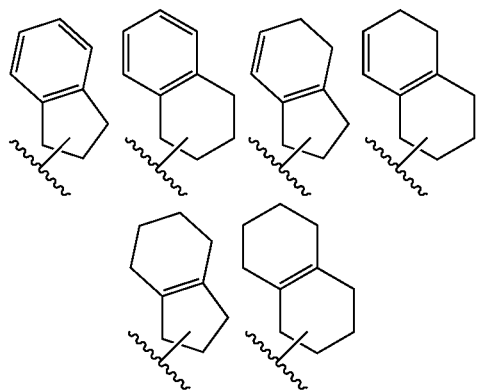

"Aryl" means a monocyclic aromatic hydrocarbon group (e.g., phenyl) and a polycyclic aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, etc.). Preferable examples include phenyl or naphthyl (1-naphthyl or 2-naphthyl).

"Heteroaryl" means a monocyclic aromatic heterocyclic group and a fused aromatic heterocyclic group.

A "monocyclic aromatic heterocyclic group" means a group which is derived from a 5 to 8-membered aromatic ring which has one or more same or different heteroatoms optionally selected from oxygen, sulfur and nitrogen atoms in the ring, which group may have a bond at any substitutable position.

A "fused aromatic heterocyclic group" means a group in which a 5 to 8-membered aromatic ring which has one or more same or different heteroatoms optionally selected from oxygen, sulfur and nitrogen atoms in the ring is fused with one to four 5 to 8-membered aromatic carbocyclic rings or another 5 to 8-membered aromatic hetero ring, which group may have a bond at any substitutable position.

Examples of a "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), benzopyrazolyl, dibenzofuryl, benzoxazolyl, benzothiazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl) and the like.

"Heterocyclyl" means a non-aromatic heterocyclic group, which may have a bond at any substitutable position of a ring which has at least one or more nitrogen, oxygen or sulfur atoms in the ring, or a ring in which such ring is fused with a cycloalkane (preferably 5 to 6-membered), a benzene ring and/or a ring which has at least one or more nitrogen, oxygen or sulfur atoms in the ring. A "non-aromatic heterocyclic group" can be saturated or unsaturated as long as it is non-aromatic. Preferable is a 5- to 10-membered ring. Examples thereof include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, tetrahydrofuranyl, 1,2,3,4-tetrahydroisoquinolinyl, 1,2,3,4-tetrahydroquinolinyl, 1,3-dihydro-2H-isoindol-5-yl, the following group and the like.

[Chemical formula 18]

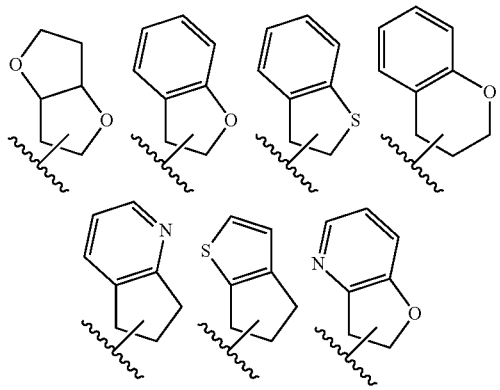

Further, examples of a "heterocyclyl" group also include a bridged group or a spiro ring forming group shown below.

[Chemical formula 19]

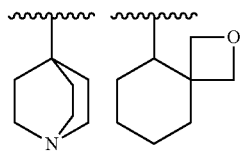

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl. The "alkyl" part of "alkylcarbonyl", the "alkenyl" part of "alkenylcarbonyl", the "cycloalkyl" part of "cycloalkylcarbonyl", the "cycloalkenyl" part of "cycloalkenylcarbonyl", the "aryl" part of "arylcarbonyl", the "heteroaryl" part of "heteroarylcarbonyl" and the "heterocyclyl" part of "heterocyclylcarbonyl" mean the above "alkyl", the above "alkenyl", the above "cycloalkyl", the above "cycloalkenyl", the above "aryl", the above "heteroaryl" and the above "heterocyclyl", respectively.

The alkyl parts of "alkylcarbonyl", "alkyloxycarbonyl", "alkylcarbamoyl", "alkylsulfonyl", "alkyloxy" and "alkylthio" mean the above "alkyl".

The aryl parts of "arylcarbonyl", "aryloxycarbonyl", "arylsulfonyl", "aryloxy" and "arylthio" mean the above "aryl".

The heteroaryl parts of "heteroarylcarbonyl", "heteroaryloxy", "heteroarylthio" and "heteroarylsulfonyl" mean the above "heteroaryl".

The cycloalkyl parts of "cycloalkylcarbonyl", "cycloalkyloxy", "cycloalkylthio" and "cycloalkylsulfonyl" mean the above "cycloalkyl".

The cycloalkenyl parts of "cycloalkenyloxy", "cycloalkenylthio" and "cycloalkenylsulfonyl" mean the above "cycloalkenyl".

The heterocyclyl parts of "heterocyclylcarbonyl", "heterocyclyloxy", "heterocyclylthio" and "heterocyclylsulfonyl" mean the above-described "heterocyclyl".

Examples of substituents of a "substituted alkyl", "substituted alkenyl", "substituted alkynyl", "substituted aryl", "substituted heteroaryl", "substituted cycloalkyl", "substituted cycloalkenyl", "substituted heterocyclyl", "a ring formed by $R^S$ and $R^{S'}$ which are bound to the same sulfur atom, together with the sulfur atom", "substituted alkylene", "substituted alkylcarbonyl", "substituted alkyloxycarbonyl", "substituted cycloalkylcarbonyl", "substituted heterocyclylcarbonyl", "substituted arylcarbonyl", "substituted heteroarylcarbonyl", "a ring formed by two $(R^N)N=$ which are bound to the same sulfur atom, together with the sulfur atom in the formula: $((R^N)N=)_2S(R^{S''})-$", "a ring formed by $R^N$ and $R^{N'}$ which are bound to the same nitrogen atom, together with the nitrogen atom", "substituted alkylcarbamoyl", "substituted cycloalkynyl", "substituted acyl", "substituted aryloxycarbonyl", "substituted arylsulfonyl", "substituted alkylsulfonyl", "substituted alkyloxy", "substituted aryloxy", "substituted heteroaryloxy", "substituted cycloalkyloxy", "substituted cycloalkenyloxy", "substituted heterocyclyloxy", "substituted alkylthio", "substituted arylthio", "substituted heteroarylthio", "substituted cycloalkylthio", "substituted cycloalkenylthio", "substituted heterocyclylthio", "substituted heteroarylsulfonyl", "substituted cycloalkylsulfonyl", "substituted cycloalkenylsulfonyl" or "substituted heterocyclylsulfonyl" include groups selected from the group consisting of halogen; hydroxy; carboxy; nitro; cyano;

substituted or unsubstituted alkyl (when substituted, substituents include halogen, hydroxy, carboxy, nitro, cyano, alkyl, aryl, cycloalkyl, cycloalkenyl, heteroaryl heterocyclyl, alkylcarbonylamino. e.g., methyl, ethyl, isopropyl, tert-butyl, $CF_3$);

substituted or unsubstituted alkenyl (when substituted, substituents include halogen, hydroxy, carboxy, nitro, cyano, alkyl, aryl, cycloalkyl, cycloalkenyl, heteroaryl, heterocyclyl. e.g., vinyl);

substituted or unsubstituted alkynyl (when substituted, substituents include halogen, hydroxy, carboxy, nitro, cyano, alkyl, aryl, cycloalkyl, cycloalkenyl, heteroaryl, heterocyclyl. e.g., ethynyl);

substituted or unsubstituted aryl (when substituted, substituents include halogen, hydroxy, carboxy, nitro, cyano, alkyl, aryl, cycloalkyl, cycloalkenyl, heteroaryl, heterocyclyl. e.g., phenyl, naphthyl);

substituted or unsubstituted cycloalkyl (when substituted, substituents include halogen, hydroxy, carboxy, nitro, cyano, alkyl, aryl, cycloalkyl, cycloalkenyl, heteroaryl, heterocyclyl. e.g., cyclopropyl, cyclobutyl);

substituted or unsubstituted cycloalkenyl (when substituted, substituents include halogen, hydroxy, carboxy, nitro, cyano, alkyl, aryl, cycloalkyl, cycloalkenyl, heteroaryl, heterocyclyl. e.g., cyclopropenyl);

substituted or unsubstituted heteroaryl (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclyl (when substituted, substituents include halogen, hydroxy, carboxy, nitro, cyano, alkyl, aryl, cycloalkyl, cycloalkenyl, heteroaryl, heterocyclyl. e.g., morpholinyl, piperidyl, pyrrolidinyl);

substituted or unsubstituted alkyloxy (when substituted, substituents include halogen, hydroxy, carboxy, nitro, cyano, alkyl, aryl, cycloalkyl, cycloalkenyl, heteroaryl, heterocyclyl. e.g., methoxy, ethoxy);

substituted or unsubstituted alkenyloxy (when substituted, substituents include halogen, hydroxy, carboxy, nitro, cyano, alkyl, aryl, cycloalkyl, cycloalkenyl, heteroaryl, heterocyclyl. e.g., vinyloxy, allyloxy);

substituted or unsubstituted aryloxy (when substituted, substituents include halogen, hydroxy, carboxy, nitro, cyano, alkyl, aryl, cycloalkyl, cycloalkenyl, heteroaryl, heterocyclyl. e.g., phenyloxy);

substituted or unsubstituted cycloalkyloxy (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkenyloxy (when substituted, substituents include halogen, hydroxy, carboxy, nitro, cyano, alkyl, aryl, cycloalkyl, cycloalkenyl, heteroaryl, heterocyclyl);

substituted or unsubstituted heteroaryloxy (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclyloxy (when substituted, substituents include halogen, hydroxy, carboxy, nitro, cyano, alkyl, aryl, cycloalkyl, cycloalkenyl, heteroaryl, heterocyclyl);

substituted or unsubstituted arylalkyl (when substituted, substituents include halogen, hydroxy, carboxy, nitro, cyano, alkyl, aryl, cycloalkyl, cycloalkenyl, heteroaryl, heterocyclyl. e.g., benzyl);

substituted or unsubstituted silyloxy;

substituted or unsubstituted amino (e.g., amino, alkylamino (e.g., methylamino, ethylamino, dimethylamino), arylamino, cycloalkylamino, cycloalkenylamino, heteroarylamino, heterocyclylamino, acylamino (e.g., acetylamino, benzoylamino), arylalkylamino (e.g., benzylamino, tritylamino), hydroxyamino, alkyloxycarbonylamino, carbamoylamino, alkylsulfonylamino, arylsulfonylamino, cycloalkylsulfonylamino, cycloalkenylsulfonylamino, heteroarylsulfonylamino, heterocyclylsulfonylamino);

substituted or unsubstituted carbamoyl (when substituted, substituents include halogen, hydroxy, carboxy, nitro, cyano, alkyl, aryl, cycloalkyl, cycloalkenyl, heteroaryl, heterocyclyl. e.g., alkylcarbamoyl (e.g., methylcarbamoyl, ethylcarbamoyl, dimethylcarbamoyl), heteroarylalkylcarbamoyl);

substituted or unsubstituted carbamoyloxy (when substituted, substituents include halogen, hydroxy, carboxy, nitro, cyano, alkyl, aryl, cycloalkyl, cycloalkenyl, heteroaryl, heterocyclyl);

substituted or unsubstituted acyl (when substituted, substituents include halogen, hydroxy, carboxy, nitro, cyano, alkyl, aryl, cycloalkyl, cycloalkenyl, heteroaryl, heterocyclyl. e.g., alkylcarbonyl, arylcarbonyl, cycloalkylcarbonyl, cycloalkenylcarbonyl, heteroarylcarbonyl, heterocyclylcarbonyl, formyl, acetyl);

substituted or unsubstituted alkylsulfonyl (when substituted, substituents include halogen, hydroxy, carboxy, nitro, cyano, alkyl, aryl, cycloalkyl, cycloalkenyl, heteroaryl, heterocyclyl. e.g., methanesulfonyl, ethanesulfonyl);

substituted or unsubstituted arylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkenylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted heteroarylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted alkylthio (when substituted, substituents include halogen, hydroxy, carboxy, nitro, cyano, alkyl, aryl, cycloalkyl, cycloalkenyl, heteroaryl, heterocyclyl);

substituted or unsubstituted arylthio (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkylthio (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkenylthio (when substituted, substituents include halogen, hydroxy, carboxy, nitro, cyano, alkyl, aryl, cycloalkyl, cycloalkenyl, heteroaryl, heterocyclyl);

substituted or unsubstituted heteroarylthio (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclylthio (when substituted, substituents include halogen, hydroxy, carboxy, nitro, cyano, alkyl, aryl, cycloalkyl, cycloalkenyl, heteroaryl, heterocyclyl);

substituted or unsubstituted sulfamoyl (when substituted, substituents include halogen, hydroxy, carboxy, nitro, cyano, alkyl, aryl, cycloalkyl, cycloalkenyl, heteroaryl, heterocyclyl);

substituted or unsubstituted alkyloxycarbonyl (when substituted, substituents include halogen, hydroxy, carboxy, nitro, cyano, alkyl, aryl, cycloalkyl, cycloalkenyl, heteroaryl, heterocyclyl. e.g., methoxycarbonyl, ethoxycarbonyl, tert-butoxycarbonyl);

substituted or unsubstituted aryloxycarbonyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkyloxycarbonyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkenyloxycarbonyl (when substituted, substituents include halogen, hydroxy, carboxy, nitro, cyano, alkyl, aryl, cycloalkyl, cycloalkenyl, heteroaryl, heterocyclyl);

substituted or unsubstituted heteroaryloxycarbonyl (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclyloxycarbonyl (when substituted, substituents include halogen, hydroxy, carboxy, nitro, cyano, alkyl, aryl, cycloalkyl, cycloalkenyl, heteroaryl, heterocyclyl);

substituted or unsubstituted alkylsulfinyl (when substituted, substituents include halogen, hydroxy, carboxy, nitro, cyano, alkyl, aryl, cycloalkyl, cycloalkenyl, heteroaryl, heterocyclyl);

substituted or unsubstituted arylsulfinyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkylsulfinyl (when substituted, substituents include halogen, hydroxy, carboxy, nitro, cyano, alkyl, aryl, cycloalkyl, cycloalkenyl, heteroaryl, heterocyclyl);

substituted or unsubstituted cycloalkenylsulfinyl (when substituted, substituents include halogen, hydroxy, carboxy, nitro, cyano, alkyl, aryl, cycloalkyl, cycloalkenyl, heteroaryl, heterocyclyl);

substituted or unsubstituted heteroarylsulfinyl (when substituted, substituents include halogen, hydroxy, carboxy, nitro, cyano, alkyl, aryl, cycloalkyl, cycloalkenyl, heteroaryl, heterocyclyl);

substituted or unsubstituted heterocyclylsulfinyl (when substituted, substituents include halogen, hydroxy, carboxy, nitro, cyano, alkyl, aryl, cycloalkyl, cycloalkenyl, heteroaryl, heterocyclyl);

nitroso;

substituted or unsubstituted alkylidene (when substituted, substituents include halogen, hydroxy, carboxy, nitro, cyano, alkyl, aryl, cycloalkyl, cycloalkenyl, heteroaryl, heterocyclyl);
azido;
—PO(OH)$_2$;
—PO(OCH$_2$CH$_3$)$_2$;
isocyano; isocyanato; thiocyanato; isothiocyanato; mercapto;
formyloxy; haloformyl; oxalo; thioformyl; thiocarboxy; dithiocarboxy; thiocarbamoyl; sulfino; sulfo; sulfoamino; hydrazino; ureido; amidino; guanidino; phthalimido; oxo and the like. The above-described substituted groups may have one to four of these substituents.

Preferred examples of a substituents of "substituted carbamoyl", "substituted sulfamoyl" or "substituted amino" include
substituted or unsubstituted alkyl (when substituted, substituents include halogen, hydroxy, carboxy, nitro, cyano, alkyl, aryl, cycloalkyl, cycloalkenyl, heteroaryl or heterocyclyl. e.g., methyl, ethyl, isopropyl, tert-butyl, CF$_3$);
substituted or unsubstituted alkenyl (when substituted, substituents include halogen, hydroxy, carboxy, nitro, cyano, alkyl, aryl, cycloalkyl, cycloalkenyl, heteroaryl, heterocyclyl. e.g., vinyl);
substituted or unsubstituted aryl (when substituted, substituents include halogen, hydroxy, carboxy, nitro, cyano, alkyl, aryl, cycloalkyl, cycloalkenyl, heteroaryl, heterocyclyl. e.g., phenyl, naphthyl);
substituted or unsubstituted cycloalkyl (when substituted, substituents include halogen, hydroxy, carboxy, nitro, cyano, alkyl, aryl, cycloalkyl, cycloalkenyl, heteroaryl, heterocyclyl. e.g., cyclopropyl, cyclobutyl);
substituted or unsubstituted cycloalkenyl (when substituted, substituents include halogen, hydroxy, carboxy, nitro, cyano, alkyl, aryl, cycloalkyl, cycloalkenyl, heteroaryl, heterocyclyl. e.g., cyclopropenyl);
substituted or unsubstituted heteroaryl (when substituted, substituents include halogen, hydroxy, carboxy, nitro, cyano, alkyl, aryl, cycloalkyl, cycloalkenyl, heteroaryl, heterocyclyl);
substituted or unsubstituted heterocyclyl (when substituted, substituents include halogen, hydroxy, carboxy, nitro, cyano, alkyl, aryl, cycloalkyl, cycloalkenyl, heteroaryl, heterocyclyl);
substituted or unsubstituted arylalkyl (when substituted, substituents include halogen, hydroxy, carboxy, nitro, cyano, alkyl, aryl, cycloalkyl, cycloalkenyl, heteroaryl, heterocyclyl);
substituted or unsubstituted alkyloxy (when substituted, substituents include halogen, hydroxy, carboxy, nitro, cyano, alkyl, aryl, cycloalkyl, cycloalkenyl, heteroaryl, heterocyclyl. e.g., methoxy, ethoxy);
substituted or unsubstituted aryloxy (when substituted, substituents include halogen, hydroxy, carboxy, nitro, cyano, alkyl, aryl, cycloalkyl, cycloalkenyl, heteroaryl, heterocyclyl. e.g., phenyloxy);
substituted or unsubstituted cycloalkyloxy (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkenyloxy (when substituted, substituents include halogen, hydroxy, carboxy, nitro, cyano, alkyl, aryl, cycloalkyl, cycloalkenyl, heteroaryl, heterocyclyl);
substituted or unsubstituted heteroaryloxy (when substituted, substituents include halogen, hydroxy, carboxy, nitro, cyano, alkyl, aryl, cycloalkyl, cycloalkenyl, heteroaryl, heterocyclyl);
substituted or unsubstituted heterocyclyloxy (when substituted, substituents include halogen, hydroxy, carboxy, nitro, cyano, alkyl, aryl, cycloalkyl, cycloalkenyl, heteroaryl, heterocyclyl);
substituted or unsubstituted acyl (when substituted, substituents include halogen, hydroxy, carboxy, nitro, cyano, alkyl, aryl, cycloalkyl, cycloalkenyl, heteroaryl, heterocyclyl);
substituted or unsubstituted alkyloxycarbonyl (when substituted, substituents include halogen, hydroxy, carboxy, nitro, cyano, alkyl, aryl, cycloalkyl, cycloalkenyl, heteroaryl, heterocyclyl. e.g., methoxycarbonyl, ethoxycarbonyl, tert-butoxycarbonyl);
substituted or unsubstituted aryloxycarbonyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkyloxycarbonyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkenyloxycarbonyl (when substituted, substituents include halogen, hydroxy, carboxy, nitro, cyano, alkyl, aryl, cycloalkyl, cycloalkenyl, heteroaryl, heterocyclyl);
substituted or unsubstituted heteroaryloxycarbonyl (when substituted, substituents include halogen, hydroxy, carboxy, nitro, cyano, alkyl, aryl, cycloalkyl, cycloalkenyl, heteroaryl, heterocyclyl);
substituted or unsubstituted heterocyclyloxycarbonyl (when substituted, substituents include halogen, hydroxy, carboxy, nitro, cyano, alkyl, aryl, cycloalkyl, cycloalkenyl, heteroaryl, heterocyclyl);
substituted or unsubstituted sulfamoyl (when substituted, substituents include halogen, hydroxy, carboxy, nitro, cyano, alkyl, aryl, cycloalkyl, cycloalkenyl, heteroaryl, heterocyclyl);
substituted or unsubstituted alkylsulfonyl (when substituted, substituents include halogen, hydroxy, carboxy, nitro, cyano, alkyl, aryl, cycloalkyl, cycloalkenyl, heteroaryl, heterocyclyl. e.g., methanesulfonyl, ethanesulfonyl);
substituted or unsubstituted arylsulfonyl (when substituted, substituents include halogen, hydroxy, carboxy, nitro, cyano, alkyl, aryl, cycloalkyl, cycloalkenyl, heteroaryl, heterocyclyl);
substituted or unsubstituted heteroarylsulfonyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkylsulfonyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkenylsulfonyl (when substituted, substituents include halogen, hydroxy, carboxy, nitro, cyano, alkyl, aryl, cycloalkyl, cycloalkenyl, heteroaryl, heterocyclyl);
substituted or unsubstituted heterocyclylsulfonyl (when substituted, substituents include halogen, hydroxy, carboxy, nitro, cyano, alkyl, aryl, cycloalkyl, cycloalkenyl, heteroaryl, heterocyclyl);

substituted or unsubstituted carbamoyl (when substituted, substituents include halogen, hydroxy, carboxy, nitro, cyano, alkyl, aryl, cycloalkyl, cycloalkenyl, heteroaryl, heterocyclyl);
substituted or unsubstituted alkylsulfinyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkylsulfinyl (when substituted, substituents include halogen, hydroxy, carboxy, nitro, cyano, alkyl, aryl, cycloalkyl, cycloalkenyl, heteroaryl, heterocyclyl);
substituted or unsubstituted cycloalkenylsulfinyl (when substituted, substituents include halogen, hydroxy, carboxy, nitro, cyano, alkyl, aryl, cycloalkyl, cycloalkenyl, heteroaryl, heterocyclyl);
substituted or unsubstituted arylsulfinyl (when substituted, substituents include halogen, hydroxy, carboxy, nitro, cyano, alkyl, aryl, cycloalkyl, cycloalkenyl, heteroaryl, heterocyclyl);
substituted or unsubstituted heteroarylsulfinyl (when substituted, substituents include halogen, hydroxy, carboxy, nitro, cyano, alkyl, aryl, cycloalkyl, cycloalkenyl, heteroaryl, heterocyclyl);
substituted or unsubstituted heterocyclylsulfinyl (when substituted, substituents include halogen, hydroxy, carboxy, nitro, cyano, alkyl, aryl, cycloalkyl, cycloalkenyl, heteroaryl, heterocyclyl);
halogen; hydroxy; carboxy; nitro; cyano; amino; and the like.

The alkyl parts of "arylalkyl", "alkylamino", "arylalkylamino", "alkyloxycarbonylamino", "alkylsulfonylamino", "heteroarylalkylcarbamoyl", "alkylthio" and "alkylsulfinyl" mean the above-described "alkyl".

The alkenyl part of "alkenyloxy" means the above-described "alkenyl".

The aryl parts of "arylalkyl", "arylamino", "arylalkylamino", "arylsulfonylamino" and "arylsulfinyl" mean the above-described "aryl".

The heteroaryl parts of "heteroarylamino", "heteroarylsulfonylamino", "heteroarylalkylcarbamoyl", "heteroaryloxycarbonyl" and "heteroarylsulfinyl" mean the above-described "heteroaryl".

The cycloalkyl parts of "cycloalkylamino", "cycloalkylsulfonylamino", "cycloalkyloxycarbonyl" and "cycloalkylsulfinyl" mean the above-described "cycloalkyl".

The cycloalkenyl parts of "cycloalkenylamino", "cycloalkenylsulfonylamino", "cycloalkenyloxycarbonyl" and "cycloalkenylsulfinyl" mean the above-described "cycloalkenyl".

The heterocyclyl parts of "heterocyclylamino", "heterocyclylsulfonylamino", "heterocyclyloxycarbonyl" and "heterocyclylsulfinyl" mean the above-described "heterocyclyl".

Among the compounds of the present invention, the compounds in the following embodiments are preferred.

$R^1$ is hydrogen, or substituted or unsubstituted alkyl. Preferably, $R^1$ is hydrogen.

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Further preferably, $R^2$ is aryl, heteroaryl, cycloalkyl, cycloalkenyl or heterocyclyl substituted with at least one group selected from halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

Particularly preferably, $R^2$ is aryl, heteroaryl, cycloalkyl, cycloalkenyl or heterocyclyl substituted with at least one halogen,
and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

Most preferably, $R^2$ is cycloalkyl or heterocyclyl substituted with at least one halogen,
and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

Examples of preferred embodiments of $R^2$ include the following rings.

[Chemical formula 20]

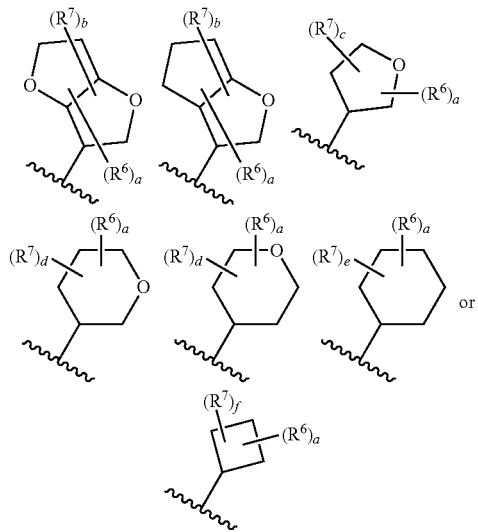

wherein $R^6$, $R^7$, a, b, c, d, e and f are as defined above.

Examples of further preferred embodiments of $R^2$ include the following rings.

[Chemical formula 21]

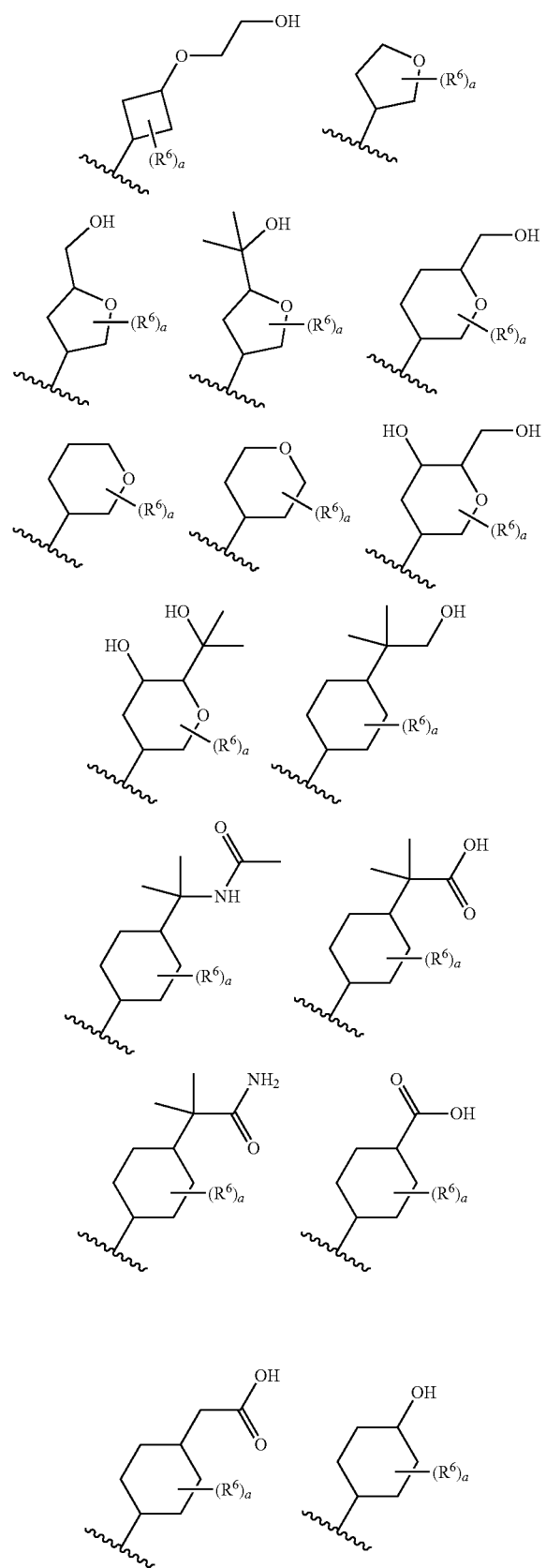

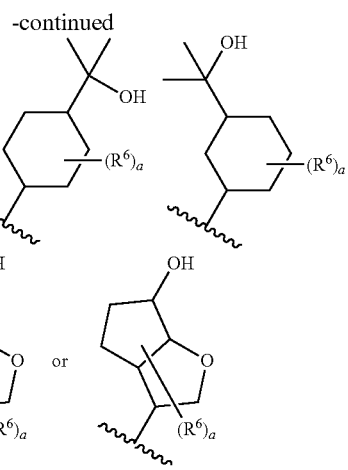

wherein $R^6$ and a are as defined above.

Embodiments in which $R^2$ is substituted or unsubstituted cycloalkyl, or substituted or unsubstituted heterocyclyl, and $R^3$ is fluoro, cyano, substituted or unsubstituted alkyl, or substituted or unsubstituted alkyloxy are also preferred.

Further preferably, embodiments in which $R^2$ is

[Chemical formula 22]

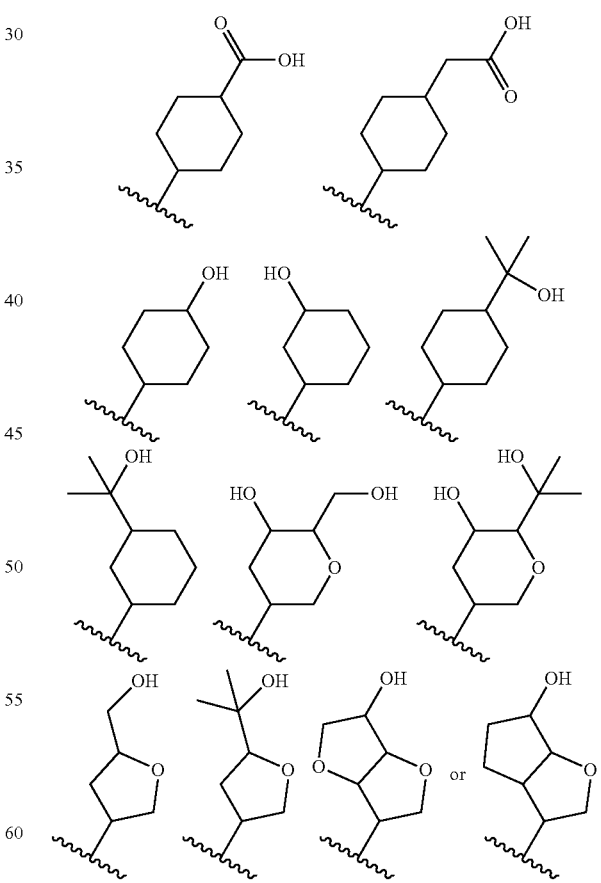

and $R^3$ is fluoro, cyano, substituted or unsubstituted alkyl, or substituted or unsubstituted alkyloxy are also preferred.

$R^6$ is each independently halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, or substituted or unsubstituted amino.

Preferably, $R^6$ is halogen.

a is an integer from 1 to 3. Preferably, a is 1 or 2.

$R^7$ is each independently hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

Preferably, $R^7$ is each independently hydroxy, carboxy, substituted or unsubstituted alkyl, or substituted or unsubstituted alkyloxy.

b is an integer from 0 to 8. Preferably, b is an integer of 0 to 3. Further preferably, b is 1 or 2. Particularly preferably, b is 1.

c is an integer from 0 to 6. Preferably, c is an integer of 0 to 3. Further preferably, c is 1 or 2. Particularly preferably, c is 1.

d is an integer from 0 to 8. Preferably, d is an integer of 0 to 3. Further preferably, d is an integer of 0 to 2.

e is an integer from 0 to 10. Preferably, e is an integer of 0 to 3. Further preferably, e is 1.

f is an integer from 0 to 6. Preferably, f is an integer of 0 to 3. Further preferably, f is 1.

T is $-CR^5=$ or $-N=$. Preferably, T is $-N=$.

X is a single bond, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, X is a single bond, substituted or unsubstituted aryl, substituted or unsubstituted heteroaryl, or substituted or unsubstituted heterocyclyl.

Further preferably, X is substituted or unsubstituted aryl or substituted or unsubstituted heteroaryl.

Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, Y is substituted or unsubstituted aryl, substituted or unsubstituted heteroaryl, substituted or unsubstituted cycloalkenyl, or substituted or unsubstituted heterocyclyl.

Further preferably, Y is substituted or unsubstituted aryl, substituted or unsubstituted cycloalkenyl, or substituted or unsubstituted heterocyclyl.

Particularly preferably, Y is substituted or unsubstituted aryl, or substituted or unsubstituted heteroaryl.

Z is $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^{S''})-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^NR^{N'}N)(O=)S=N-R^{2f}-$, $(R^{N''})N=S(=O)(NR^NR^{N'})-$, $(R^{N''})N=S(=O)(NR^NR^{N'})-R^{2f}-$, $R^{P1}R^{P2}(O=)P-$,

[Chemical formula 23]

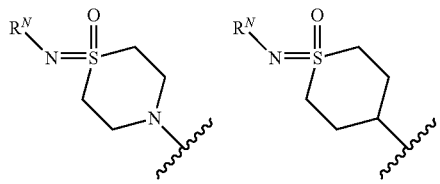

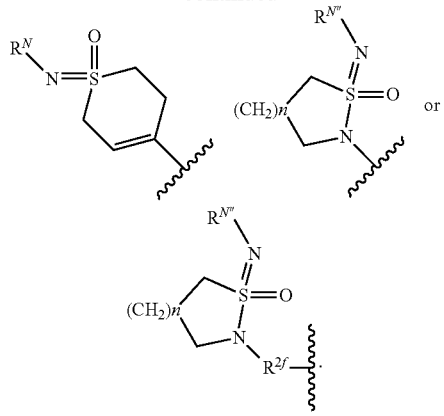

Preferably, Z is $R^SR^{S'}(O=)S=N-$, $(R^N)N=S(=O)(R^S)-$, $((R^N)N=)_2S(R^{S''})-$, $R^OO-C(=O)-N(R^N)-$, or $R^S(R^NR^{N'}N)(O=)S=N-$.

n is an integer 1 or 2.

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl; and $R^S$ and $R^{S'}$ which are bound to the same sulfur atom may form a substituted or unsubstituted ring together with the sulfur atom.

Preferably, $R^S$ and $R^{S'}$ are each independently substituted or unsubstituted alkyl.

The ring, which is formed by $R^S$ and $R^{S'}$ which are bound to the same sulfur atom, together with the sulfur atom, means a 3 to 15-membered saturated or unsaturated hetero ring that may contain one to four oxygen, nitrogen and/or sulfur atom(s) in the ring, other than the sulfur atom. Preferred is a non aromatic ring, and such non aromatic ring may be further cross-linked by a C1 to C4 alkyl chain, and may be fused with cycloalkane (preferably 5 to 6-membered) and a benzene ring. Examples thereof include as follows.

[Chemical formula 24]

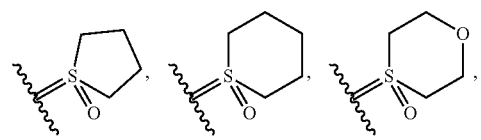

$R^{S''}$ is hydrogen, substituted or unsubstituted alkyl, substituted or unsubstituted cycloalkyl, substituted or unsubstituted heterocyclyl, substituted or unsubstituted aryl, or substituted or unsubstituted heteroaryl.

Preferably, $R^{S''}$ is substituted or unsubstituted alkyl.

$R^{2f}$ is substituted or unsubstituted alkylene.

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl; and two $(R^N)N=$ which are bound to the same sulfur atom may form a substituted or unsubstituted ring together with the sulfur atom when Z is $((R^N)N=)_2S(R^{S''})—$.

Preferably, $R^N$ is each independently hydrogen, substituted or unsubstituted alkyl, or substituted or unsubstituted carbamoyl.

Further preferably, $R^N$ is each independently hydrogen, or substituted or unsubstituted alkyl.

Examples of the ring formed by two $(R^N)N=$ which are bound to the same sulfur atom together with the sulfur atom, when Z is $((R^N)N=)_2S(R^{S''})—$, include as follows.

[Chemical formula 25]

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl; $R^N$ and $R^{N'}$ which are bound to the same nitrogen atom may form a substituted or unsubstituted ring together with the nitrogen atom.

Preferably, $R^{N'}$ is hydrogen, cyano, substituted or unsubstituted alkyl, substituted or unsubstituted cycloalkyl, substituted or unsubstituted aryl, or substituted or unsubstituted heteroaryl.

Further preferably, $R^{N'}$ is hydrogen, or substituted or unsubstituted alkyl.

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl.

Preferably, $R^{N''}$ is hydrogen, or substituted or unsubstituted alkyl.

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, $R^O$ is substituted or unsubstituted alkyl.

$R^{P1}$ and $R^{P2}$ are each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, $R^{P1}$ is substituted or unsubstituted alkyl.
Preferably, $R^{P2}$ is substituted or unsubstituted alkyl.

$R^3$, $R^4$ and $R^5$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

$R^3$ is preferably halogen, cyano, substituted or unsubstituted alkyl, or substituted or unsubstituted alkyloxy.

Further preferably, $R^3$ is fluoro, chloro, cyano or substituted or unsubstituted alkyl, and the substituent of the substituted alkyl is halogen.

Particularly preferably, $R^3$ is fluoro or chloro.
Preferably, $R^4$ is hydrogen.
Preferably, $R^5$ is hydrogen.

Preferred combinations of substituents of a compound represented by formula (I) include the following 1) to 6):

1)
a compound wherein $R^1$ is hydrogen,
$R^2$ is aryl, heteroaryl, cycloalkyl, cycloalkenyl or heterocyclyl substituted with at least one group selected from halogen, $—PO(OH)_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino,
T is $—N=$,
X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl,
Z is $R^S R^{S'}(O=)S=N—$, $(R^N)N=S(=O)(R^S)—$, $((R^N)N=)_2 S(R^{S''})—$, $R^O O—C(=O)—N(R^N)—$, or $R^S(R^N R^{N'}N)(O=)S=N—$,
$R^3$ is halogen, cyano, substituted or unsubstituted alkyl, or substituted or unsubstituted alkyloxy, and
$R^4$ is hydrogen.

2)
a compound wherein $R^1$ is hydrogen,
$R^2$ is aryl, heteroaryl, cycloalkyl, cycloalkenyl or heterocyclyl substituted with at least one halogen,
T is $—N=$,
X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl, Z is $R^SR^{S'}(O=)S=N-$, $(R^N)N=S(=O)(R^S)-$, $((R^N)N=)_2 S(R^{S''})-$, $R^OO-C(=O)-N(R^N)-$, or $R^S(R^NR^{N'}N)(O=)S=N-$, $R^3$ is halogen, cyano, substituted or unsubstituted alkyl, or substituted or unsubstituted alkyloxy, and $R^4$ is hydrogen.

3)
a compound wherein $R^1$ is hydrogen, $R^2$ is cycloalkyl or heterocyclyl substituted with at least one group selected from halogen, $-PO(OH)_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, T is $-N=$, X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl, Z is $R^SR^{S'}(O=)S=N-$, $(R^N)N=S(=O)(R^S)-$, $((R^N)N=)_2 S(R^{S''})-$, $R^OO-C(=O)-N(R^N)-$, or $R^S(R^NR^{N'}N)(O=)S=N-$, $R^3$ is halogen, cyano, substituted or unsubstituted alkyl, or substituted or unsubstituted alkyloxy, and $R^4$ is hydrogen.

4)
a compound wherein $R^1$ is hydrogen, $R^2$ is cycloalkyl or heterocyclyl substituted with at least one halogen, T is $-N=$, X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl, Z is $R^SR^{S'}(O=)S=N-$, $(R^N)N=S(=O)(R^S)-$, $((R^N)N=)_2 S(R^{S''})-$, $R^OO-C(=O)-N(R^N)-$, or $R^S(R^NR^{N'}N)(O=)S=N-$, $R^3$ is halogen, cyano, substituted or unsubstituted alkyl, or substituted or unsubstituted alkyloxy, and $R^4$ is hydrogen.

5)
a compound wherein $R^1$ is hydrogen, $R^2$ is substituted or unsubstituted cycloalkyl, or substituted or unsubstituted heterocyclyl, T is $-N=$, X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl, Z is $R^SR^{S'}(O=)S=N-$, $(R^N)N=S(=O)(R^S)-$, $((R^N)N=)_2 S(R^{S''})-$, $R^OO-C(=O)-N(R^N)-$, or $R^S(R^NR^{N'}N)(O=)S=N-$, $R^3$ is fluoro, cyano, substituted or unsubstituted alkyl, or substituted or unsubstituted alkyloxy, and $R^4$ is hydrogen.

6)
a compound wherein $R^1$ is hydrogen, $R^2$ is substituted or unsubstituted cycloalkyl, or substituted or unsubstituted heterocyclyl, T is $-N=$, X is a single bond, substituted or unsubstituted aryl, substituted or unsubstituted heteroaryl, or substituted or unsubstituted heterocyclyl, Y is substituted or unsubstituted aryl, substituted or unsubstituted heteroaryl, substituted or unsubstituted cycloalkenyl, or substituted or unsubstituted heterocyclyl, Z is $R^SR^{S'}(O=)S=N-$, $(R^N)N=S(=O)(R^S)-$, $((R^N)N=)_2 S(R^{S''})-$, $R^OO-C(=O)-N(R^N)-$, or $R^S(R^NR^{N'}N)(O=)S=N-$, $R^3$ is fluoro, and $R^4$ is hydrogen.

One or more hydrogen, carbon or other atoms of the compounds of formula (I) of the present invention can be replaced by an isotope of the hydrogen, carbon or other atoms.

For example, the compounds of formula (I) include all radiolabeled forms of compounds of formula (I). Such "radioactive labeling," "radiolabeled form" and the like of the compounds of formula (I) are encompassed by the present invention and useful as a research and/or diagnostic tool in metabolism pharmacokinetic studies and in binding assays. Examples of isotopes that can be incorporated into a compound of formula (I) of the present invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Radiolabeled compounds of the present invention can be prepared by methods well-known in the art. For example, tritium-labeled compounds of formula (I) can be prepared by introducing tritium into a particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

As a pharmaceutically acceptable salt of the compound of the present invention, the following salts can be included.

As a basic salt, examples include alkali metal salts such as sodium salts and potassium salts; alkaline earth metal salts such as calcium salts and strontium salts; beryllium salts, magnesium salts; transition metal salts such as zinc salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts and ethylenediamine salts; aralkylamine salts such as N,N-dibenzylethylenediamine and benethamine salts; heterocyclic aromatic amine salts such as pyridine salts, picoline salts, quinoline salts, and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts, and tetrabutylammonium salts; basic amino acid salts such as arginine salts and lysine salts; and the like.

As an acidic salt, examples include inorganic acid salts such as hydrochlorides, sulfates, nitrates, phosphates, carbonates, hydrogencarbonates, and perchlorates; organic acid salts such as acetates, propionates, lactates, maleates, fumarates, tartrates, malates, citrates and ascorbates; sulfonate salts such as methane sulfonates, isethionates, benzenesulfonates and p-toluenesulfonates; acidic amino acid salts such as aspartates and glutamates; and the like.

A compound represented by formula (I) of the present invention or its pharmaceutically acceptable salt may form a solvate (e.g., hydrate, etc.), cocrystal and/or a crystal polymorph, and the present invention also contains such various types of solvates, cocrystal and crystal polymorphs. In a "solvate", any number of solvent molecules (e.g., water molecule, etc.) may be coordinated with a compound represented by formula (I). When left in the atmosphere, a compound represented by formula (I) or its pharmaceutically acceptable salt may absorb water, and a case where adsorbed water is attached thereto or a case where hydrate is formed may arise. In addition, by recrystallization of a compound represented by formula (I) or its pharmaceutically acceptable salt, a crystal polymorph thereof can be formed. The "cocrystal" means that a compound represented by formula (I) or its salt and a counter molecule are present in the same crystal lattice, and may be formed with any number of counter molecule.

A compound represented by formula (I) of the present invention or its pharmaceutically acceptable salt may form a prodrug, and the present invention also contains such various types of prodrugs. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I) by enzymatic oxidation, reduction, hydrolysis and the like in living organisms under physiological conditions; a compound which is converted into a compound represented by formula (I) by hydrolysis by e.g., gastric acid; and the like. A method for selecting and a method for producing a proper prodrug derivative are described in e.g., Design of Prodrugs, Elsevier, Amsterdam 1985. Prodrugs can have activity in themselves.

When a compound represented by formula (I) or its pharmaceutically acceptable salt has a hydroxyl group, prodrugs such as acyloxy derivatives and sulfonyloxy derivatives are exemplified, which derivatives are produced, for example, by a reaction of a compound having a hydroxyl group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, $p\text{-}CH_3O\text{-}PhSO_3-$, $PhSO_3-$ and $p\text{-}CH_3PhSO_3-$.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatments which are carried out in common experiments in organic chemistry may be carried out.

A compound represented by formula (I-1) can be synthesized as follows.

[Chemical formula 26]

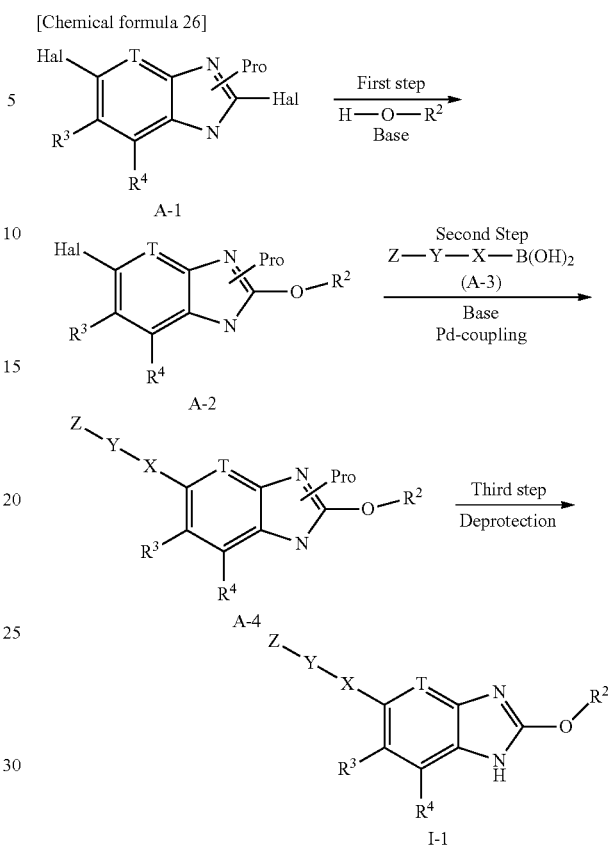

wherein each symbol has the same meaning as above, and as a compound represented by formula (A-1), a known compound can be used, or a compound which is derived from a known compound by a conventional method may be used. "Hal" means a halogen, and Pro means a protecting group. Pro includes a benzyl group, a p-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl) and the like.

First Step

The first step is a step in which a compound represented by formula (A-2) is produced by reacting a compound represented by formula (A-1) and a compound represented by formula: $H-O-R^2$.

As a reaction solvent, examples include N,N-dimethylformamide, dimethyl sulfoxide, aromatic hydrocarbons (e.g., toluene, benzene, xylene, etc.), saturated hydrocarbons (e.g., cyclohexane, hexane, etc.), halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), ketones (e.g., acetone, methyl ethyl ketone, etc.), nitriles (e.g., acetonitrile, etc.), alcohols (e.g., methanol, ethanol, t-butanol, etc.), water, a mixed solvent thereof and the like.

Preferred examples include N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.) and the like.

As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi) and the like.

Preferred examples include metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi) and the like.

Further preferably, metal hydrides (e.g., sodium hydride, etc.) or metal carbonates (e.g., sodium carbonate, calcium carbonate, cesium carbonate, etc.) can be used.

The reaction can be carried out at 0 to 100° C. for 0.5 to 12 hours.
(When Hal which is bound to an imidazole ring is bromine or iodine)

The reaction can be carried out using conditions for a reaction which is known as the Ullmann reaction.

As a reaction solvent, the above solvents can be used. Preferred examples include N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.) and the like.

As a base, the above bases can be used. Preferred examples include metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi) and the like.

Further preferably, metal carbonates (e.g., sodium carbonate, calcium carbonate, cesium carbonate, etc.) can be used.

As a catalyst, copper iodide can be used.

The reaction can be carried out at room temperature to 100° C. for 0.5 to 12 hours.

Second Step

The second step is a step in which a compound represented by formula (A-4) is produced by reacting a compound represented by formula (A-2) and a compound represented by formula (A-3) in the presence of a palladium catalyst. As a compound represented by formula (A-3), boronic acid ester may be used.

As a solvent, solvents described for the first step can be used. Preferably, N,N-dimethylformamide, aromatic hydrocarbons (e.g., toluene, benzene, xylene, etc.), ethers (e.g., tetrahydrofuran, diethyl ether, dioxane, 1,2-dimethoxyethane, etc.) or alcohols (e.g., methanol, ethanol, t-butanol, etc.) can be used.

As a base, bases described for the first step can be used. Preferably, metal carbonates (e.g., sodium carbonate, calcium carbonate, cesium carbonate, etc.) or organic amines (e.g., triethylamine, diisopropylethylamine, DBU, 2,6-lutidine, etc.) can be used.

The reaction may be carried out in the presence of a palladium catalyst (e.g., Pd(PPh$_3$)$_4$, PdCl$_2$, Pd(OAc)$_2$, Pd(dba)$_2$, etc.) and a phosphine ligand (e.g., PPh$_3$, BINAP, etc.) at a temperature, at which a solvent to be used is refluxed, for 0.5 to 12 hours.

When using microwave, the reaction can be carried out at 80 to 200° C. for 5 minutes to one hour.

Third Step

The third step is a step in which a compound represented by formula (I-1) is produced by deprotection of a compound represented by formula (A-4).

As a reaction solvent, solvents described for the first step can be used. Preferred examples include N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), alcohols (e.g., methanol, ethanol, t-butanol, etc.) and the like.

The reaction can be carried out in the presence of hydrochloric acid, TFA (trifluoroacetic acid), TBAF (tetrabutylammoniumfluoride) or the like at 0 to 100° C. for 0.5 to 24 hours.

Among compounds represented by formula (I), a compound, wherein $R^1$ is substituted or unsubstituted alkyl, can be synthesized, for example, from a compound represented by formula (I-1) by an alkylation reaction using sodium hydride and an alkyl halide.

Among compounds represented by formula (I), the substituents $R^3$ and $R^4$ can be introduced in any step of the above-described first to third steps.

Various types of substituents on compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS and the like.

A compound of the present invention has an excellent AMPK activating effect. Therefore, the compound can be used for the treatment or prevention of diseases associated with AMPK, particularly disease such as type I diabetes, type II diabetes, hyperglycemia, metabolic syndrome, obesity, hypercholesterolemia and/or hypertension. Particularly, the compound is useful in the treatment or prevention of type II diabetes, hyperglycemia, metabolic syndrome or obesity.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In the case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

A compound of the present invention can be used in combination with an insulin secretagogue (e.g., a sulfonylurea (SU) drug), a fast-acting insulin secretagogue (e.g., a phenylalanine derivative), a glucose uptake inhibitor (e.g., an α-glucosidase inhibitor (α-GI drug)), an insulin resistance improving drug (e.g., a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulations comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is described in more detail below with reference to Examples, which are not intended to limit the scope of the present invention.

NMR spectrum data of the compounds of the present invention and intermediates thereof are shown. NMR analysis obtained in each example was performed at 400 MHz using deuterated chloroform ($CDCl_3$) or dimethyl sulfoxide (d6-DMSO).

LC/MS was measured under the following conditions.

(Method A)
Column: ACQUITY UPLC BEH C18 (1.7 μm i.d. 2.1×50 mm) (Waters)
Flow rate: 0.8 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 5 to 100% was carried out for 3.5 minutes, and the solvent [B] at 100% was maintained for 0.5 minutes.

(Method B)
Column: Shim-pack XR-ODS (2.2 μm, i.d. 3.0×50 mm) (Shimadzu)
Flow rate: 1.6 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3 minutes, and the solvent [B] at 100% was maintained for 0.5 minutes.

(Method C)
Column: ACQUITY UPLC BEH C18 (1.7 μm i.d. 2.1×50 mm) (Waters)
Flow rate: 0.55 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 5 to 100% was carried out for 3 minutes, and the solvent [B] at 100% was maintained for 0.5 minutes.

The meaning of each term in Examples is as follows.
TBAF: Tetrabutylammonium fluoride
THF: Tetrahydrofuran
$PdCl_2$(dtbpf): [1,1'-Bis(di-tert-butylphosphino)ferrocene]palladium(II) dichloride
TFA: Trifluoroacetic acid
DMF: N,N-Dimethylformamide
PPTS: Pyridinium p-toluenesulfonate
SEM: Trimethylsilylethoxymethyl
TBS: tert-Butyldimethylsilyl
THP: Tetrahydropyran
Pd($PPh_3$)$_4$: Tetrakis(triphenylphosphine)palladium(0)
DIAD: Diisopropyl azodicarboxylate
DMAP: N,N-Dimethyl-4-aminopyridine
$PdCl_2$(dppf)$CH_2Cl_2$: [1,1'-Bis(diphenylphosphino)ferrocene]palladium(II) dichloride dichloromethane adduct
DMSO: Dimethyl sulfoxide
DIBAL-H: Diisobutylaluminium hydride
TBDPS: tert-Butyldiphenylsilyl
DAST: (Diethylamino)sulfur trifluoride
Pd($PPh_3$)$_4$: Tetrakis(triphenylphosphine)palladium(0)
Bn: Benzyl
$Pd_2$(dba)$_3$: Tris(dibenzylideneacetone)dipalladium(0)
Xantphos: 4,5'-Bis(diphenylphosphino)-9,9'-dimethylxanthene

Example 1

[Chemical formula 27]

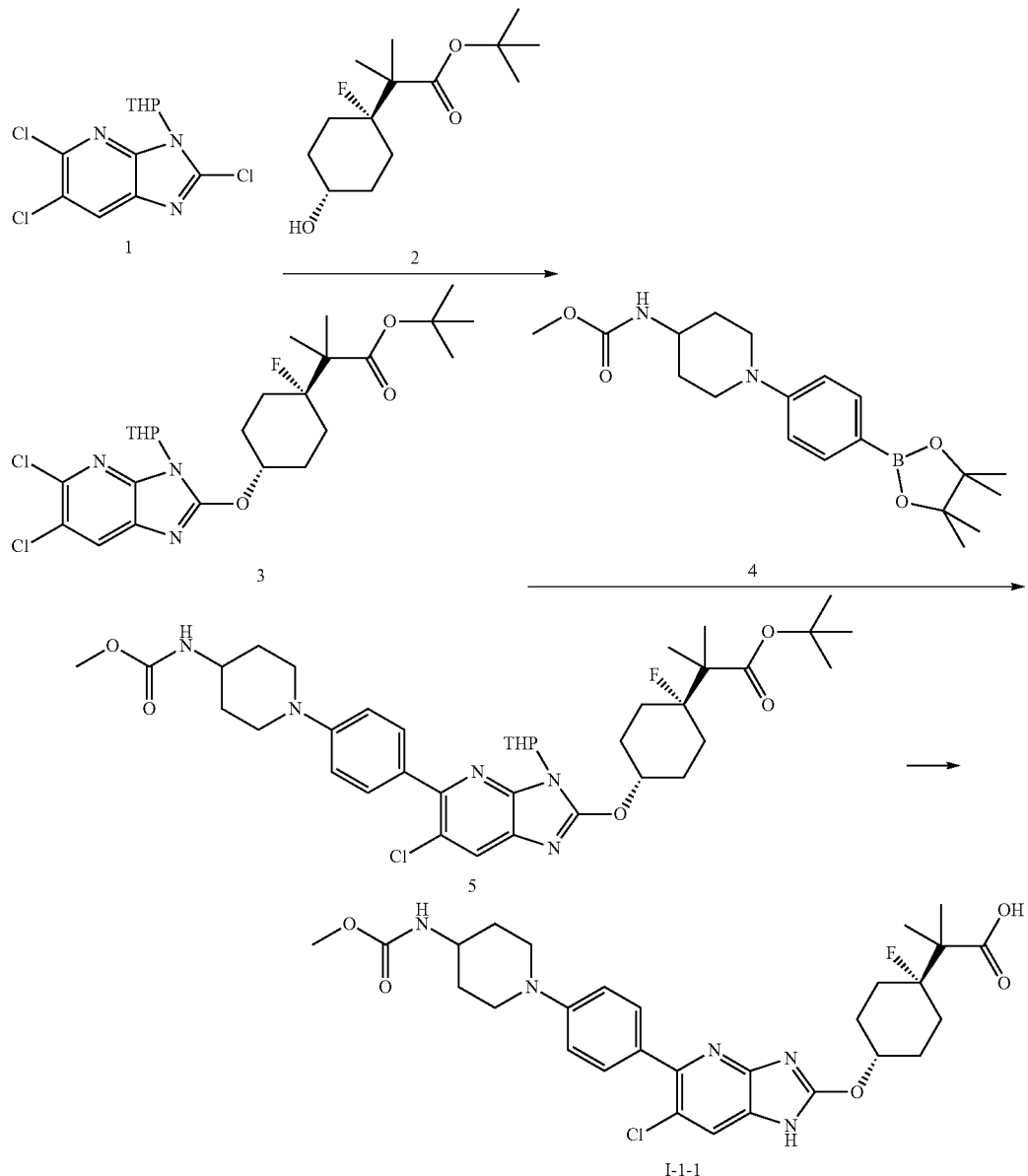

A solution of Compound 1 (200 mg, 0.652 mmol) and Compound 2 (187 mg, 0.718 mmol) in THF (2 mL) was cooled in ice bath, and potassium t-butoxide (88 mg, 0.783 mmol) was added thereto, then the mixture was stirred under ice-cooling. After completion of the reaction, ethyl acetate and a saturated aqueous solution of ammonium chloride were added thereto, and a liquid-liquid separation was performed. The obtained organic layer was concentrated under reduced pressure, and purified by silica gel column chromatography to obtain Compound 3. To a solution of Compound 3 (75 mg, 0.141 mmol) and Compound 4 (61.1 mg, 0.170 mmol) in 1,4-dioxane (0.75 mL) were added PdCl$_2$(dtbpf) (18.4 mg, 0.028 mmol) and a 2 mol/L aqueous solution of potassium carbonate (141 μL, 0.283 mmol), and the mixture was stirred under microwave irradiation at 130° C. The obtained reaction mixture was purified by silica gel column chromatography to obtain Compound 5.
Compound 5; Method B
LC/MS retention time=3.11 min.
MS (ESI) m/z=728.55 (M+H)+.

To Compound 5 (26 mg, 0.036 mmol) was added TFA (1.5 mL), and the mixture was stirred at room temperature. After completion of the reaction, TFA was removed under reduced pressure, and methanol was added to the residue. The mixture was neutralized with a 2 mol/L aqueous solution of sodium hydroxide and made weak-acidic with a 2 mol/L aqueous solution of hydrochloric acid, then extracted with a mixed solvent of chloroform and methanol. The obtained organic layer was concentrated under reduced pressure, and purified by silica gel column chromatography to obtain Compound (I-1-1) (16.1 mg, 76.7%).
Compound (I-1-1); Method B
LC/MS retention time=1.75 min.
MS (ESI) m/z=588.55 (M+H)+.

Example 2

Compound 8 was synthesized from Compounds 6 and 7, in a similar way that Compound 3 was synthesized from Compounds 1 and 2. Compound 10 was synthesized from Compounds 8 and 9, in a similar way that Compound 5 was synthesized from Compounds 3 and 4. To Compound 10 (110 mg, 0.143 mmol) was added TFA (2 mL), and the mixture was stirred at room temperature. After completion of the reaction, TFA was removed under reduced pressure,

[Chemical formula 28]

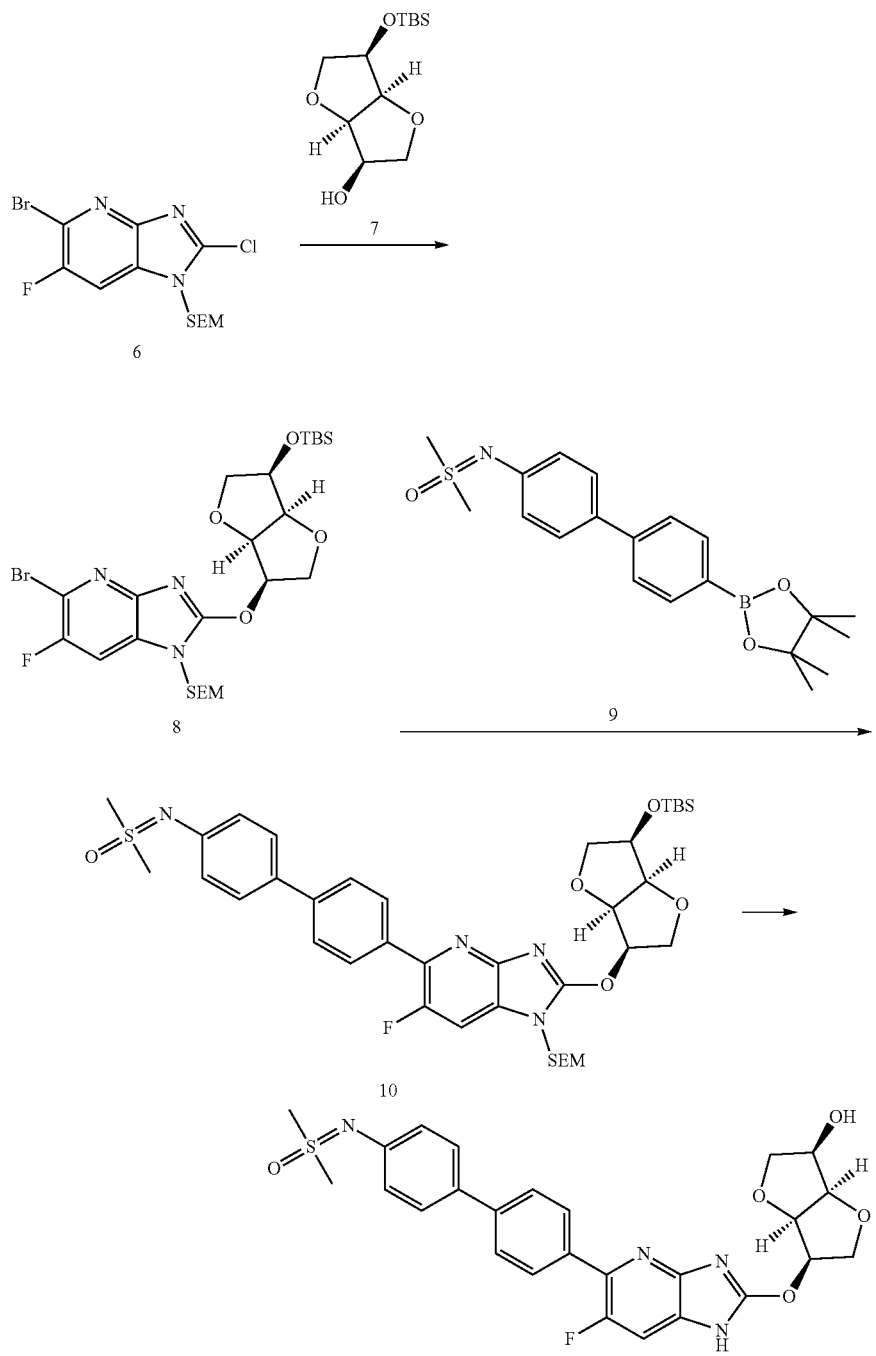

and a mixed solvent of chloroform and methanol was added to the residue. The mixture was neutralized with a 2 mol/L aqueous solution of potassium carbonate, and a liquid-liquid separation was performed. The obtained organic layer was concentrated under reduced pressure, and purified by silica gel column chromatography and reverse-phase column chromatography to obtain Compound (I-1-2) (41.0 mg, 54.6%).

Compound (I-1-2); Method B
LC/MS retention time=1.36 min.
MS (ESI) m/z=525.35 (M+H)+.

Example 3

Compound 12 was synthesized from Compounds 1 and 11, in a similar way that Compound 3 was synthesized from Compounds 1 and 2. Compound 13 was synthesized from Compounds 12 and 9, in a similar way that Compound 5 was synthesized from Compounds 3 and 4. Compound (I-1-3) was synthesized from Compound 13, in a similar way that Compound (I-1-2) was synthesized from Compound 10.

Compound (I-1-3); Method B
LC/MS retention time=1.41 min.
MS (ESI) m/z=457.2 (M+H)+.

[Chemical formula 29]

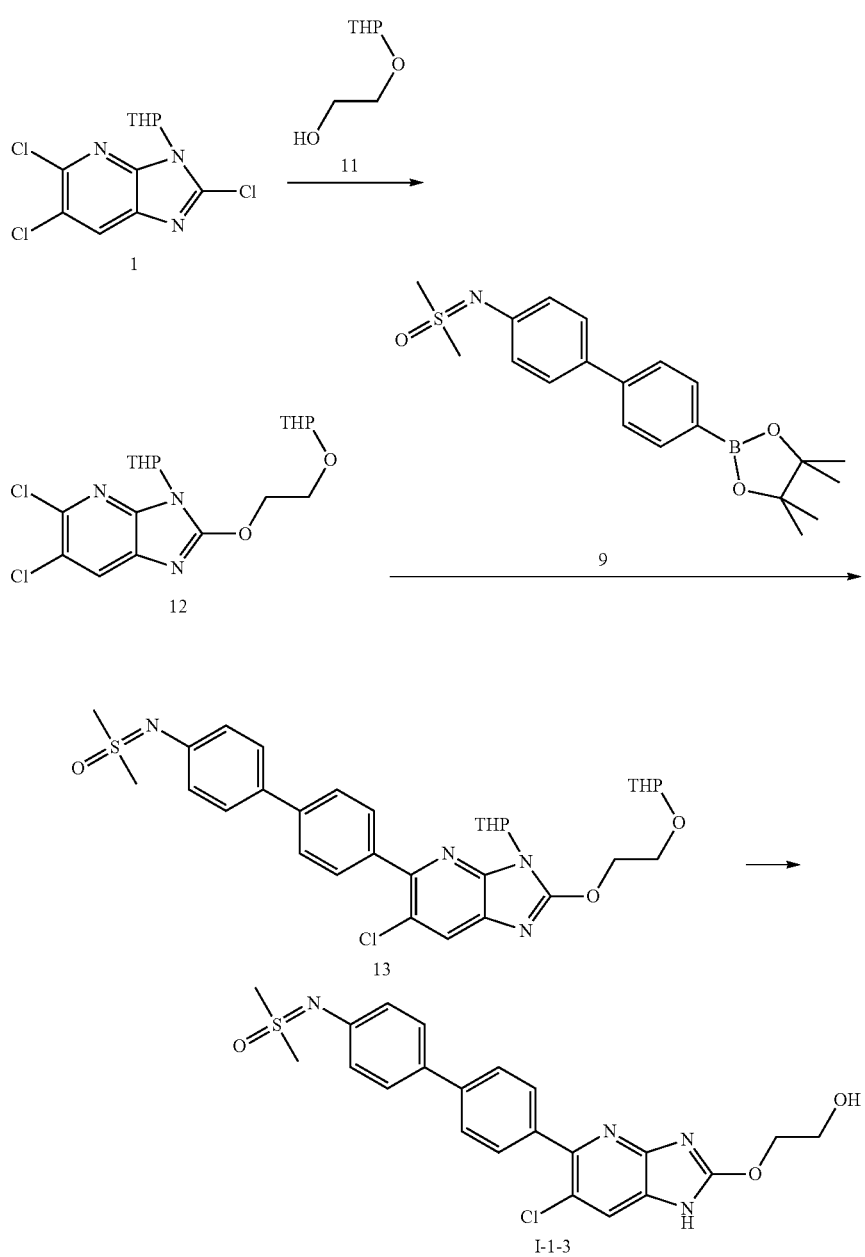

Example 4

[Chemical formula 30]

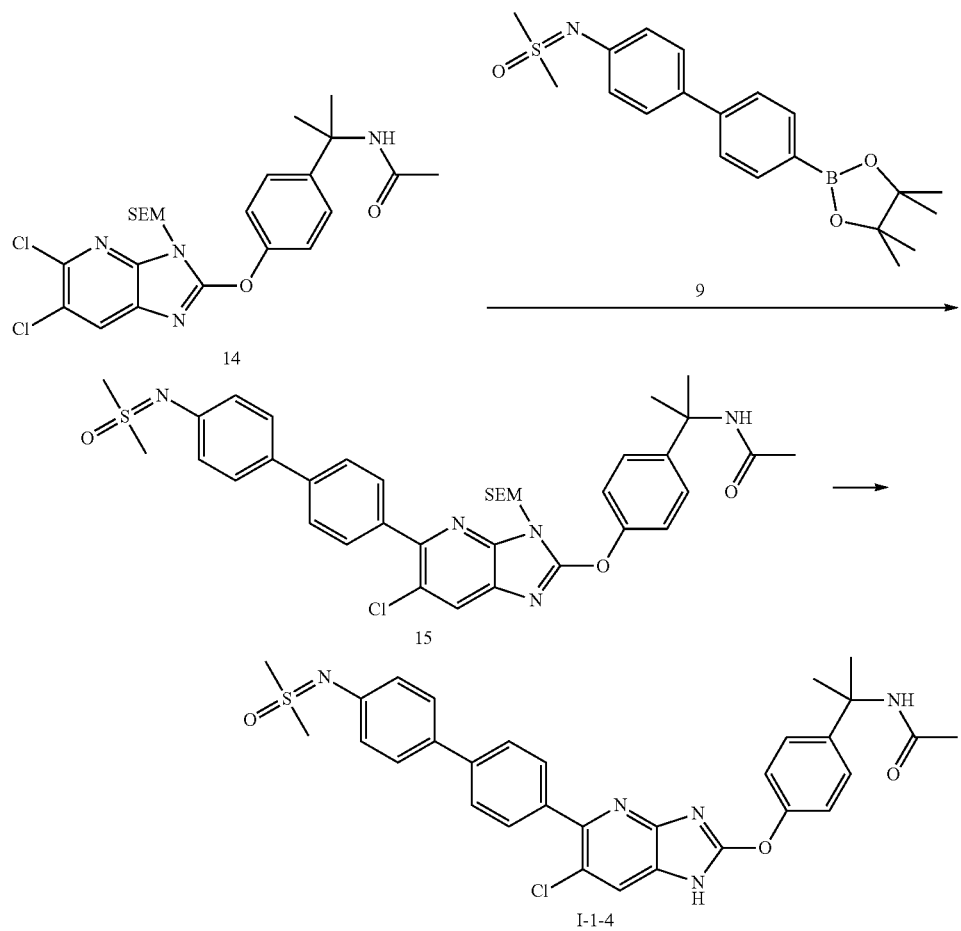

To a solution of Compound 14 (100 mg, 0.196 mmol) and Compound 9 (87 mg, 0.236 mmol) in 1,4-dioxane (0.75 mL) were added Pd(Ph$_3$P)$_4$ (45.4 mg, 0.039 mmol) and a 2 mol/L aqueous solution of potassium carbonate (196 μL, 0.393 mmol), and the mixture was stirred under microwave irradiation at 130° C. The obtained reaction mixture was extracted with chloroform, and concentrated under reduced pressure. The obtained residue was purified by silica gel column chromatography to obtain Compound 15.

Compound 15; Method B
LC/MS retention time=2.52 min.
MS (ESI) m/z=718.40 (M+H)+.

Compound (I-1-4) was synthesized from Compound 15, in a similar way that Compound (I-1-2) was synthesized from Compound 10.

Compound (I-1-4); Method B
LC/MS retention time=1.76 min.
MS (ESI) m/z=588.35 (M+H)+.

Example 5

[Chemical formula 31]

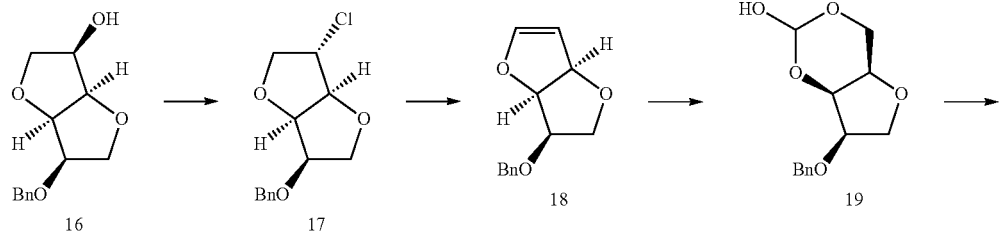

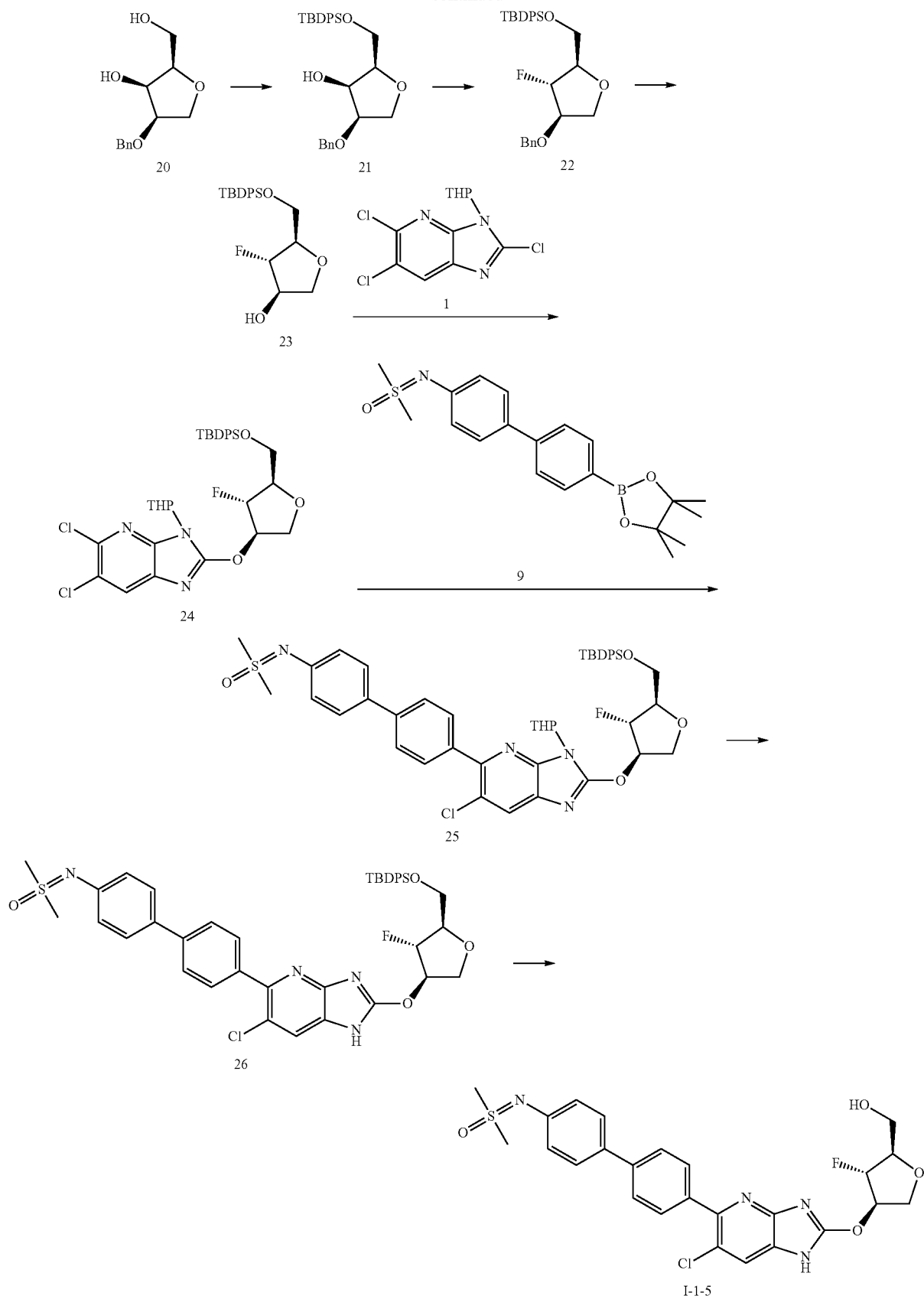

Compound 16 was synthesized by the method described in the following paper. Heterocycles, 2003, vol. 59, #2 p. 793-804

To a solution of Compound 16 (purity of 92.1%, 6.16 g, 5.20 mmol) in acetonitrile (62 mL) were added hexachloroethane (8.52 g, 36.0 mmol), triethylamine (6.66 ml, 48.0 mmol) and triphenylphosphine (1.67 g, 6.35 mmol), and the mixture was stirred at 80° C. for 2 hours. The reaction mixture was concentrated under reduced pressure, then ethyl acetate and water were added to the obtained residue, and a liquid-liquid separation was performed. The organic layer was concentrated under reduced pressure, then ethyl acetate (20 mL) and hexane (20 mL) were added to the obtained residue, and the insoluble material was filtered. The mother liquor was concentrated under reduced pressure, and the obtained residue was purified by silica gel column chromatography to obtain Compound 17 (5.85 g, 95.6%).

Compound 17;
$^1$H-NMR (CDCl$_3$) δ: 3.64 (1H, t, J=8.3 Hz), 3.91 (1H, t, J=8.3 Hz), 4.07-4.15 (1H, m), 4.15 (1H, d, J=11.0 Hz), 4.21 (1H, d, J=10.0 Hz), 4.32 (1H, s), 4.57 (1H, d, J=11.5 Hz), 4.61 (1H, s), 4.78 (1H, d, J=11.5 Hz), 4.80 (1H, s), 7.26-7.40 (6H, m).

To a solution of Compound 17 (772 mg, 3.03 mmol) in DMSO (15 mL) was added potassium t-butoxide (340 mg, 3.03 mmol), and the mixture was stirred at room temperature for 30 minutes. To the reaction mixture was added water, and the mixture was extracted with diethyl ether. The organic layer was concentrated under reduced pressure, and the obtained residue was purified by silica gel column chromatography to obtain Compound 18 (649.3 mg, 98.1%).

Compound 18;
$^1$H-NMR (CDCl$_3$) δ: 3.31 (1H, dd, J=9.8, 8.5 Hz), 3.88 (1H, dd, J=8.5, 6.5 Hz), 4.09 (1H, dt, J=11.0, 5.1 Hz), 4.62 (1H, d, J=11.9 Hz), 4.76 (1H, d, J=11.9 Hz), 4.80 (1H, d, J=5.8 Hz), 5.05 (1H, t, J=2.6 Hz), 5.35 (1H, dd, J=6.3, 2.6 Hz), 6.70 (1H, d, J=2.5 Hz), 7.28-7.42 (5H, m).

To a mixed solution of dichloromethane (121 mL) and methanol (24 mL) of Compound 18 (3.03 g, 13.9 mmol) was added sodium hydrogencarbonate (1.17 g, 13.9 mmol), and the mixture was cooled to −78° C., then ozone gas was passed through. After completion of the reaction, oxygen gas was passed through, and sodium borohydride (1.58 g, 41.6 mmol) was added, then the mixture was stirred under ice-cooling. After completion of the reaction, a 2 mol/L aqueous solution of hydrochloric acid (27 mL) was added thereto, and the mixture was extracted with chloroform. The organic layer was concentrated under reduced pressure, and the obtained residue was purified by silica gel column chromatography to obtain Compound 19 (3.43 g, 97.9%).

Compound 19;
$^1$H-NMR (CDCl$_3$) δ: 3.58-3.65 (1H, m), 3.83-4.21 (7H, m), 4.55-4.62 (2H, m), 4.74 (1H, d, J=12.0 Hz), 7.27-7.42 (5H, m).

A solution of Compound 19 (3.43 g, 13.4 mmol) in dichloroethane (40 mL) was cooled to −78° C., and a 1.03 mol/L DIBAL-H hexane solution (29.6 ml, 30.5 mmol) was added dropwise, then the mixture was stirred at −78° C. After completion of the reaction, water (30 mL) was added, the reaction mixture was diluted with hexane and ethyl acetate, and the precipitate was filtered. The mother liquor was concentrated under reduced pressure, and the obtained residue was purified by silica gel column chromatography to obtain Compound 20 (2.50 g, 80.4%).

Compound 20;
$^1$H-NMR (CDCl$_3$) δ: 2.48 (1H, t, J=6.2 Hz), 3.06 (1H, d, J=6.0 Hz), 3.82 (1H, dd, J=9.7, 5.5 Hz), 3.87 (2H, dd, J=6.2, 4.3 Hz), 3.92 (1H, dd, J=9.7, 4.6 Hz), 3.95 (1H, q, J=4.5 Hz), 4.13 (1H, q, J=5.1 Hz), 4.39 (1H, q, J=5.6 Hz), 4.64 (2H, t, J=12.4 Hz), 7.30-7.41 (5H, m)

A solution of Compound 20 (2.50 g, 11.2 mmol) in dichloromethane (25 mL) was cooled in ice bath, and triethylamine (1.85 mL, 13.4 mmol), DMAP (0.136 g, 1.115 mmol) and tert-butyldiphenylsilyl chloride (3.01 mL, 11.7 mmol) were added thereto, and the mixture was stirred at room temperature. After completion of the reaction, the reaction mixture was concentrated under reduced pressure, then ethyl acetate and water were added thereto, and a liquid-liquid separation was performed. The organic layer was concentrated under reduced pressure, and the obtained residue was purified by silica gel column chromatography to obtain Compound 21 (4.17 g, 80.9%).

Compound 21;
$^1$H-NMR (CDCl$_3$) δ: 1.05 (9H, s), 3.81-3.96 (4H, m), 4.02 (1H, dd, J=10.3, 5.5 Hz), 4.15 (1H, dd, J=11.5, 6.7 Hz), 4.30 (1H, q, J=4.4 Hz), 4.57 (1H, d, J=11.7 Hz), 4.65 (1H, d, J=11.7 Hz), 7.31-7.43 (11H, m), 7.69 (4H, td, J=7.6, 1.4 Hz).

A solution of Compound 21 (88.2 mg, 0.191 mmol) in dichloromethane (12 mL) was cooled to −78° C., and DAST (0.151 ml, 1.14 mmol) was added thereto, then the mixture was stirred at room temperature. After completion of the reaction, sodium hydrogencarbonate and water were added to neutralize the mixture, and the mixture was extracted with ethyl acetate. The organic layer was concentrated under reduced pressure, and the obtained residue was purified by silica gel column chromatography to obtain Compound 22 (48.3 mg, 54.5%).

Compound 22;
$^1$H-NMR (CDCl$_3$) δ: 1.06 (9H, s), 3.75 (1H, dd, J=10.4, 7.5 Hz), 3.81 (1H, ddd, J=10.4, 5.5, 1.8 Hz), 3.94-4.02 (2H, m), 4.07-4.24 (2H, m), 4.51 (1H, d, J=11.8 Hz), 4.57 (1H, d, J=11.8 Hz), 5.17 (1H, dt, J=52.4, 1.7 Hz), 7.26-7.44 (11H, m), 7.64-7.68 (4H, m).

A solution of Compound 22 (59.2 mg, 0.127 mmol) in dichloroethane (2 mL) was cooled to −78° C., and a 1.0 mol/L solution of boron tribromide (0.510 ml, 0.510 mmol) in dichloromethane was added thereto, then the mixture was stirred at −78° C. After completion of the reaction, sodium hydrogencarbonate (161 mg, 1.91 mmol) and water were added to neutralize the mixture, and the mixture was extracted with ethyl acetate. The organic layer was concentrated under reduced pressure, and the obtained residue was purified by silica gel column chromatography to obtain Compound 23 (32.1 mg, 67.3%).

Compound 23;
$^1$H-NMR (CDCl$_3$) δ: 1.06 (10H, s), 3.75 (1H, dd, J=11.3, 1.8 Hz), 3.86 (1H, dd, J=11.3, 2.8 Hz), 3.93-4.02 (2H, m), 4.04-4.15 (2H, m), 4.28 (1H, td, J=11.0, 2.5 Hz), 5.06 (1H, d, J=52.1 Hz), 7.39-7.49 (6H, m), 7.65-7.72 (4H, m).

A solution of Compound 23 (32.1 mg, 0.086 mmol) and Compound 1 (36.8 mg, 0.120 mmol) in THF (2 mL) was cooled in ice bath, and potassium t-butoxide (11.5 mg, 0.103 mmol) was added thereto, then the mixture was stirred at room temperature. After completion of the reaction, water and ethyl acetate were added thereto, and a liquid-liquid separation was performed. The organic layer was concentrated under reduced pressure, and the obtained residue was purified by silica gel column chromatography to obtain Compound 24 (61.8 mg, 71.4%).

Compound 24; Method C
LC/MS retention time=3.29 min.
MS (ESI) m/z=644.20 (M+H)+.

A solution of Compound 24 (58.4 mg, 0.090 mmol) in toluene (6 mL) was prepared and divided into two. To one toluene solution were added Compound 9 (61.1 mg, 0.170 mmol), PdCl$_2$(dtbpf) (5.9 mg, 9.1 μmol) and a 2 mol/L aqueous solution of potassium carbonate (45 μL, 0.090 mmol), and the mixture was stirred under microwave irradiation at 130° C. for 13 minutes. However, the reaction mixture was unreacted, thus toluene was removed under reduced pressure, and 1,4-dioxane (3 mL) was added thereto, then the mixture was again stirred at 130° C. for 10 minutes. In addition, to another toluene solution were added Compound 9 (61.1 mg, 0.170 mmol), PdCl$_2$(dppf)CH$_2$Cl$_2$ (3.8 mg, 4.7 μmol) and a 2 mol/L aqueous sodium carbonate solution (45 μL, 0.090 mmol), and the mixture was stirred under microwave irradiation at 130° C. for 15 minutes. However, the reaction mixture was unreacted, thus toluene was removed under reduced pressure, and 1,4-dioxane (3 mL), PdCl$_2$(dtbpf) (3.0 mg, 4.5 μmol) and a 2 mol/L aqueous solution of potassium carbonate (23 μL, 0.046 mmol) were added thereto, then the mixture was again stirred under microwave irradiation at 130° C. for 15 minutes. Two reaction mixtures were combined and concentrated under reduced pressure, and water and ethyl acetate were added to the residue, then a liquid-liquid separation was performed. The organic layer was concentrated under reduced pressure, and the obtained residue was purified by silica gel column chromatography to obtain Compound 25 (37.4 mg).

Compound 25; Method C
LC/MS retention time=3.15 min.
MS (ESI) m/z=854.20 (M+H)+.

To a solution of Compound 25 (37.4 mg) in a mixture of methanol (2.5 mL) and water (0.5 mL) was added PPTS (7.5 mg, 0.030 mmol), and the mixture was heated under reflux for 2 hours. Then, PPTS (5.5 mg, 0.022 mmol) was added thereto, and the mixture was heated under reflux for further 3 hours. The reaction mixture was concentrated under reduced pressure, then ethyl acetate and water were added to the residue, and a liquid-liquid separation was performed. To a THF (2 mL) solution of the concentrated residue containing Compound 26 obtained by concentrating the organic layer under reduced pressure was added a 1 mol/L TBAF THF solution (35 μL, 0.035 mmol), and the mixture was stirred at room temperature. The reaction mixture was concentrated under reduced pressure to remove the THF, then ethyl acetate and water were added to the residue, and a liquid-liquid separation was performed. The obtained organic layer was concentrated under reduced pressure, and the obtained residue was purified by silica gel column chromatography and reverse-phase column chromatography to obtain Compound (I-1-5) (7.6 mg, 15.8%).

Compound (I-1-5); Method C
LC/MS retention time=1.56 min.
MS (ESI) m/z=531.00 (M+H)+.

Example 6

[Chemical formula 32]

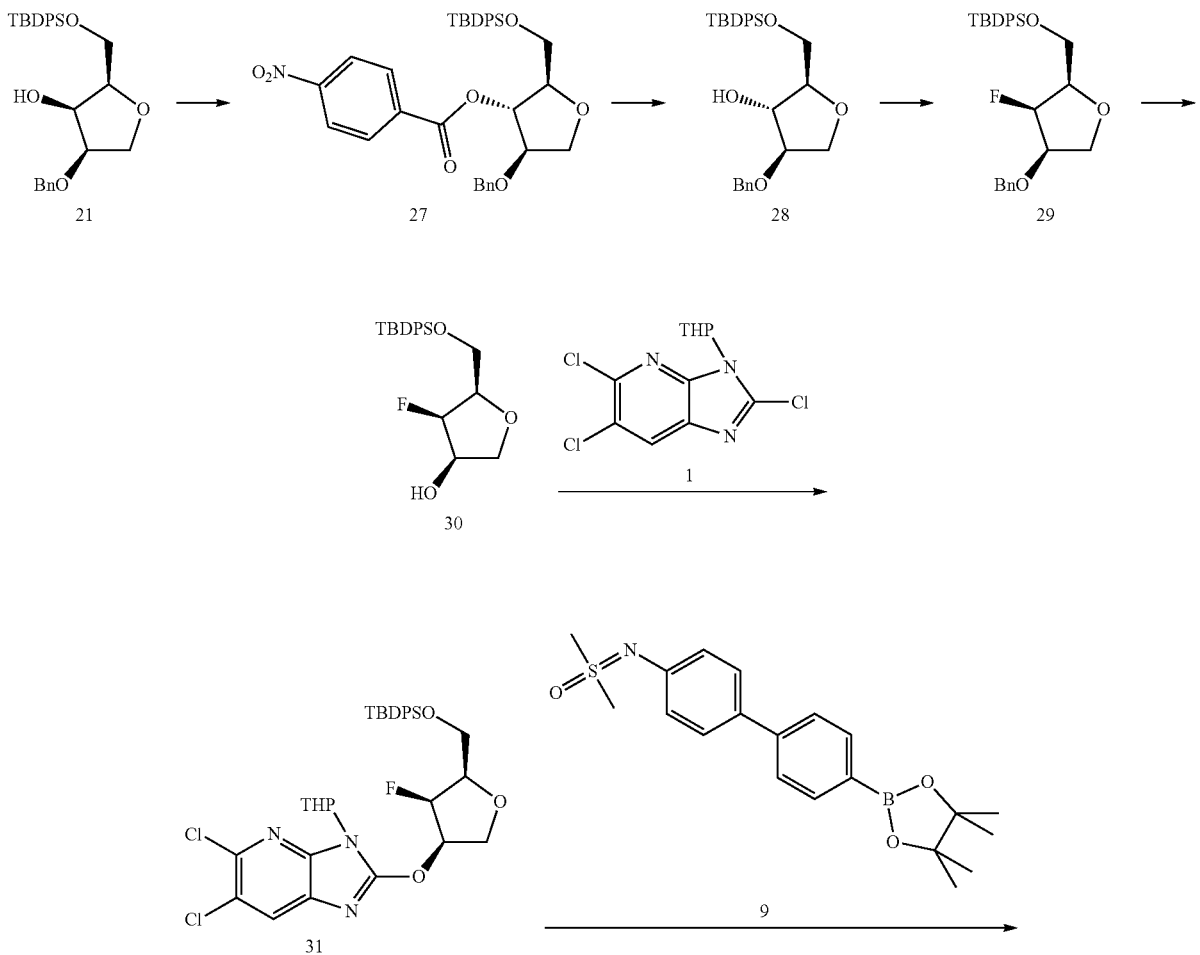

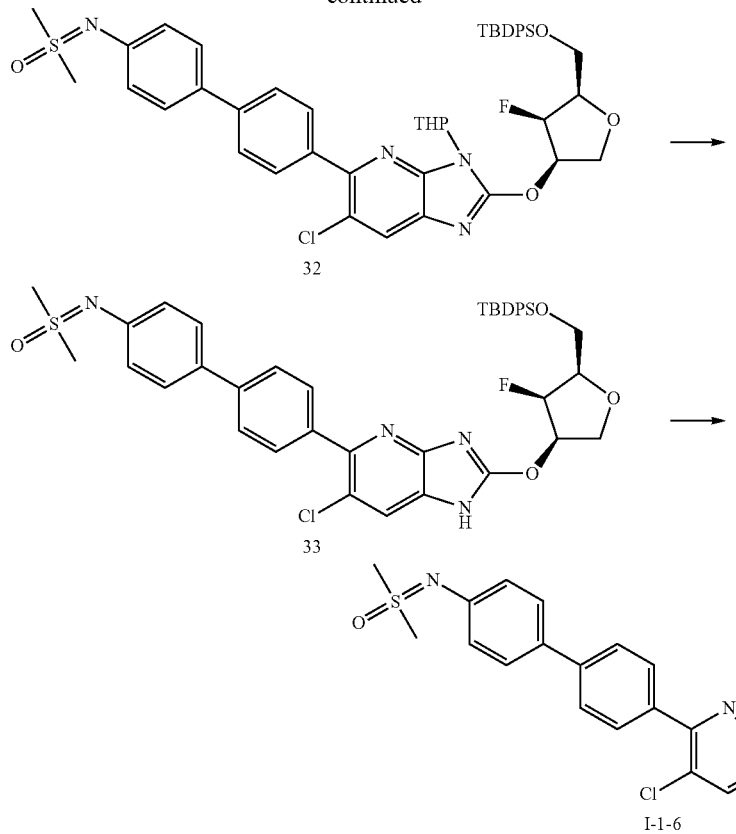

A solution of Compound 21 (919 mg, 1.99 mmol), 4-nitrobenzoic acid (0.498 g, 2.98 mmol) and triphenylphosphine (0.782 g, 2.98 mmol) in THF (10 mL) was cooled in ice bath, and a 1.9 mol/L DIAD toluene solution (1.57 mL, 2.98 mmol) was added dropwise thereto, then the mixture was stirred at room temperature for 3 hours. The reaction mixture was concentrated under reduced pressure, and the obtained residue was purified by silica gel column chromatography to obtain Compound 27 (1.15 g, 94.8%).

Compound 27;

$^1$H-NMR (CDCl$_3$) δ: 1.04 (9H, s), 3.87 (1H, dd, J=10.5, 7.1 Hz), 3.93 (1H, dd, J=10.4, 5.6 Hz), 4.03 (2H, d, J=3.5 Hz), 4.14-4.20 (2H, m), 4.59 (1H, d, J=12.0 Hz), 4.71 (1H, d, J=12.0 Hz), 5.64 (1H, s), 7.29-7.41 (11H, m), 7.67 (4H, d, J=6.7 Hz), 8.20 (2H, d, J=8.8 Hz), 8.31 (2H, d, J=8.8 Hz).

To a solution of Compound 27 (451 mg, 0.737 mmol) in THF (4 mL) and methanol (2 mL) was added a 2 mol/L aqueous sodium hydroxide solution (0.737 ml, 1.47 mmol), and the mixture was stirred at room temperature. The reaction mixture was concentrated under reduced pressure to remove the THF and methanol, then water and ethyl acetate were added to the obtained residue, and a liquid separating operation was performed. The obtained organic layer was concentrated under reduced pressure, and the obtained residue was purified by silica gel column chromatography to obtain Compound 28 (339 mg, 99.5%).

Compound 28;

$^1$H-NMR (CDCl$_3$) δ: 1.07 (9H, s), 1.87 (1H, s), 3.73-3.92 (4H, m), 3.97-4.07 (2H, m), 4.32 (1H, s), 4.53 (1H, d, J=11.8 Hz), 4.59 (1H, d, J=11.8 Hz), 7.27-7.46 (11H, m), 7.66 (4H, d, J=7.3 Hz).

Compound 29 was synthesized from Compound 28, in a similar way that Compound 22 was synthesized from Compound 21.

Compound 29;

$^1$H-NMR (CDCl$_3$) δ: 1.06 (9H, s), 3.73-4.25 (6H, m), 4.48-4.70 (2H, m), 5.15 (1H, dd, J=52.6, 13.7 Hz), 7.26-7.45 (11H, m), 7.64-7.71 (4H, m).

Compound 30 was synthesized from Compound 29, in a similar way that Compound 23 was synthesized from Compound 22.

Compound 30;

$^1$H-NMR (CDCl$_3$) δ: 1.06 (9H, s), 3.72-3.89 (1H, m), 3.93-4.14 (4H, m), 4.22-4.53 (2H, m), 5.05 (1H, d, J=52.5 Hz), 7.39-7.49 (6H, m), 7.66-7.74 (4H, m).

Compound 31 was synthesized from Compounds 30 and 1, in a similar way that Compound 24 was synthesized from Compounds 23 and 1.

Compound 31; Method C

LC/MS retention time=3.26 min.

MS (ESI) m/z=644.05 (M+H)+.

A solution of Compound 31 (94.2 mg) in 1,4-dioxane (6.6 mL) was prepared, and to 2.2 mL of the solution were added Compound 9 (21.7 mg, 0.058 mmol), Pd(Ph$_3$P)$_4$ (11.3 mg, 9.74 μmol) and a 2 mol/L aqueous solution of potassium carbonate (49 μL, 0.098 mmol), then the mixture was stirred under microwave irradiation at 130° C. for 45 minutes. In addition, to remaining 4.4 mL of the solution were added Compound 9 (43.4 mg, 0.117 mmol), Pd(Ph$_3$P)$_4$ (22.5 mg, 0.019 mmol) and a 2 mol/L aqueous solution of potassium carbonate (97 μL, 0.194 mmol), and the reaction mixture was stirred under microwave irradiation at 130° C. for 90 minutes. Two reaction mixtures were combined and concentrated under reduced pressure to remove the toluene, then water and ethyl acetate were added to the residue, and a liquid-liquid separation was performed. The obtained organic layer was concentrated under reduced pressure, and the obtained residue was purified by silica gel column chromatography to obtain Compound 32 (124 mg).
Compound 32; Method C
LC/MS retention time=3.13 min.
MS (ESI) m/z=853.15 (M+H)+.

Compound 33 was synthesized from Compound 32, in a similar way that Compound 26 was synthesized from Compound 25. Compound (I-1-6) was synthesized from Compound 33, in a similar way that Compound (I-1-5) was synthesized from Compound 26.
Compound (I-1-6); Method C
LC/MS retention time=1.66 min.
MS (ESI) m/z=531.00 (M+H)+.

Example 7

[Chemical formula 33]

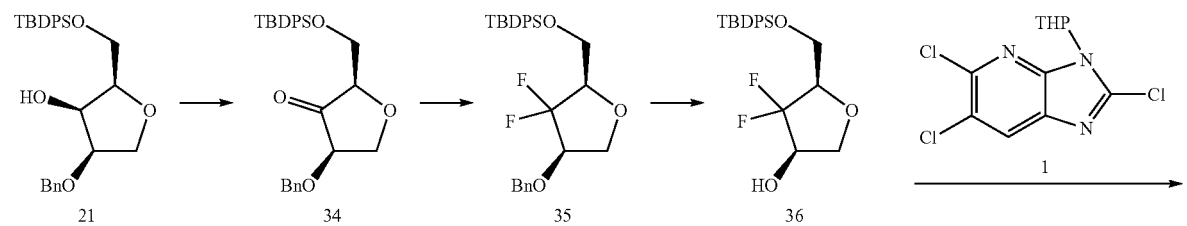

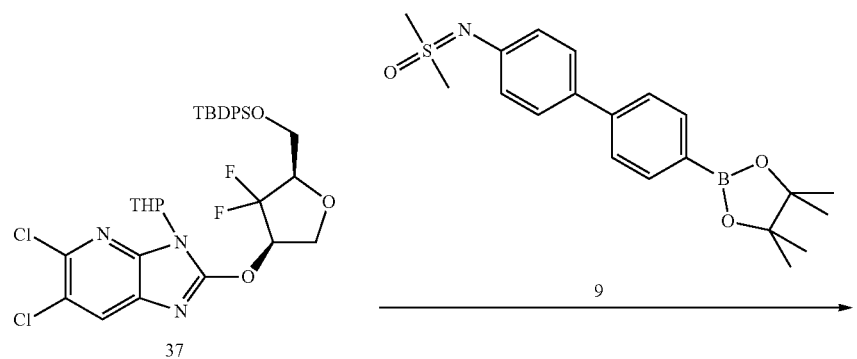

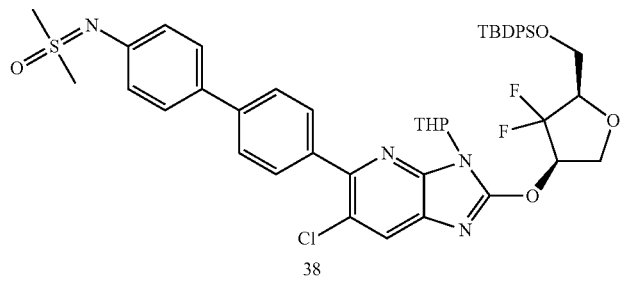

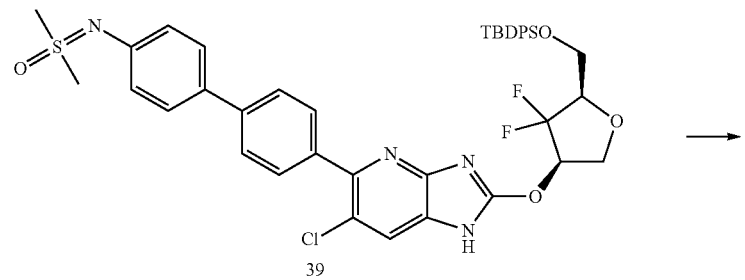

-continued

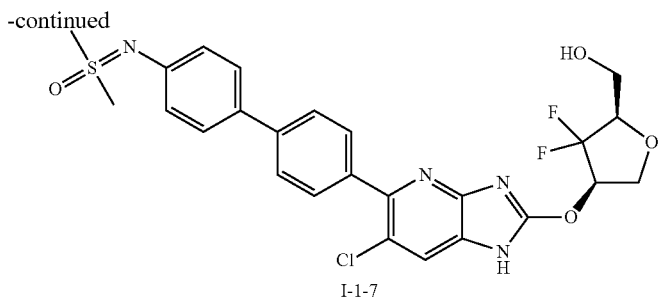

I-1-7

To a solution of Compound 21 (464 mg, 1.00 mmol) in dichloromethane (8 mL) was added 1,1,1-triacetoxy-1,1-dihydro-1,2-benziodoxol-3-(1H)-one (510 mg, 1.20 mmol), and the mixture was stirred at room temperature. The reaction mixture was filtered and concentrated under reduced pressure, and the obtained residue was purified by silica gel column chromatography to obtain Compound 34 (451 mg, 97.7%).

Compound 34;
$^1$H-NMR (CDCl$_3$) δ: 1.02 (9H, s), 3.89 (1H, dd, J=11.9, 3.6 Hz), 3.98-4.03 (2H, m), 4.16-4.25 (2H, m), 4.36 (1H, t, J=7.5 Hz), 4.69 (1H, d, J=11.9 Hz), 4.96 (1H, d, J=11.9 Hz), 7.29-7.45 (11H, m), 7.66-7.71 (4H, m).

To a solution of Compound 34 (451 mg, 0.979 mmol) in 1,2-dichloroethane (8 mL) was added DAST (0.517 ml, 3.91 mmol), then the mixture was stirred at room temperature for 24 hours, and further heated at 80° C. for 7 hours. The reaction mixture cooled to room temperature was poured to a mixture of sodium hydrogencarbonate (822 mg, 9.79 mmol) and ice water, then ethyl acetate was added, and a liquid-liquid separation was performed. The obtained organic layer was concentrated under reduced pressure, and the obtained residue was purified by silica gel column chromatography to obtain Compound 35 (300 mg, 63.5%).

Compound 35;
$^1$H-NMR (CDCl$_3$) δ: 1.06 (9H, s), 3.78-4.15 (6H, m), 4.54 (1H, d, J=11.8 Hz), 4.79 (1H, d, J=11.8 Hz), 7.27-7.47 (11H, m), 7.65-7.72 (4H, m).

Compound 36 was synthesized from Compound 35, in a similar way that Compound 23 was synthesized from Compound 22.

Compound 37 was synthesized from Compounds 36 and 1, in a similar way that Compound 24 was synthesized from Compounds 23 and 1. Compound 38 was synthesized from Compounds 37 and 9, in a similar way that Compound 32 was synthesized from Compounds 31 and 9. Compound 39 was synthesized from Compound 38, in a similar way that Compound 26 was synthesized from Compound 25. Compound (I-1-7) was synthesized from Compound 39, in a similar way that Compound (I-1-5) was synthesized from Compound 26.

Compound (I-1-7); Method C
LC/MS retention time=1.75 min.
MS (ESI) m/z=549.00 (M+H)+.

Example 8

[Chemical formula 34]

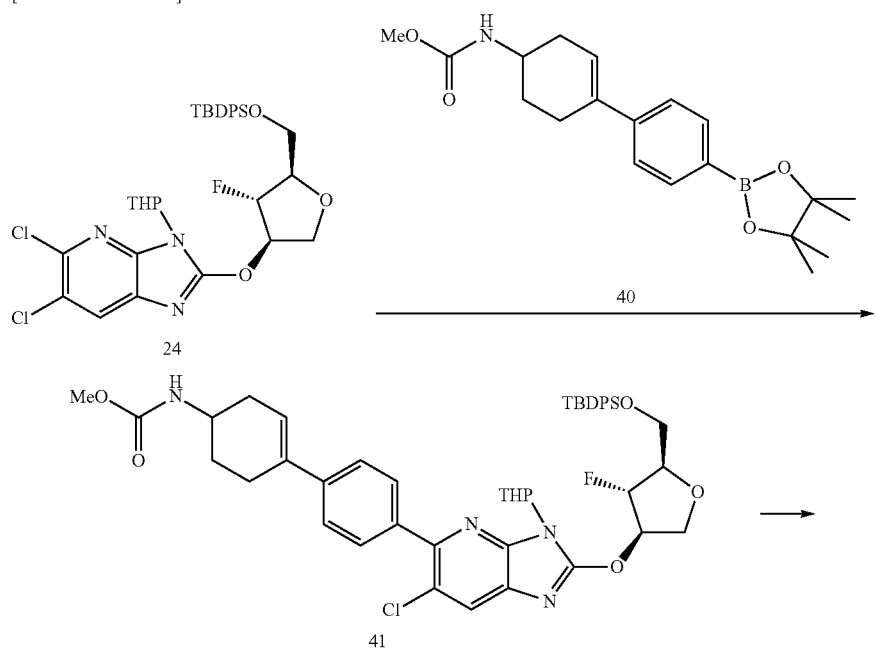

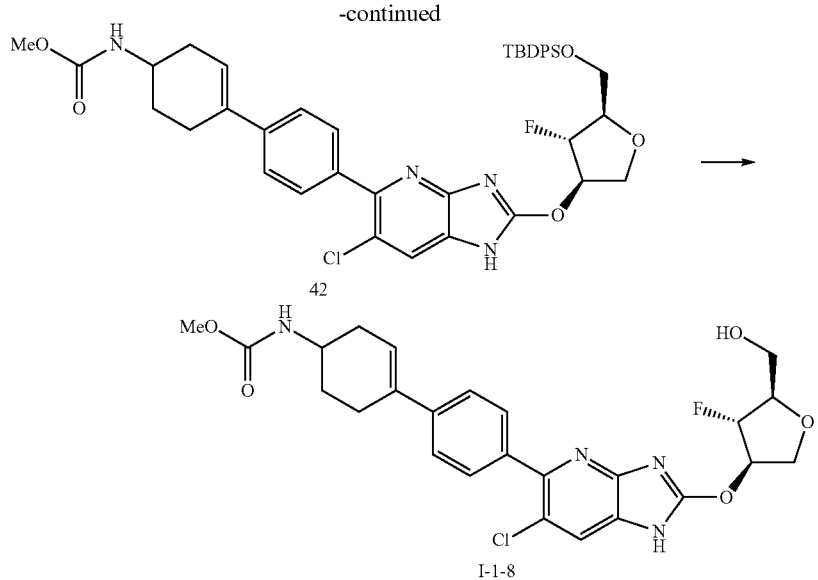

Compound 41 was synthesized from Compounds 24 and 40, in a similar way that Compound 32 was synthesized from Compounds 31 and 9. Compound 42 was synthesized from Compound 41, in a similar way that Compound 26 was synthesized from Compound 25. Compound (I-1-8) was synthesized from Compound 42, in a similar way that Compound (I-1-5) was synthesized from Compound 26.

Compound (I-1-8); Method C
LC/MS retention time=1.76 min.
MS (ESI) m/z=517.10 (M+H)+.

Example 9

[Chemical formula 35]

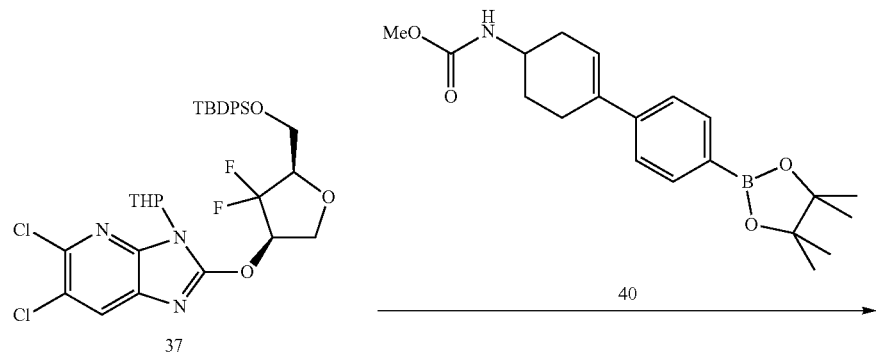

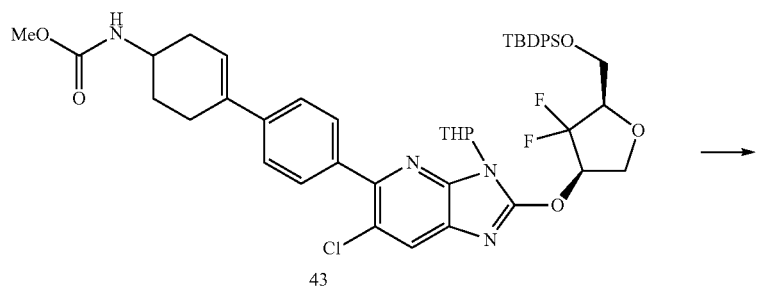

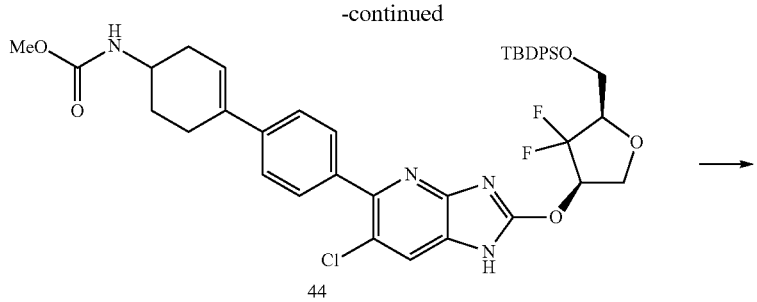

44

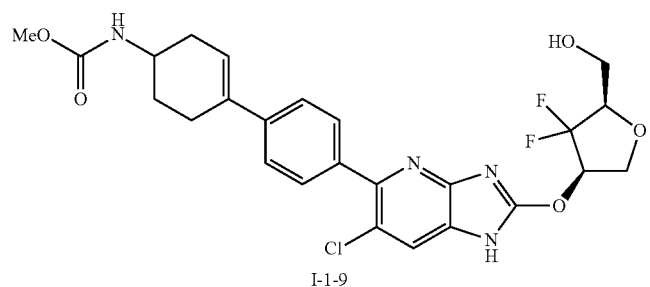

I-1-9

Compound 43 was synthesized from Compounds 37 and 40, in a similar way that Compound 32 was synthesized from Compounds 31 and 9. Compound 44 was synthesized from Compound 43, in a similar way that Compound 26 was synthesized from Compound 25. Compound (I-1-9) was synthesized from Compound 44, in a similar way that Compound (I-1-5) was synthesized from Compound 26.

Compound (I-1-9); Method C
LC/MS retention time=1.69 min.
MS (ESI) m/z=535.05 (M+H)+.

Example 10

[Chemical formula 36]

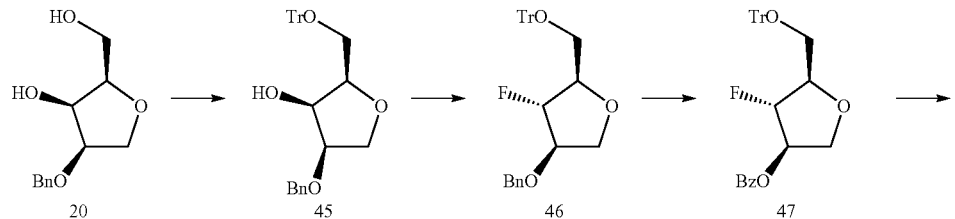

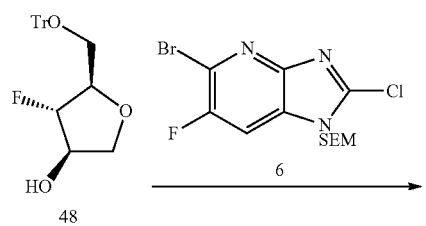

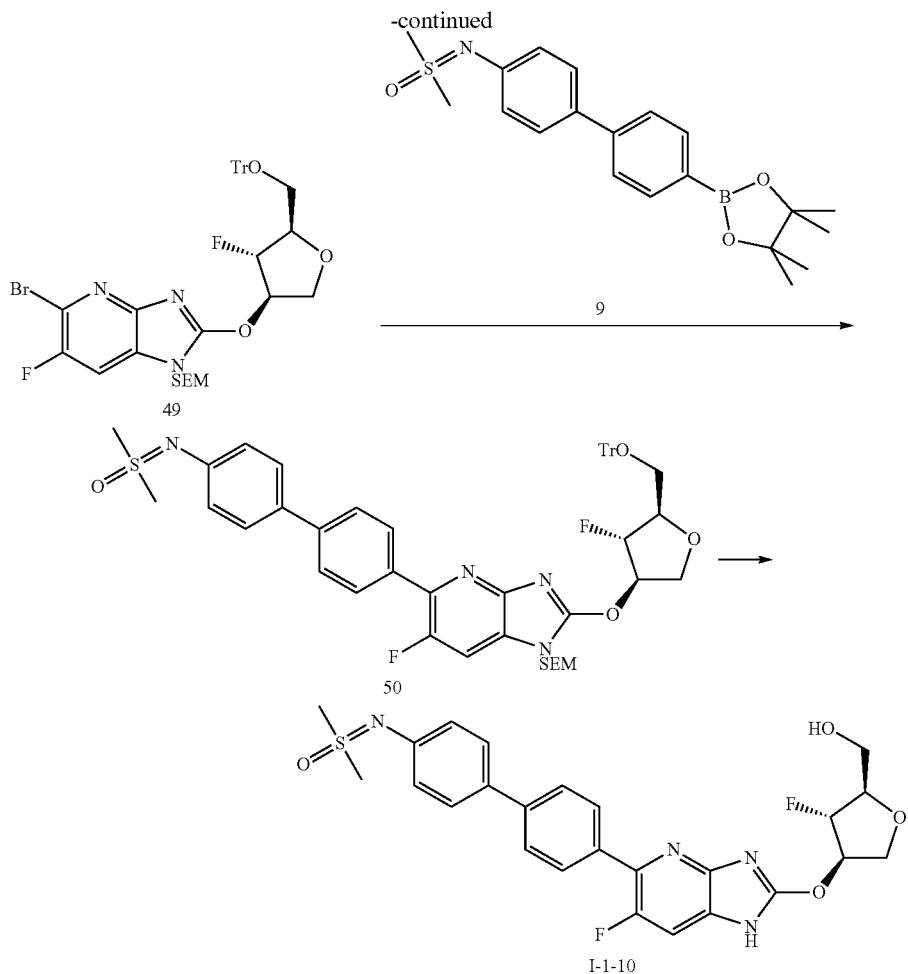

To a solution of Compound 20 (10.0 g, 44.6 mmol) and triphenylmethyl chloride (14.3 g, 51.3 mmol) in dichloromethane (100 mL) were added triethylamine (8.65 ml, 62.4 mmol) and DMAP (0.545 g, 4.46 mmol), and the mixture was stirred at room temperature. After completion of the reaction, the reaction mixture was concentrated under reduced pressure, then ethyl acetate and water were added thereto, and a liquid-liquid separation was performed. The organic layer was concentrated under reduced pressure, and the obtained residue was purified by silica gel column chromatography and further crystallized by ethyl acetate-hexane to obtain Compound 45 (16.4 g, 79.0%).

Compound 45;

$^1$H-NMR (CDCl$_3$) δ: 2.66 (1H, d, J=4.8 Hz), 3.36 (1H, dd, J=9.8, 6.3 Hz), 3.43 (1H, dd, J=9.8, 5.0 Hz), 3.85 (1H, dd, J=9.2, 6.3 Hz), 3.91 (1H, dd, J=9.2, 6.7 Hz), 3.99 (1H, dd, J=10.3, 4.9 Hz), 4.15 (1H, dd, J=11.6, 6.2 Hz), 4.26 (1H, q, J=4.6 Hz), 4.56 (1H, d, J=11.7 Hz), 4.63 (1H, d, J=11.7 Hz), 7.21 (3H, t, J=7.2 Hz), 7.24-7.38 (10H, m), 7.47 (6H, d, J=7.4 Hz).

Compound 46 was synthesized from Compound 45, in a similar way that Compound 22 was synthesized from Compound 21.

Compound 46; Method C

LC/MS retention time=2.84 min.

MS (ESI) m/z=491.05 (M+Na)+.

To a solution of Compound 46 (282.0 mg, 0.602 mmol) in carbon tetrachloride (5.6 mL), acetonitrile (5.1 mL) and distilled water (7.2 mL) were added sodium periodate (282.0 mg, 0.602 mmol) and ruthenium(IV) oxide hydrate (14.6 mg, 0.097 mmol) at room temperature, and the mixture was stirred at room temperature. After completion of the reaction, the reaction mixture was concentrated under reduced pressure, then ethyl acetate and water were added thereto, and a liquid-liquid separation was performed. The obtained organic layer was filtered and concentrated under reduced pressure, and the residue containing Compound 47 was diluted with THF (2 mL) and methanol (1 mL). A 2 mol/L aqueous sodium hydroxide solution (451 μl, 0.903 mmol) was added thereto at room temperature, and the mixture was stirred at room temperature. After completion of the reaction, the reaction mixture was concentrated, then water and ethyl acetate were added to the obtained residue, and a liquid-liquid separation was performed. The organic layer was concentrated under reduced pressure, and the obtained residue was purified by silica gel column chromatography to obtain Compound 48 (129.6 mg, 46.0%).

Compound 48;

$^1$H-NMR (CDCl$_3$) δ: 3.25 (1H, dd, J=10.4, 2.1 Hz), 3.53 (1H, d, J=10.8 Hz), 3.61-3.66 (1H, m), 3.93-3.99 (1H, m), 4.04-4.15 (2H, m), 4.22-4.30 (1H, m), 4.84 (1H, d, J=52.2 Hz), 7.23-7.29 (8H, m), 7.33 (6H, t, J=7.4 Hz), 7.42 (6H, d, J=7.9 Hz).

A solution of Compound 48 (33.9 mg, 0.090 mmol) and Compound 6 (26.2 mg, 0.069 mmol) in THF (2 mL) was cooled in ice bath, and potassium t-butoxide (10.1 mg, 0.090 mmol) was added thereto, then the mixture was stirred at room temperature for 30 minutes. Compound 6 (13.1 mg, 0.034 mmol) was added thereto, and the mixture was further stirred for 1.5 hours. After completion of the reaction, water and ethyl acetate were added thereto, and a liquid-liquid separation was performed. The organic layer was concentrated under reduced pressure, and the obtained residue was purified by silica gel column chromatography to obtain Compound 49 (57.5 mg, 88.8%).

Compound 49;

$^1$H-NMR (CDCl$_3$) δ: −0.09 (9H, s), 0.80 (2H, dd, J=10.4, 5.7 Hz), 3.21 (1H, dd, J=9.5, 6.3 Hz), 3.31 (2H, t, J=8.3 Hz), 3.41 (1H, dd, J=9.3, 5.3 Hz), 3.71-3.77 (1H, m), 4.20-4.34 (3H, m), 4.97 (2H, s), 5.30 (1H, d, J=50.7 Hz), 5.68 (1H, d, J=14.6 Hz), 7.24-7.31 (9H, m), 7.38-7.45 (7H, m).

Compound 50 was synthesized from Compounds 49 and 9, in a similar way that Compound 32 was synthesized from Compounds 31 and 9.

Compound 50 (17.8 mg, 0.020 mmol) and TFA (1 mL) were stirred at room temperature, and after completion of the reaction, the TFA was removed by nitrogen blow down. The same procedure was also carried out with Compound 50 (25.3 mg, 0.029 mmol). Two residues were combined using methanol and concentrated under reduced pressure. To the residue were added methanol (2 mL) and a 2 mol/L aqueous sodium carbonate solution (250 µl, 0.500 mmol) at room temperature, and the mixture was stirred at room temperature. After completion of the reaction, the reaction mixture was concentrated, and diluted with ethyl acetate and water, and a liquid-liquid separation was performed. The organic layer was concentrated, and the residue was purified by silica gel column chromatography to obtain (I-1-10) (6.9 mg, 27.4%). (Yield is total yield from Compound 49)

Compound (I-1-10); Method C

LC/MS retention time=1.59 min.

MS (ESI) m/z=515.10 (M+H)+.

Example 11

[Chemical formula 37]

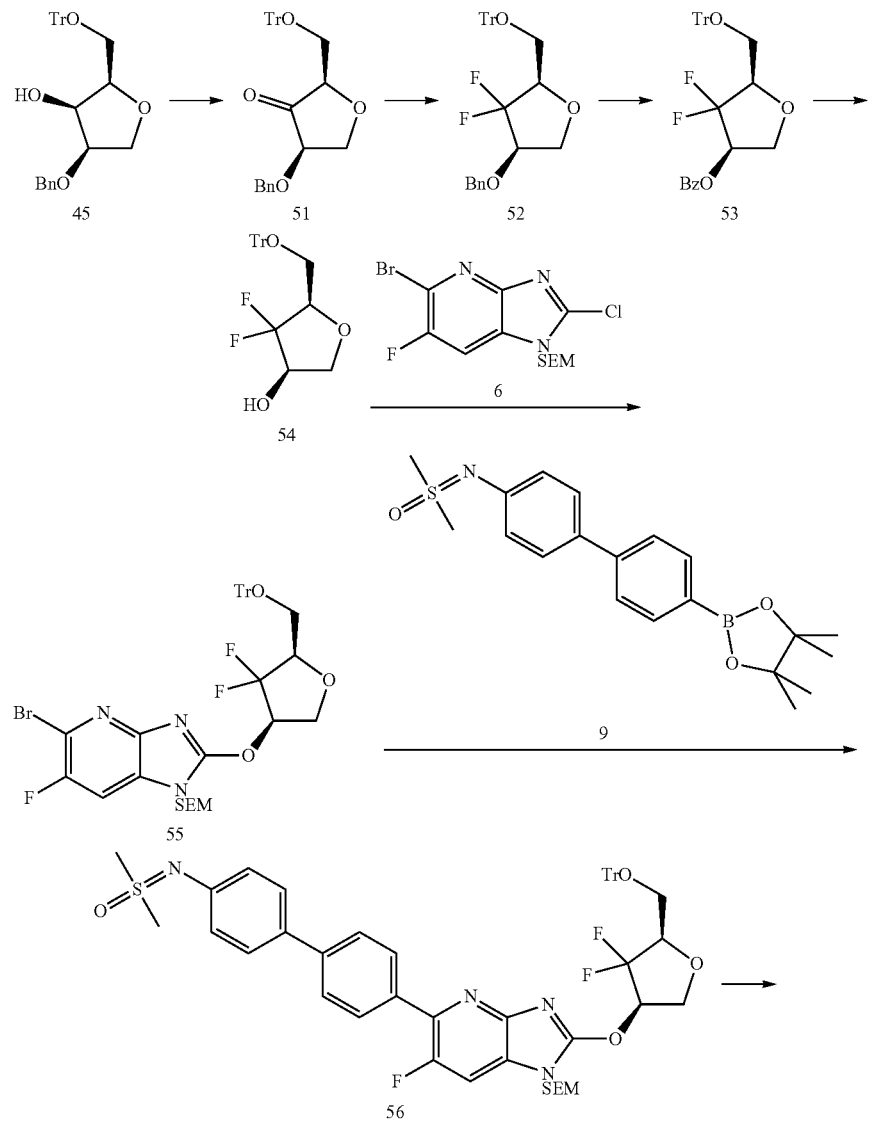

-continued

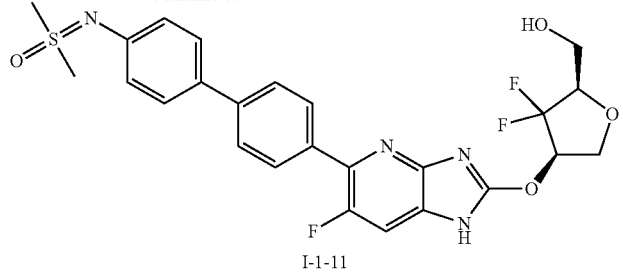

I-1-11

Compound 51 was synthesized from Compound 45, in a similar way that Compound 34 was synthesized from Compound 21.
Compound 51; Method C
LC/MS retention time=2.77 min.
MS (ESI) m/z=487.30 (M+Na)+.
Compound 52 was synthesized from Compound 51, in a similar way that Compound 35 was synthesized from Compound 34.
Compound 52; Method C
LC/MS retention time=2.86 min.
MS (ESI) m/z=509.00 (M+Na)+.
Compound 53 was synthesized from Compound 52, in a similar way that Compound 47 was synthesized from Compound 46.
Compound 54 was synthesized from Compound 53, in a similar way that Compound 48 was synthesized from Compound 47.
Compound 54;
$^1$H-NMR (CDCl$_3$) δ: 3.25 (1H, d, J=10.5 Hz), 3.52 (1H, d, J=10.5 Hz), 3.61 (1H, d, J=9.5 Hz), 4.00-4.21 (4H, m), 7.22-7.28 (3H, m), 7.32 (6H, t, J=7.2 Hz), 7.45 (6H, d, J=7.4 Hz).

Compound 55 was synthesized from Compounds 54 and 6, in a similar way that Compound 49 was synthesized from Compounds 48 and 6.
Compound 55;
$^1$H-NMR (CDCl$_3$) δ: −0.11−−0.04 (9H, m), 0.80-0.88 (2H, m), 3.34-3.45 (4H, m), 4.16-4.26 (2H, m), 4.35 (1H, dd, J=11.5, 4.5 Hz), 5.14 (1H, d, J=11.3 Hz), 5.18 (1H, d, J=11.5 Hz), 5.62-5.70 (1H, m), 7.22-7.34 (9H, m), 7.40-7.50 (7H, m).

Compound 56 was synthesized from Compounds 55 and 9, in a similar way that Compound 50 was synthesized from Compounds 49 and 9.
Compound (I-1-11) was synthesized from Compound 56, in a similar way that Compound (I-1-10) was synthesized from Compound 50.
Compound (I-1-11); Method C
LC/MS retention time=1.65 min.
MS (ESI) m/z=533.15 (M+H)+.

Example 12

[Chemical formula 38]

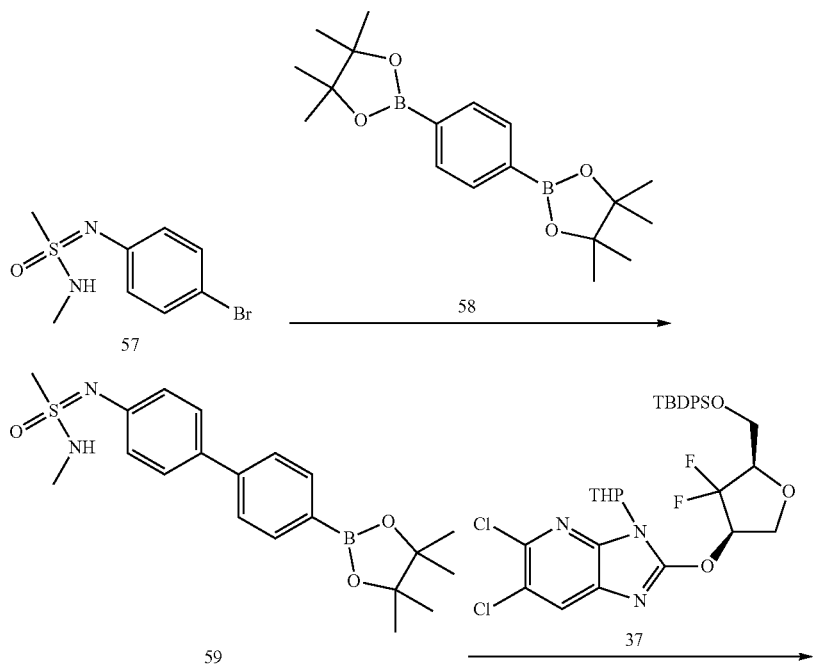

-continued

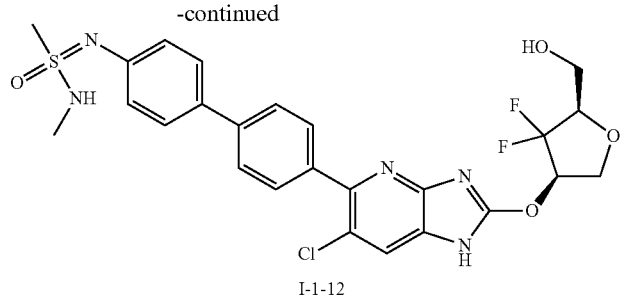

I-1-12

To a solution of Compound 57 (500 mg, 1.90 mmol) and Compound 58 (1881 mg, 5.70 mmol) in 1,4-dioxane (10 mL) were added PdCl$_2$(dtbpf) (186 mg, 0.285 mmol) and a 2 mol/L aqueous solution of potassium carbonate (1.425 mL, 2.85 mmol), and the mixture was stirred at 80° C. The obtained reaction mixture was dried over magnesium sulfate and filtered. The obtained filtrate was concentrated under reduced pressure, and purified by silica gel column chromatography to obtain Compound 59.
Compound 59; Method B
LC/MS retention time=2.20 min.
MS (ESI) m/z=387.00 (M+H)+.

Compound (I-1-12) was synthesized from Compound 59, in a similar way that Compound (I-1-7) was synthesized from Compound 9.
Compound (I-1-12); Method C
LC/MS retention time=1.73 min.
MS (ESI) m/z=564.15 (M+H)+.

Example 13

[Chemical formula 39]

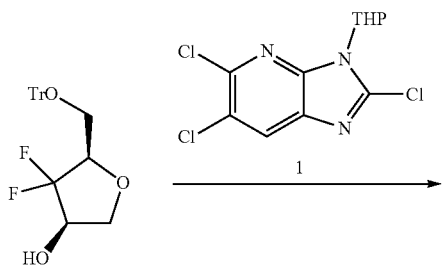

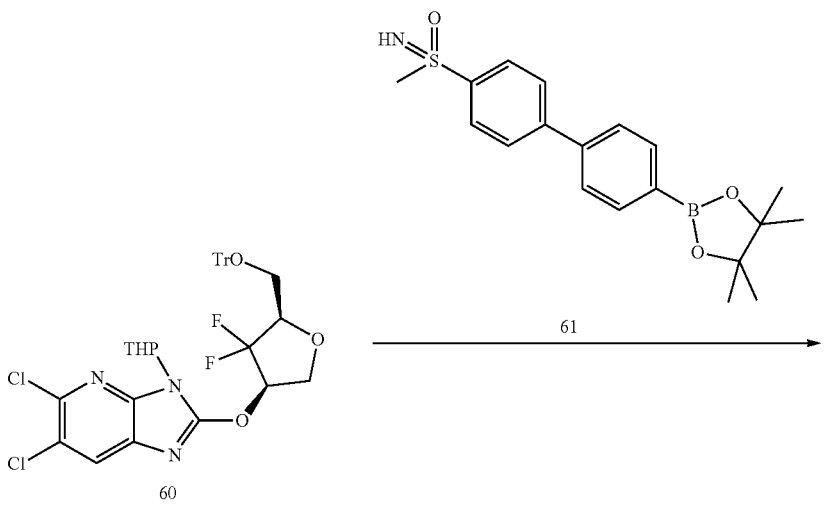

-continued

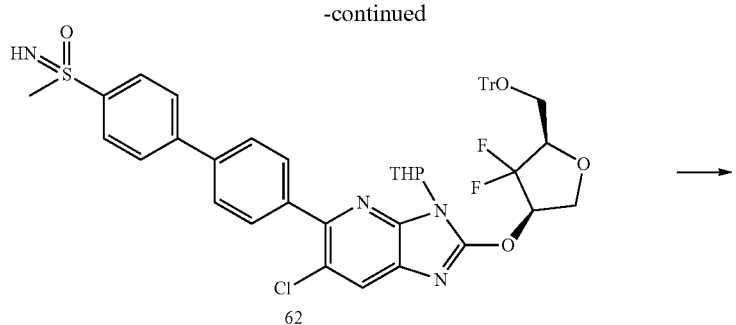

62

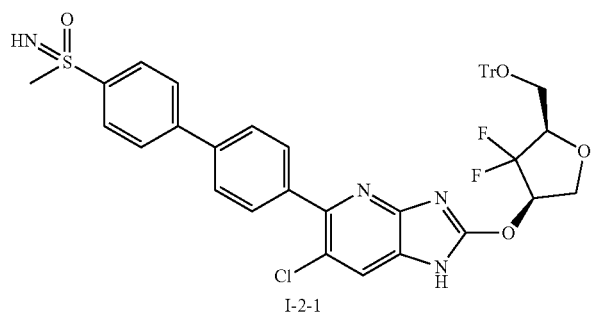

I-2-1

To a solution of Compound 54 (581 mg, 98.0 wt %, 1.44 mmol) and Compound 1 (400 mg, 1.31 mmol) in THF (6 mL) was added potassium tert-butoxide (176 mg, 1.57 mmol), and the mixture was stirred at room temperature. After completion of the reaction, water and ethyl acetate were added thereto, and a liquid-liquid separation was performed. The organic layer was concentrated under reduced pressure, and the obtained residue was purified by silica gel column chromatography to obtain Compound 60 (688 mg, 79.1%).

Compound 60; Method C
LC/MS retention time=3.15 min.

To a solution of Compound 60 (100 mg, 0.150 mmol) and Compound 61 (64.3 mg, 0.180 mmol) in 1,4-dioxane (1.2 mL) were added Pd(Ph$_3$P)$_4$ (17.3 mg, 0.015 mmol) and a 2 mol/L aqueous solution of potassium carbonate (300 μL, 0.600 mmol), then the mixture was stirred under microwave irradiation at 130° C. The obtained reaction mixture was purified by silica gel column chromatography to obtain Compound 62 (108 mg, 83.6%).

Compound 62; Method C
LC/MS retention time=2.92 min.
MS (ESI) m/z=860.10 (M+H)+.

A solution of Compound 62 (108 mg, 0.125 mmol) in TFA (1.3 mL) was stirred at room temperature. After completion of the reaction, TFA was removed under reduced pressure, and THF (2 mL) and methanol (1 mL) was added to the residue. A 2 mol/L aqueous sodium carbonate solution (627 μl, 1.26 mmol) was added thereto at room temperature, and the mixture was stirred at room temperature. After completion of the reaction, the reaction mixture was concentrated under reduced pressure, then ethyl acetate and water were added thereto, and a liquid-liquid separation was performed. The organic layer was concentrated under reduced pressure, and the obtained residue was purified by silica gel column chromatography to obtain Compound (I-2-1) (25.1 mg, 37.4%).

Compound (I-2-1); Method C
LC/MS retention time=1.57 min.
MS (ESI) m/z=535.15 (M+H)+.

Example 14

[Chemical formula 40]

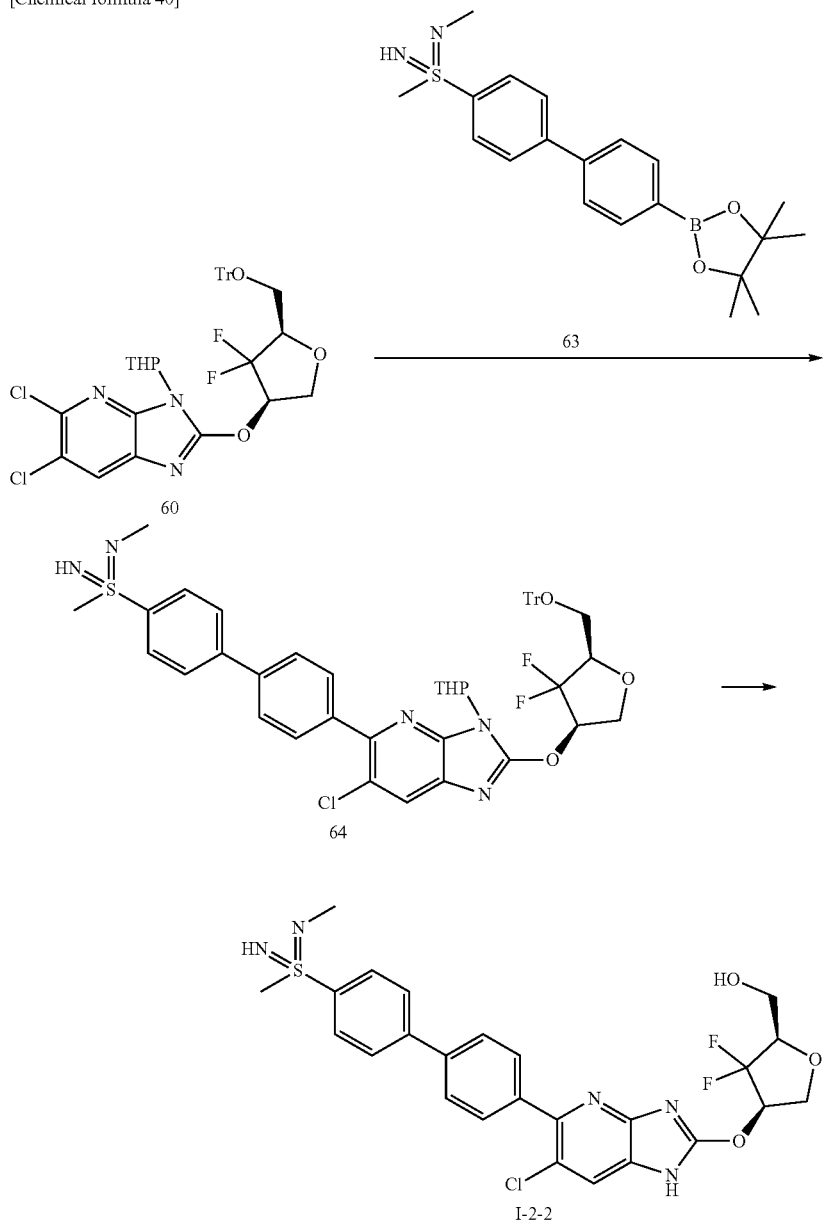

Compound 64 was synthesized from Compound 63, in a similar way that Compound 62 was synthesized from Compound 61.
Compound 64; Method C
LC/MS retention time=2.47 min.
MS (ESI) m/z=874.30 (M+H)+.

Compound 64 (theoretical amount 79.0 mg, 0.090 mmol) and TFA (1 mL) were stirred at room temperature. After completion of the reaction, TFA was removed under reduced pressure, and THF (2 mL) and methanol (1 mL) were added to the residue. A 2 mol/L aqueous sodium carbonate solution (675 μl, 1.35 mmol) was added thereto at room temperature, and the mixture was stirred at room temperature. After completion of the reaction, the reaction mixture was concentrated under reduced pressure, then ethyl acetate and water were added thereto, and a liquid-liquid separation was performed. The organic layer was concentrated under reduced pressure, then a 2 mol/L methanol hydrochloride solution (135 μl, 0.270 mmol) and a 2 mol/L aqueous solution of hydrochloric acid (225 μl, 0.450 mmol) were added thereto, and the mixture was stirred at 60° C. Sodium hydrogencarbonate (76.0 mg, 0.900 mmol) was added to neutralize the reaction mixture. The reaction mixture was concentrated under reduced pressure, and the obtained residue was purified by silica gel column chromatography to obtain Compound (I-2-2) (5.3 mg, 10.7%).
Compound (I-2-2); Method C
LC/MS retention time=1.39 min.
MS (ESI) m/z=548.15 (M+H)+.

Example 15

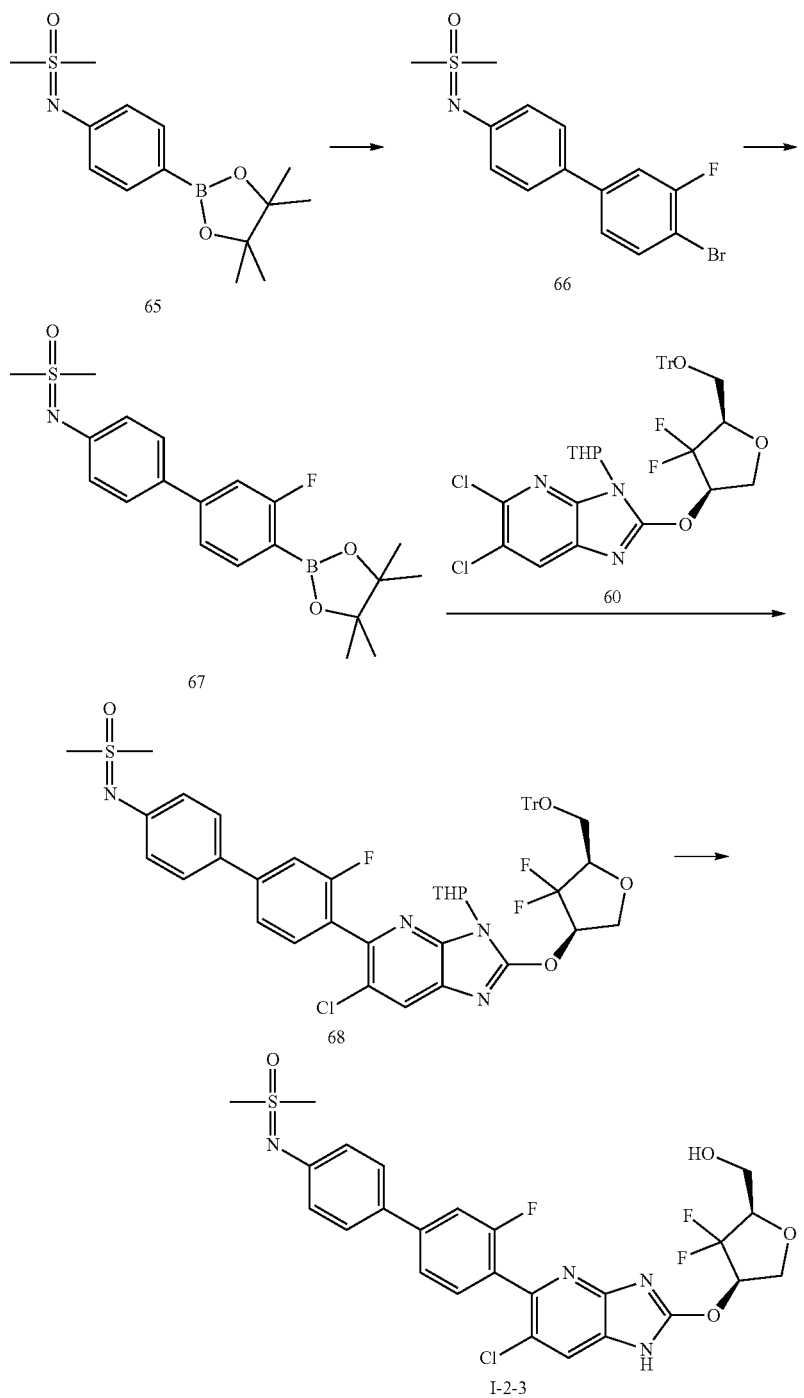

To a solution of Compound 65 (213 mg, 0.721 mmol) and 1-bromo-2-fluoro-4-iodobenzene (249 mg, 0.829 mmol) in 1,4-dioxane (20 mL) were added $PdCl_2(dppf)CH_2Cl_2$ (58.8 mg, 0.072 mmol) and a 2 mol/L aqueous solution of potassium carbonate (0.721 mL, 1.44 mmol), and the mixture was heated under reflux. The reaction mixture was concentrated under reduced pressure, and the obtained residue was purified by silica gel column chromatography and further crystallized by ethyl acetate-hexane to obtain Compound 66 (137 mg, 55.5%).

Compound 66; Method C

LC/MS retention time=2.07 min.

MS (ESI) m/z=342.00 (M+H)+.

To a solution of Compound 66 (137 mg, 0.400 mmol) and bis(pinacolato)diboron (144 mg, 0.567 mmol) in 1,4-dioxane (2 mL) were added potassium acetate (151 mg, 1.54 mmol) and PdCl$_2$(dppf) (18.0 mg, 0.025 mmol), and the mixture was stirred at 80° C. The reaction mixture was filtered with celite, and the filtrate was concentrated under reduced pressure. The obtained residue was purified by silica gel column chromatography to obtain Compound 67 (152 mg, 83.4 wt %, 81.2%).

Compound 67; Method C
LC/MS retention time=2.17 min.
MS (ESI) m/z=390.20 (M+H)+.

To a solution of Compound 67 (64.6 mg, 0.144 mmol) and Compound 60 (80.0 mg, 0.120 mmol) in 1,4-dioxane (1.36 mL) were added Pd(Ph$_3$P)$_4$ (13.9 mg, 0.012 mmol) and a 2 mol/L aqueous solution of potassium carbonate (240 µL, 0.480 mmol), and the mixture was stirred under microwave irradiation at 130° C. The obtained reaction mixture was purified by silica gel column chromatography to obtain the mixture of Compound 68 (theoretical amount 107 mg, 0.120 mmol) and triphenylphosphine oxide. Total amount was used for next step without further purification.

Compound 68; Method C
LC/MS retention time=2.98 min.
MS (ESI) m/z=893.35 (M+H)+.

To a solution of Compound 68 (theoretical amount 107 mg, 0.120 mmol) and triphenylphosphine oxide in 80% ethanol (5 mL) was added PPTS (60.3 mg, 0.240 mmol), and the mixture was heated under reflux for 2.5 hours. PPTS (60.3 mg, 0.240 mmol) was added thereto, and the mixture was further heated under reflux for 1.5 hours. Ethyl acetate and water were added to the reaction mixture, and a liquid-liquid separation was performed. The organic layer was concentrated under reduced pressure, and the obtained residue was purified by silica gel column chromatography to obtain Compound (I-2-3) (23.3 mg, 34.2%).

Compound (I-2-3); Method C
LC/MS retention time=1.73 min.
MS (ESI) m/z=567.10 (M+H)+.

Example 16

[Chemical formula 42]

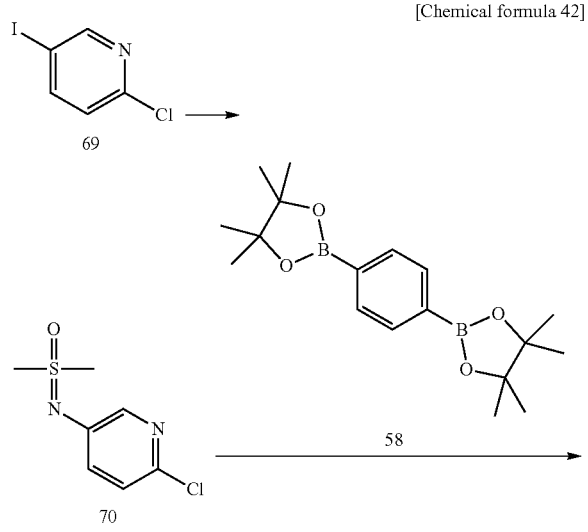

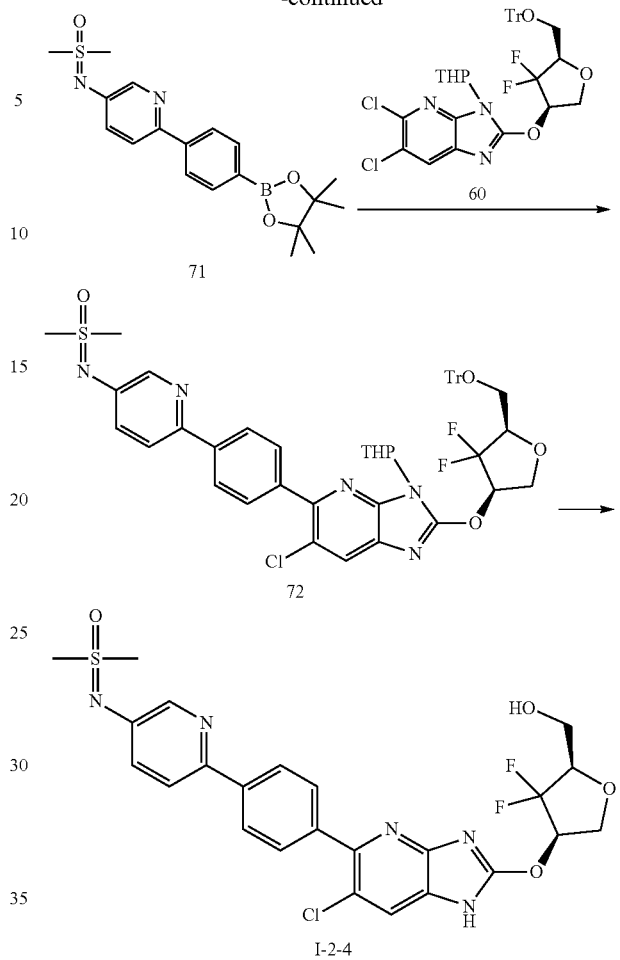

A solution of Compound 69 (965 mg, 4.03 mmol), dimethyl sulfoximine (450 mg, 4.83 mmol) and cesium carbonate (1.84 g, 5.64 mmol) in 1,4-dioxane (10 mL) was degassed. A solution of xantphos (175 mg, 0.302 mmol) and Pd$_2$(dba)$_3$ (92.0 mg, 0.101 mmol) in 1,4-dioxane (2 mL) was added thereto, and the mixture was heated under reflux. The reaction mixture was filtered with celite, and the filtrate was concentrated under reduced pressure. The obtained residue was purified by silica gel column chromatography to obtain Compound 70 (541 mg, 65.6%).

Compound 70; Method C
LC/MS retention time=1.06 min.
MS (ESI) m/z=205.00 (M+H)+.

To a solution of Compound 70 (173 mg, 0.845 mmol) and Compound 58 (1.69 g, 5.13 mmol) in 1,4-dioxane (6 mL) were added Pd(Ph$_3$P)$_4$ (98.0 mg, 0.084 mmol), and a 2 mol/L aqueous solution of potassium carbonate (1.27 mL, 2.53 mmol), and the mixture was stirred at 100° C. for 2 hours. The reaction mixture was diluted with 1,4-dioxane (6 mL), and the mixture was stirred under microwave irradiation at 130° C. for 0.5 hours. The reaction mixture was filtered with celite, and ethyl acetate and saturated aqueous sodium chloride were added to the obtained filtrate, then a liquid-liquid separation was performed. The organic layer was concentrated under reduced pressure, and the obtained residue was purified by silica gel column chromatography and further crystallized by ethyl acetate-hexane to obtain Compound 71 (137 mg, 55.5%).

Compound 71;

¹H-NMR (CDCl₃) δ: 1.36 (13H, s), 3.21 (7H, s), 7.49 (1H, dd, J=8.5, 2.5 Hz), 7.66 (1H, d, J=8.5 Hz), 7.88 (2H, d, J=8.0 Hz), 7.96 (2H, d, J=8.0 Hz), 8.45 (1H, d, J=2.3 Hz).

Compound 72 was synthesized from Compound 71, in a similar way that Compound 68 was synthesized from Compound 67.
Compound 72; Method C
LC/MS retention time=2.82 min.
MS (ESI) m/z=876.30 (M+H)+.

Compound (I-2-4) was synthesized from Compound 72, in a similar way that Compound (I-2-3) was synthesized from Compound 68.
Compound (I-2-4); Method C
LC/MS retention time=1.42 min.
MS (ESI) m/z=550.10 (M+H)+.

Example 17

[Chemical formula 43]

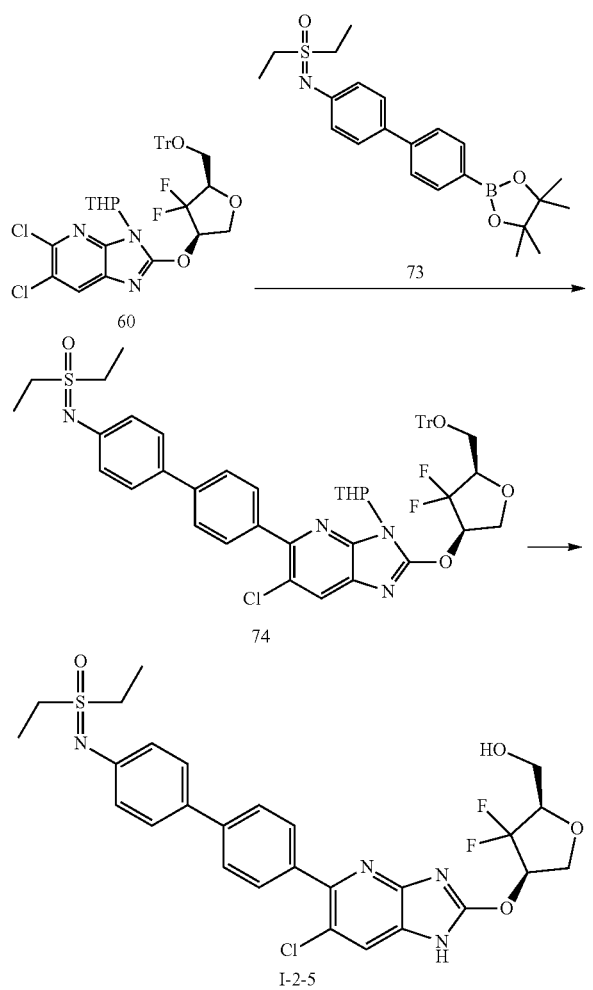

Compound 74 was synthesized from Compound 73, in a similar way that Compound 68 was synthesized from Compound 67.
Compound 74; Method C
LC/MS retention time=3.11 min.
MS (ESI) m/z=903.20 (M+H)+.

Compound (I-2-5) was synthesized from Compound 74, in a similar way that Compound (I-2-3) was synthesized from Compound 68.
Compound (I-2-5); Method C
LC/MS retention time=1.70 min.
MS (ESI) m/z=577.10 (M+H)+.

Example 18

[Chemical formula 44]

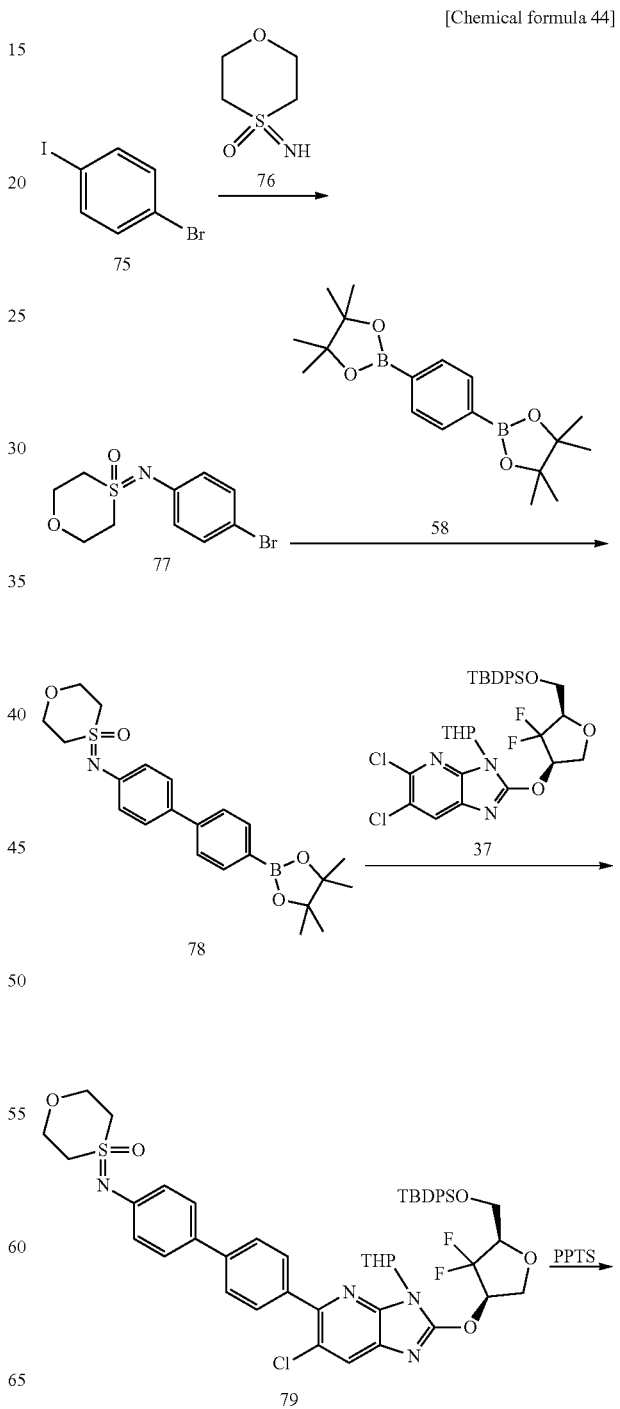

-continued

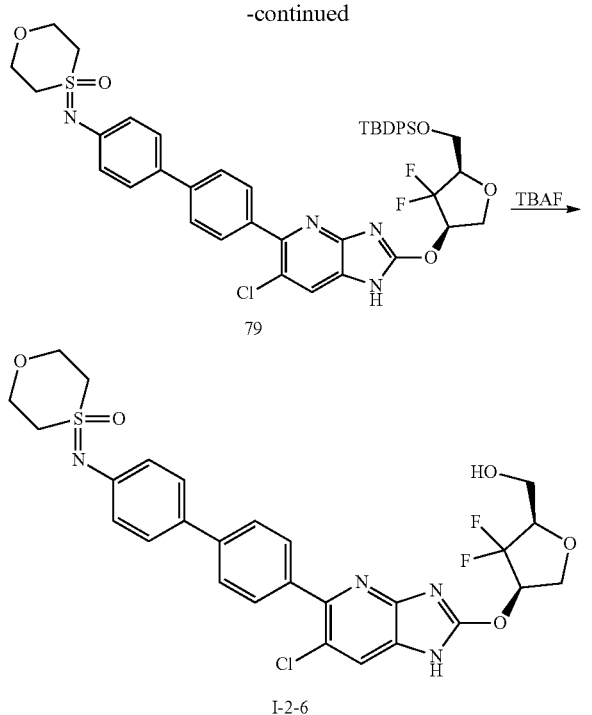

I-2-6

Compound 77 was synthesized from Compound 75, in a similar way that Compound 70 was synthesized from Compound 69.
Compound 77; Method C
LC/MS retention time=1.65 min.
MS (ESI) m/z=289.85 (M+H)+.

Compound 78 was synthesized from Compound 77, in a similar way that Compound 71 was synthesized from Compound 70.
Compound 78; Method C
LC/MS retention time=2.29 min.
MS (ESI) m/z=414.15 (M+H)+.

Compound 79 was synthesized from Compound 78, in a similar way that Compound 72 was synthesized from Compound 71.
Compound 79; Method C
LC/MS retention time=3.22 min.
MS (ESI) m/z=913.40 (M+H)+.

To a mixed solution of ethanol (2 mL) and water (0.5 mL) of Compound 79 (62.9 mg) was added PPTS (34.6 mg, 0.138 mmol), and the mixture was heated under reflux. The reaction mixture was concentrated under reduced pressure, then ethyl acetate and water were added thereto, and a liquid-liquid separation was performed. To a THF (1 mL) solution of the concentrated residue containing Compound 80 obtained by concentrating the organic layer under reduced pressure was added a 1 mol/L TBAF THF solution (69 μL, 0.069 mmol), and the mixture was stirred at room temperature for 1 hour. A 1 mol/L TBAF THF solution (34 μL, 0.034 mmol) was added thereto, and the mixture was stirred at room temperature for 1 hour. Ethyl acetate and water were added to the reaction mixture, and a liquid-liquid separation was performed. The obtained organic layer was concentrated under reduced pressure, and the obtained residue was purified by silica gel column chromatography and the resulting slurry was washed with ethyl acetate-hexane to obtain Compound (I-2-6) (16.4 mg, 40.3%).

Compound (I-2-6); Method C
LC/MS retention time=1.82 min.
MS (ESI) m/z=591.10 (M+H)+.

Example 19

[Chemical formula 45]

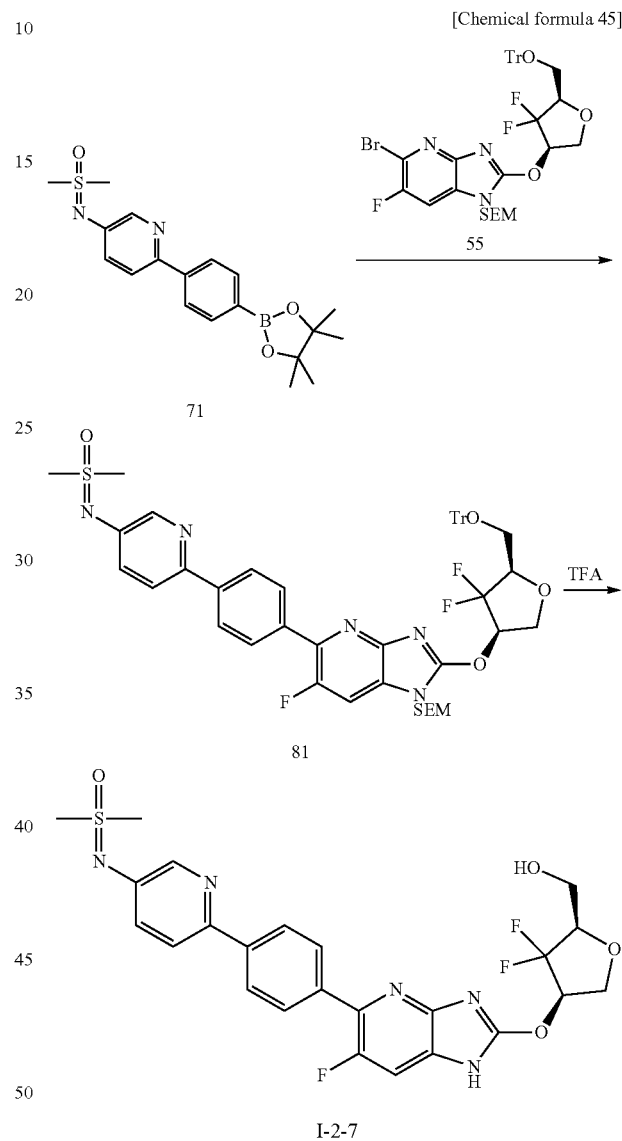

I-2-7

Compound 81 was synthesized from Compound 71, in a similar way that Compound 68 was synthesized from Compound 67.
Compound 81; Method C
LC/MS retention time=3.11 min.
MS (ESI) m/z=903.20 (M+H)+.

Compound (I-2-7) was synthesized from Compound 81, in a similar way that Compound (I-2-1) was synthesized from Compound 62.
Compound (I-2-7); Method C
LC/MS retention time=1.35 min.
MS (ESI) m/z=534.10 (M+H)+.

Example 20

Example 21

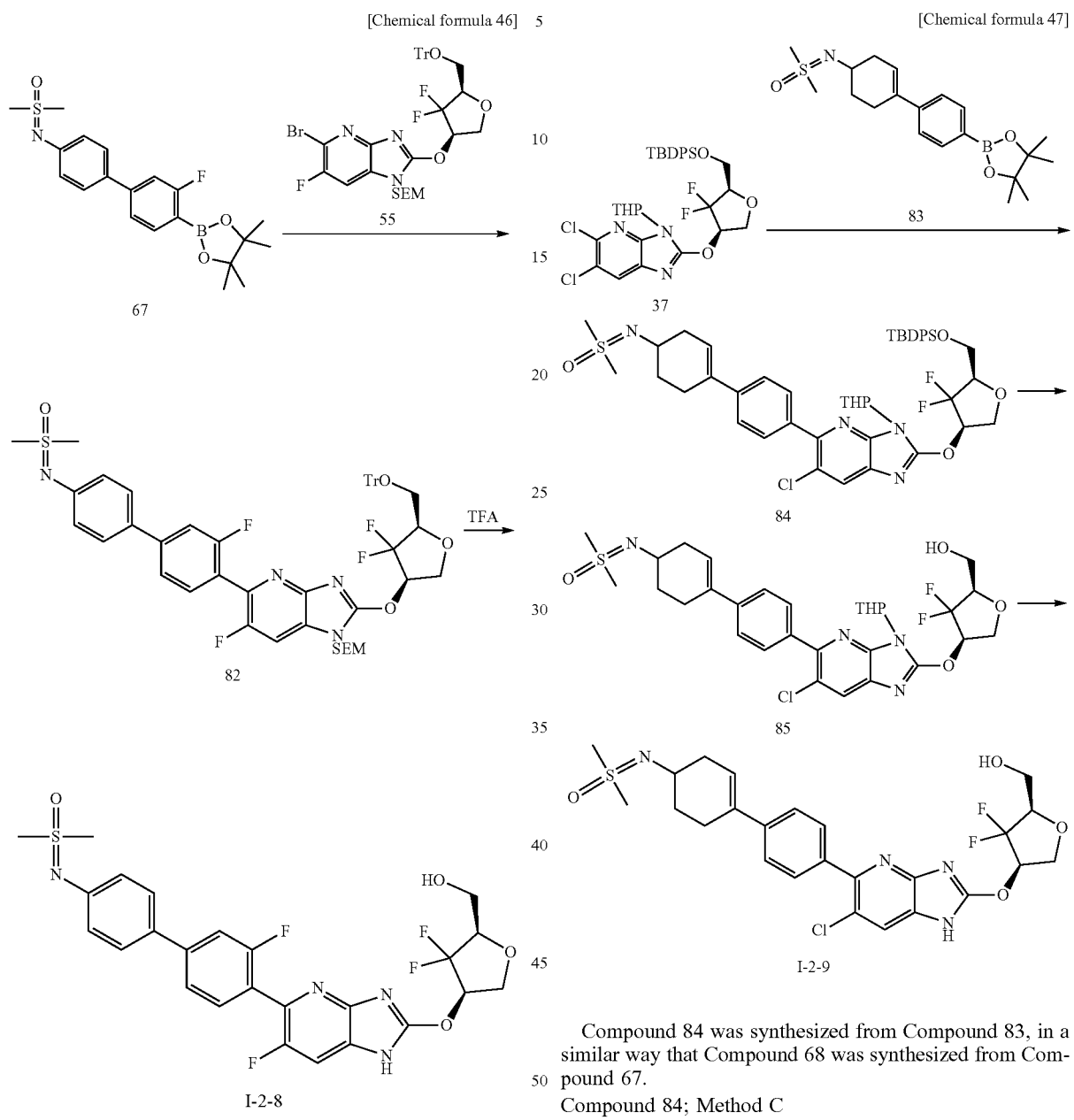

Compound 82 was synthesized from Compound 67, in a similar way that Compound 68 was synthesized from Compound 67.
Compound 82; Method C
LC/MS retention time=3.08 min.
MS (ESI) m/z=923.15 (M+H)+.

Compound (I-2-8) was synthesized from Compound 82, in a similar way that Compound (I-2-1) was synthesized from Compound 62.
Compound (I-2-8); Method C
LC/MS retention time=1.65 min.
MS (ESI) m/z=551.10 (M+H)+.

Compound 84 was synthesized from Compound 83, in a similar way that Compound 68 was synthesized from Compound 67.
Compound 84; Method C
LC/MS retention time=2.92 min.
MS (ESI) m/z=875.25 (M+H)+.

Compound 85 was synthesized from Compound 84, in a similar way that Compound (I-2-6) was synthesized from Compound 80.
Compound 85; Method C
LC/MS retention time=1.77 min.
MS (ESI) m/z=637.15 (M+H)+.

Compound (I-2-9) was synthesized from Compound 85, in a similar way that Compound (I-2-1) was synthesized from Compound 62.
Compound (I-2-9); Method C
LC/MS retention time=1.33 min.
MS (ESI) m/z=553.10 (M+H)+.

Example 22
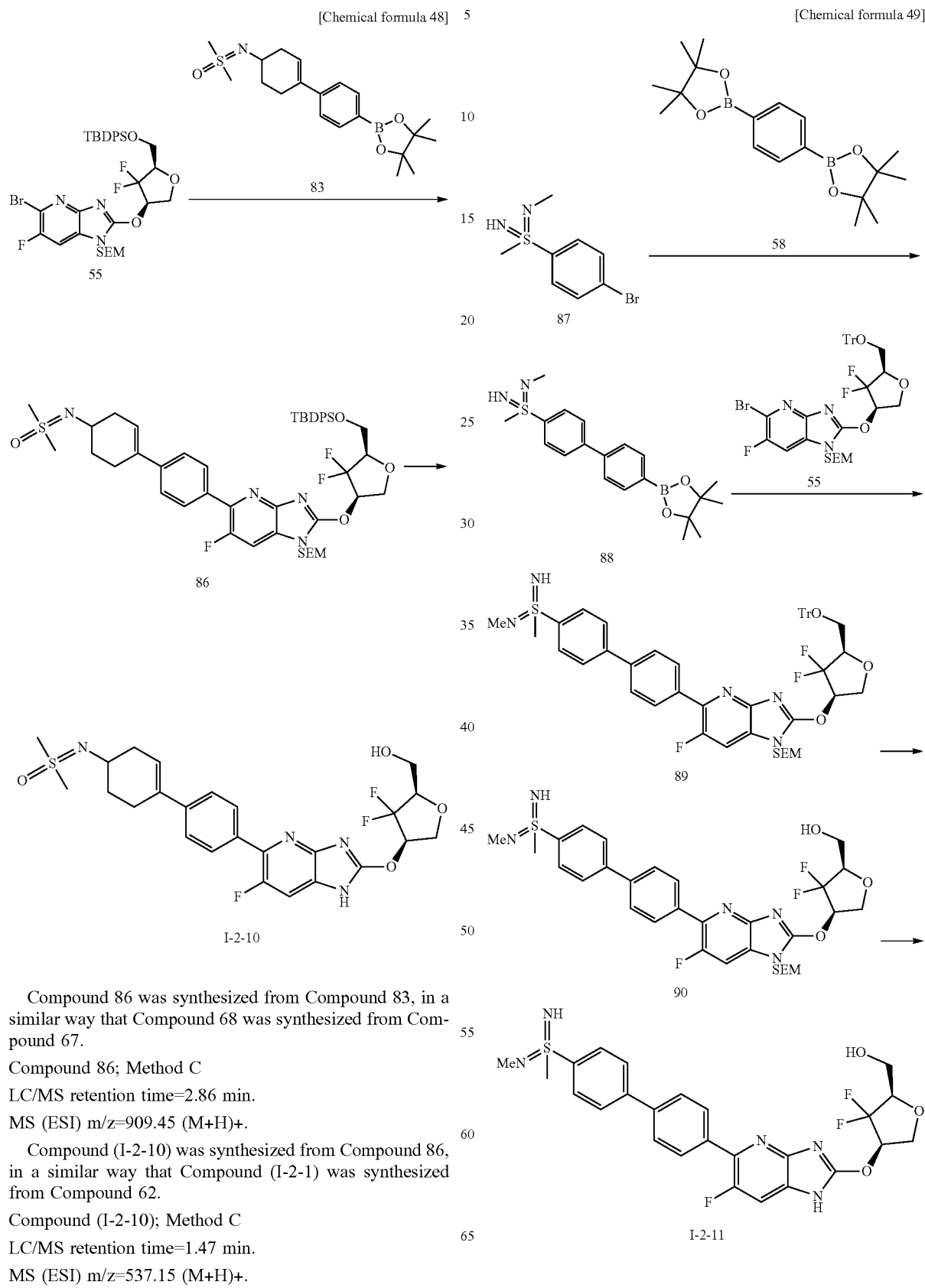
Compound 86 was synthesized from Compound 83, in a similar way that Compound 68 was synthesized from Compound 67.
Compound 86; Method C
LC/MS retention time=2.86 min.
MS (ESI) m/z=909.45 (M+H)+.
Compound (I-2-10) was synthesized from Compound 86, in a similar way that Compound (I-2-1) was synthesized from Compound 62.
Compound (I-2-10); Method C
LC/MS retention time=1.47 min.
MS (ESI) m/z=537.15 (M+H)+.
Example 23

Compound 88 was synthesized from Compound 87, in a similar way that Compound 78 was synthesized from Compound 77.

Compound 88; Method C

LC/MS retention time=1.69 min.

MS (ESI) m/z=371.15 (M+H)+.

Compound 89 was synthesized from Compound 88, in a similar way that Compound 68 was synthesized from Compound 67.

Compound 89; Method C

LC/MS retention time=2.55 min.

MS (ESI) m/z=904.30 (M+H)+.

Compound 90 was synthesized from Compound 89, in a similar way that Compound (I-2-3) was synthesized from Compound 682.

Compound 90; Method C

LC/MS retention time=1.62 min.

MS (ESI) m/z=662.25 (M+H)+.

Compound (I-2-11) was synthesized from Compound 90, in a similar way that Compound (I-2-1) was synthesized from Compound 62.

Compound (I-2-11); Method C

LC/MS retention time=1.42 min.

MS (ESI) m/z=532.10 (M+H)+.

Example 24

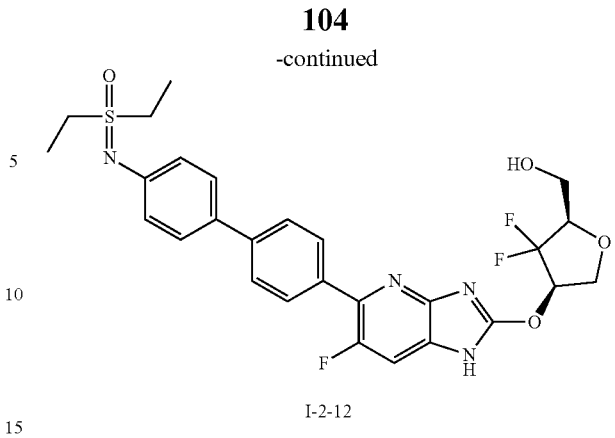

I-2-12

Compound 91 was synthesized from Compound 73, in a similar way that Compound 68 was synthesized from Compound 67.

Compound 91; Method C

LC/MS retention time=3.18 min.

Compound (I-2-12) was synthesized from Compound 91, in a similar way that Compound (I-2-1) was synthesized from Compound 62.

Compound (I-2-12); Method C

LC/MS retention time=1.84 min.

MS (ESI) m/z=561.15 (M+H)+.

Example 25

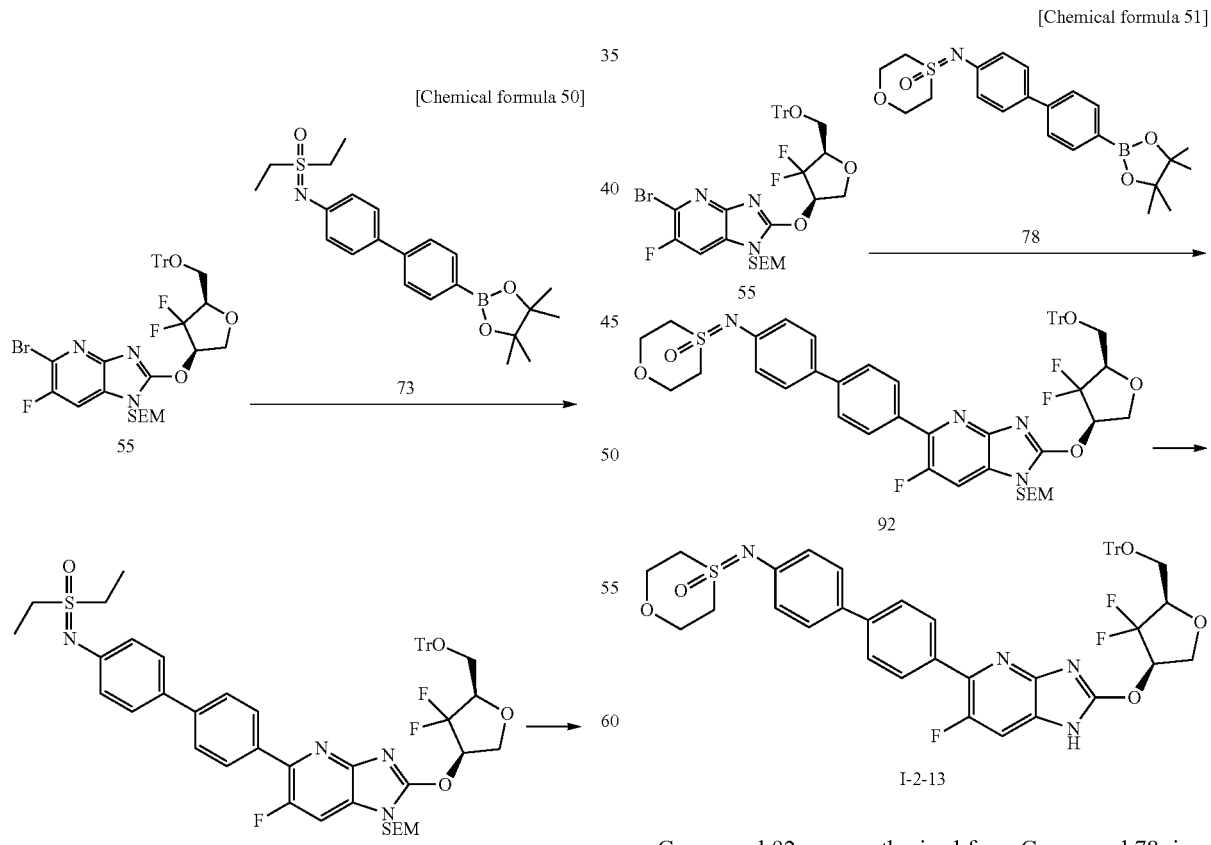

Compound 92 was synthesized from Compound 78, in a similar way that Compound 68 was synthesized from Compound 67.

Compound 92; Method C
LC/MS retention time=3.12 min.
MS (ESI) m/z=947.30 (M+H)+.

Compound (I-2-13) was synthesized from Compound 92, in a similar way that Compound (I-2-1) was synthesized from Compound 62.
Compound (I-2-13); Method C
LC/MS retention time=1.76 min.
MS (ESI) m/z=575.15 (M+H)+.

Example 26

[Chemical formula 52]

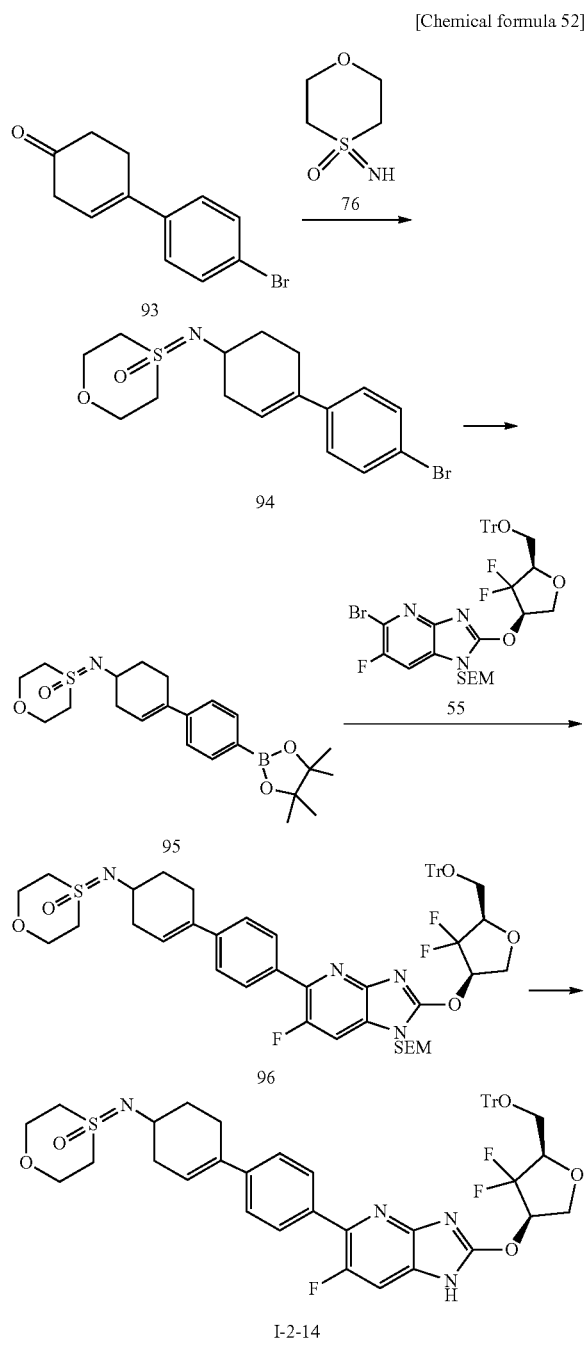

To a mixed solution of methanol (4 mL) and acetic acid (0.4 mL) of Compound 93 (105 mg, 0.418 mmol) and Compound 76 (66.5 mg, 0.418 mmol) was added a picoline-borane complex (44.7 mg, 0.418 mmol), and the mixture was stirred at room temperature. To a residue obtained by concentrating the reaction mixture was added a 2.88 mol/L aqueous solution of hydrochloric acid (2.25 mL, 6.48 mmol), and the mixture was stirred. The mixture was neutralized with a 2 mol/L aqueous sodium carbonate solution (3.7 mL, 7.40 mmol). Similarly, to a mixed solution of methanol (4 mL) and acetic acid (0.4 mL) of Compound 93 (379 mg, 1.51 mmol) and Compound 76 (200 mg, 1.26 mmol) was added α-picoline-borane complex (202 mg, 1.89 mmol), and the mixture was stirred at room temperature. To a residue obtained by concentrating the reaction mixture was added a 2.88 mol/L aqueous solution of hydrochloric acid (6.76 mL, 19.5 mmol), and the mixture was stirred. The mixture was neutralized with a 2 mol/L aqueous sodium carbonate solution (3.7 mL, 7.40 mmol). The two reaction mixtures were mixed with ethyl acetate, then a liquid-liquid separation was performed. The obtained organic layer was concentrated under reduced pressure, and the obtained residue was purified by silica gel column chromatography to obtain Compound 94 (134 mg, 21.6%).

Compound 94; Method C
LC/MS retention time=2.00 min.
MS (ESI) m/z=370.00 (M+H)+.

To a solution of Compound 94 (134 mg, 0.362 mmol and bis(pinacolato)diboron (110 mg, 0.435 mmol) in 1,4-dioxane (2 mL) were added potassium acetate (107 mg, 1.09 mmol) and PdCl$_2$(dppf) (23.6 mg, 0.036 mmol), and the mixture was stirred at 100° C. The obtained reaction mixture was purified by silica gel column chromatography and the resulting slurry was washed with ethyl acetate-hexane to obtain Compound 95 (71.3 mg, 47.2%).

Compound 95; Method C
LC/MS retention time=2.16 min.
MS (ESI) m/z=418.15 (M+H)+.

Compound 96 was synthesized from Compound 95, in a similar way that Compound 68 was synthesized from Compound 67.

Compound 96; Method C
LC/MS retention time=3.09 min.
MS (ESI) m/z=951.35 (M+H)+.

Compound (I-2-14) was synthesized from Compound 96, in a similar way that Compound (I-2-1) was synthesized from Compound 62.

Compound (I-2-14); Method C
LC/MS retention time=1.68 min.
MS (ESI) m/z=579.10 (M+H)+.

Example 27

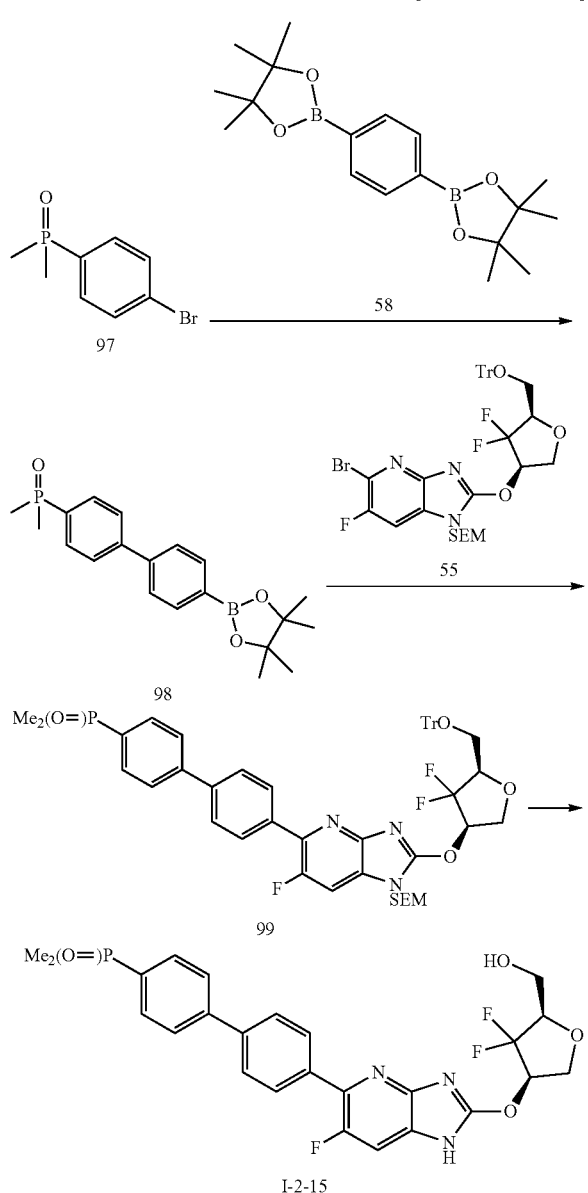

To a solution of Compound 97 (284 mg, 1.22 mmol) and Compound 58 (1.21 g, 3.65 mmol) in 1,4-dioxane (6 mL) were added PdCl$_2$(dtbpf) (159 mg, 0.243 mmol) and a 2 mol/L aqueous solution of potassium carbonate (913 µL, 1.83 mmol), and the mixture was stirred at 100° C. for 2 hours. The obtained reaction mixture was dried over anhydrous sodium sulfate, and concentrated under reduced pressure. The obtained residue was purified by silica gel column chromatography to obtain Compound 98 (302 mg, 69.7%).
Compound 98; Method C
LC/MS retention time=2.07 min.
MS (ESI) m/z=357.15 (M+H)+.

Compound 99 was synthesized from Compound 98, in a similar way that Compound 68 was synthesized from Compound 67.
Compound 99; Method C
LC/MS retention time=3.04 min.
MS (ESI) m/z=890.40 (M+H)+.

Compound (I-2-15) was synthesized from Compound 99, in a similar way that Compound (I-2-1) was synthesized from Compound 62.
Compound (I-2-15); Method C
LC/MS retention time=1.62 min.
MS (ESI) m/z=518.10 (M+H)+.

Evaluation Method of an Activator for
AMP-Activated Protein Kinase (AMPK)

Test Example 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium ß-glycerophosphate and 2 mM dithiothreitol, a human AMPK α1ß1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The resulting liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium 6-glycerophosphate, 2 mM dithiothreitol, 0.4 mM ATP and 3 µM FL-Peptide 7 (manufactured by Caliper Life Sciences, Inc.) was added in equal amount (10 µl in total). The resulting liquid was allowed to react at 25° C. for 2 hours, then 10 µl of 20 mM EDTA was added thereto to stop the reaction.

To detect phosphorylated fluorescent substrates, the reaction mixture was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the obtained substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

Preparation Method of Human AMPK α2ß2γ1

The full length cDNAs of human AMPK ß2 (NM_005399.3) and human AMPK α2 (NM_006252.3) were inserted into the MCS1 and MCS2 of the pETDuet-1 vector to prepare a human AMPK ß2 and human AMPK α2 (6× His tag at the 5' terminus) expressing plasmid. The plasmid was cotransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation method of human CaMKK2 used to impart activity to AMPK An expression vector, in which the full length cDNA of human CAMKK ß (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK 8 from 720 ml of broth.

Evaluation Method of an Activator for
AMP-Activated Protein Kinase (AMPK)

Test Example 2

Human AMPK α2ß2γ1 prepared in *Escherichia coli* was not phosphorylated and did not exhibit activity. Thus, phosphorylation treatment was carried out as pretreatment.

Human AMPK α2ß2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)-N,N,N',N'-tetraacetic acid (EGTA), 5 mM disodium ß-glycerophosphate, 1 mM dithiothreitol and 0.2 mM ATP, and the resulting liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The resulting liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium ß-glycerophosphate, 2 mM dithiothreitol, 0.4 mM ATP and 3 µM FL-Peptide 7 (manufactured by Caliper Life Sciences, Inc.) was added in equal amount (10 µl in total). The resulting liquid was allowed to react at 25° C. for 2 hours, and 10 µl of 20 mM EDTA was added thereto to stop the reaction.

To detect phosphorylated fluorescent substrates, the reaction mixture was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the obtained substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound (I-1-2): EC150=0.93 nM, Emax=556%
Compound (I-1-3): EC150=19 nM, Emax=235%
Compound (I-1-4): EC150=3.8 nM, Emax=364%
Compound (I-1-5): EC150=1.4 nM, Emax=539%
Compound (I-1-6): EC150=7.4 nM, Emax=514%
Compound (I-1-7): EC150=2.1 nM, Emax=504%
Compound (I-1-8): EC150=21 nM, Emax=412%
Compound (I-1-9): EC150=9.5 nM, Emax=389%
Compound (I-1-10): EC150=3.1 nM, Emax=399%
Compound (I-1-11): EC150=1.1 nM, Emax=601%
Compound (I-1-12): EC150=2.4 nM, Emax=649%
Compound (I-2-1): EC150=1.9 nM, Emax=617%
Compound (I-2-2): EC150=3.1 nM, Emax=604%
Compound (I-2-3): EC150=4.2 nM, Emax=609%
Compound (I-2-4): EC150=9.7 nM, Emax=493%
Compound (I-2-5): EC150=6.2 nM, Emax=575%
Compound (I-2-6): EC150=3.0 nM, Emax=578%
Compound (I-2-7): EC150=3.1 nM, Emax=445%
Compound (I-2-8): EC150=0.75 nM, Emax=619%
Compound (I-2-9): EC150=1.3 nM, Emax=652%
Compound (I-2-10): EC150=2.1 nM, Emax=604%
Compound (I-2-11): EC150=1.2 nM, Emax=649%
Compound (I-2-12): EC150=0.54 nM, Emax=595%
Compound (I-2-13): EC150=2.3 nM, Emax=517%
Compound (I-2-14): EC150=1.0 nM, Emax=570%
Compound (I-2-15): EC150=0.67 nM, Emax=583%

The compounds of the present invention have an excellent activating effect on an AMPK α1 trimer and/or an AMPK α2 trimer.

Usefulness as a medicament can be examined by the following tests, etc.

CYP3A4 Fluorescent MBI Test

The CYP3A4 fluorescent MBI test is a test of evaluating Mechanism based inhibition (MBI) ability from enhancement by a metabolism reaction for CYP3A4 inhibition of the compound of the present invention. CYP3A4 inhibition was evaluated as an index 1-hydroxylation reaction of midazolam (MDZ) using pooled human hepatic microsomes.

The reaction conditions were as follows: substrate, 10 µmol/L MDZ; pre-reaction time, 0 or 30 minutes; reaction time, 2 minutes; reaction temperature, 37° C.; pooled human hepatic microsomes, at pre-reaction 0.5 mg/mL, at reaction 0.05 mg/mL (at 10-fold dilution); concentration of the compound of the present invention at pre-reaction, 1, 5, 10, 20 µmol/L (four points).

Pooled human hepatic microsomes in a K-Pi buffer (pH 7.4) and a solution of the compound of the present invention as a pre-reaction mixture were added to a 96-well plate at the composition of the pre-reaction, a part of it was transferred to another a 96-well plate at the composition of the pre-reaction, a part of it was transferred to another 96-well plate so that it was 1/10 diluted with a substrate and a K-Pi buffer, NADPH as a coenzyme was added to initiate a reaction as an index (without pre-reaction) and, after a predetermined time of a reaction, a methanol/acetonitrile=1/1 (V/V) solution was added to stop the reaction. In addition, NADPH was added to a remaining pre-reaction mixture to initiate a pre-reaction (with pre-reaction) and, after a predetermined time of a pre-reaction, a part was transferred to another plate so that it was 1/10 diluted with a substrate and a K-Pi buffer to initiate a reaction as an index. After a predetermined time of a reaction, a methanol/acetonitrile=1/1 (V/V) solution was added to stop the reaction. The plate on which each index reaction had been performed was centrifuged at 3000 rpm for 15 minutes, and then midazolam 1-hydroxylation in the centrifuge supernatant was quantified by LC/MS/MS.

Addition of only DMSO being a solvent dissolving the compound of the present invention to a reaction system was adopted as a control (100%), remaining activity (%) was calculated at each concentration of the compound of the present invention added, and IC was calculated by reverse presumption by a logistic model using a concentration and an inhibition rate. "IC value at start of pre-reaction/IC value at 30 minutes after start of pre-reaction" was defined as Shifted IC value. When Shifted IC was 1.5 or more, this was defined as (+), and when Shifted IC was 1.0 or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenadine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a coenzyme was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the centrifuge supernatant was quantified by a fluorescent multilabel counter, and tolbutamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution, and $IC_{50}$ was calculated by reverse presumption by a logistic model using a concentration and an inhibition rate.

FAT Test

Each 20 µL of freeze-stored *Salmonella typhimurium* (strains TA98 and TA100) is inoculated in 10 mL of liquid nutrient medium (2.5% Oxoid nutrient broth No. 2), and the cultures are preincubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 110 mL of Exposure medium (Micro F buffer containing Biotin: 8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (a mixed solution of 498 µL of the test bacterial solution and 90 µL of the S9 mix in the case with metabolic activation conditions) is mixed with each 12 L of the following solution: DMSO solution of the test substance (eight dose levels from maximum dose 50 mg/mL at 2-fold ratio); DMSO as negative control; 50 µg/mL of 4-nitroquinoline-1-oxide DMSO solution as positive control for strain TA98 without metabolic activation conditions; 0.25 µg/mL of 2-(2-furyl)-3-(5-nitro-2-furyl)acrylamide DMSO solution as positive control for strain TA100 without metabolic activation conditions; 40 µg/mL of 2-aminoanthracene DMSO solution as positive control for strain TA98 with metabolic activation conditions; or 20 µg/mL of 2-aminoanthracene DMSO solution as positive control for strain TA100 with metabolic activation conditions, and the mixture is incubated at 37° C. under shaking for 90 minutes. 460 µL of the culture exposed to the test substance is mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into 48 wells per dose in the microplates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. Thus, the number of the yellow wells among the 48 total wells per dose is counted to evaluate the mutagenicity by comparing with the negative control group.

Solubility Test

The solubility of a compound was determined under a condition in which 1% DMSO was added. A 10 mM compound solution was prepared using DMSO, and then 6 µL of the compound solution was added to 594 µL of artificial intestinal juice in pH 6.8 (to 250 mL of a 0.2 mol/L potassium dihydrogen phosphate reagent solution were added 118 mL of a 0.2 mol/L NaOH reagent solution and water to provide a final volume of 1000 mL). After standing at 25° C. for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, an test compound was reacted for a constant time, a remaining rate was calculated by comparing a reacted sample and an unreacted sample, thereby, a degree of metabolism in hepatic was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human hepatic microsomes. After the reaction, 50 µL of the reaction mixture was added to 100 µL of a methanol/acetonitrile=1/1 (v/v) solution, and the mixture was mixed and centrifuged at 3000 rpm for 15 minutes. The test compound in the centrifuge supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier $K^+$ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2*2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Powder Solubility Test

Appropriate amounts of the test substances are put into appropriate containers. To the respective containers are added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL). In the case that the test liquid is dissolved after the addition of the test fluid, the bulk powder is added as appropriate. The containers are sealed, and shaken for 1 hour at 37° C. The mixtures are filtered, and 100 μL of methanol is added to each of the filtrate (100 μL) so that the filtrates are two-fold diluted. The dilution ratio is changed if necessary. After confirmation of no bubbles and precipitates, the containers are sealed and shaken. Quantification is performed by HPLC with an absolute calibration method.

BA Test

Materials and Methods for Studies on Oral Absorption (1) Animals: mice or rats
(2) Animal husbandry: Mice and rats had free access to solid food and sterilized bottled tap water.
(3) Setting of dose and group compositions: orally or intravenously administered at a predetermined dose; Group compositions were as shown below. (Dose depends on the compound)
   Oral: 1 to 30 mg/kg (n=2 to 3)
   Intravenous: 0.5 to 10 mg/kg (n=2 to 3)
(4) Preparation of administration formulation: for oral administration, in a solution or a suspension state; for intravenous administration, in a solubilized state.
(5) Dosing procedure: In oral administration study, the test substance was forcibly administered to the stomach by using a gavage tube. In intravenous administration study, the test substance was administered via tail vein using a syringe with a needle.
(6) Evaluation items: Blood was collected at each time point, and plasma concentration of the test substance was determined by LC/MS/MS.
(7) Data analysis: Regarding the transition of the plasma concentration, area under the plasma concentration-time curve (AUC) was calculated by means of WinNonlin® program, respectively. Bioavailability (BA) was calculated from AUCs of the oral administration group and intravenous administration group.

Formulation Examples are shown below.

Formulation Example 1: Tablets

The compound of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compound of the present invention, lactose and calcium stearate are mixed uniformly to obtain powder medicines in the form of powder or fine granules. The powder medicines are filled into capsule containers to give capsules.

Formulation Example 3: Granules

The compound of the present invention, lactose and calcium stearate are mixed uniformly, and the mixture is compressed and molded. Then, it is crushed, granulated and sieved to give a suitable size of granules.

Formulation Example 4: Orally Disintegrating Tablets

The compound of the present invention and crystalline cellulose are mixed and granulated, then tableted to give orally disintegrating tablets.

Formulation Example 5: Dry Syrups

The compound of the present invention and lactose are mixed, crushed, granulated and sieved to give a suitable size of dry syrups.

Formulation Example 6: Injections

The compound of the present invention and phosphate buffer are mixed to give injections.

Formulation Example 7: Infusions

The compound of the present invention and phosphate buffer are mixed to give injections.

Formulation Example 8: Inhalations

The compound of the present invention and lactose are mixed and crushed finely to give inhalations.

Formulation Example 9: Ointments

The compound of the present invention and petrolatum are mixed to give ointments.

Formulation Example 10: Patches

The compound of the present invention and base such as adhesive plaster or the like are mixed to give patches.

INDUSTRIAL APPLICABILITY

As is apparent from the above test examples, the compounds of the present invention show an AMPK activating effect. Therefore, the compounds of the present invention are very useful as a therapeutic agent for type I diabetes, type II diabetes, hyperglycemia, metabolic syndrome, obesity, hypercholesterolemia and hypertension.

The invention claimed is:

1. A compound represented by the formula (I):

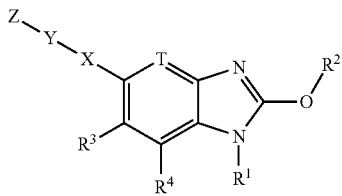

or its pharmaceutically acceptable salt, wherein, $R^1$ is hydrogen, or substituted or unsubstituted alkyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

T is —CR$^5$= or —N=;

X is a single bond, substituted or unsubstituted aryl, substituted or unsubstituted heteroaryl, substituted or unsubstituted cycloalkyl, substituted or unsubstituted cycloalkenyl, or substituted or unsubstituted heterocyclyl;

Y is substituted or unsubstituted aryl, substituted or unsubstituted heteroaryl, substituted or unsubstituted cycloalkyl, substituted or unsubstituted cycloalkenyl, or substituted or unsubstituted heterocyclyl;

Z is $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^{S''})-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^NR^{N'}N)(O=)S=N-R^{2f}-$, $(R^{N''})N=S(=O)(NR^NR^{N'})-$, $(R^{N''})N=S(=O)(NR^NR^{N'})-R^{2f}-$, $R^{P1}R^{P2}(O=)P-$,

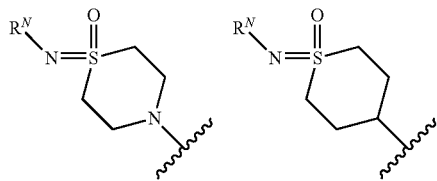

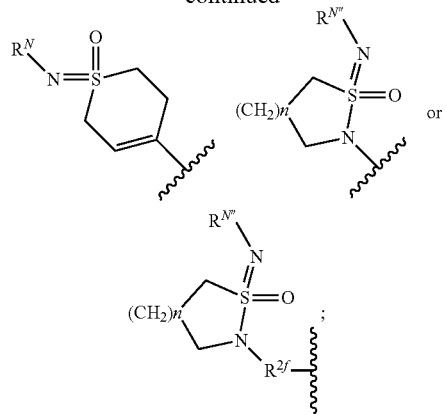

n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{S''}$ is hydrogen, substituted or unsubstituted alkyl, substituted or unsubstituted cycloalkyl, substituted or unsubstituted heterocyclyl, substituted or unsubstituted aryl, or substituted or unsubstituted heteroaryl;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

two $(R^N)N=$ bound to the same sulfur atom may form a substituted or unsubstituted ring together with the sulfur atom when Z is $((R^N)N=)_2S(R^{S''})-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ and $R^{N'}$ bound to the same nitrogen atom may form a substituted or unsubstituted ring together with the nitrogen atom;

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{P1}$ and $R^{P2}$ are each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^3$, $R^4$ and $R^5$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that, when $R^2$ is

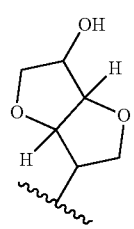

and T is —N=, $R^3$ is fluoro, cyano, substituted or unsubstituted alkyl, or substituted or unsubstituted alkyloxy; and compounds shown below are excluded

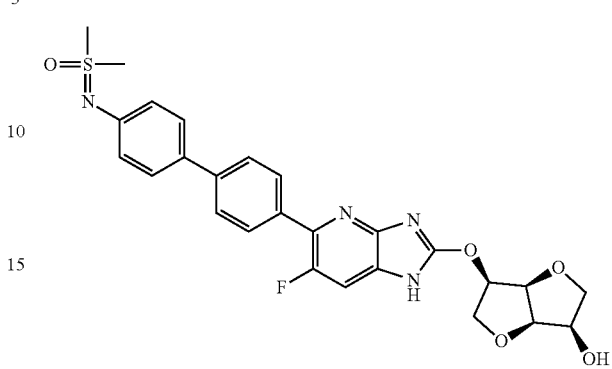

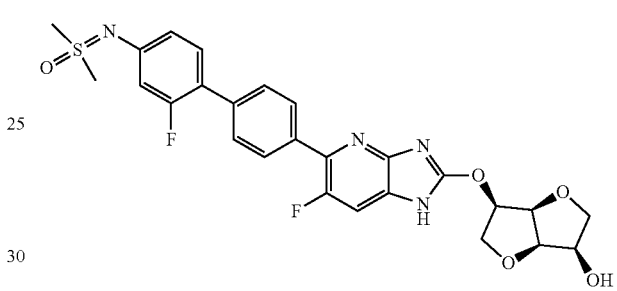

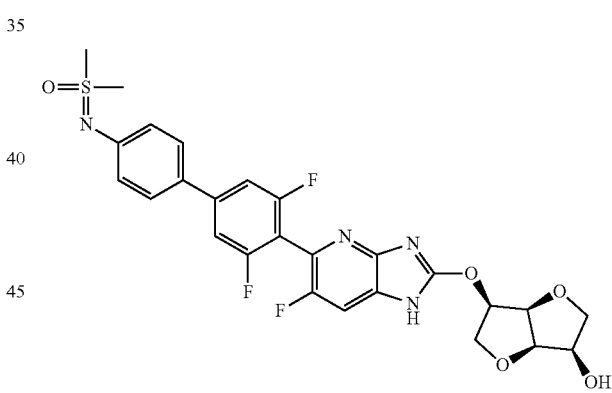

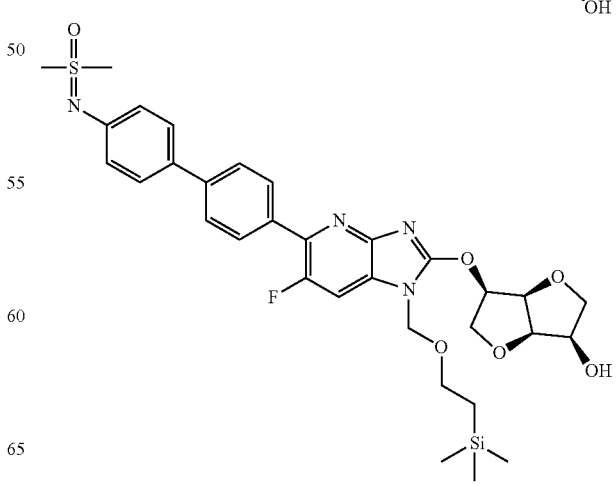

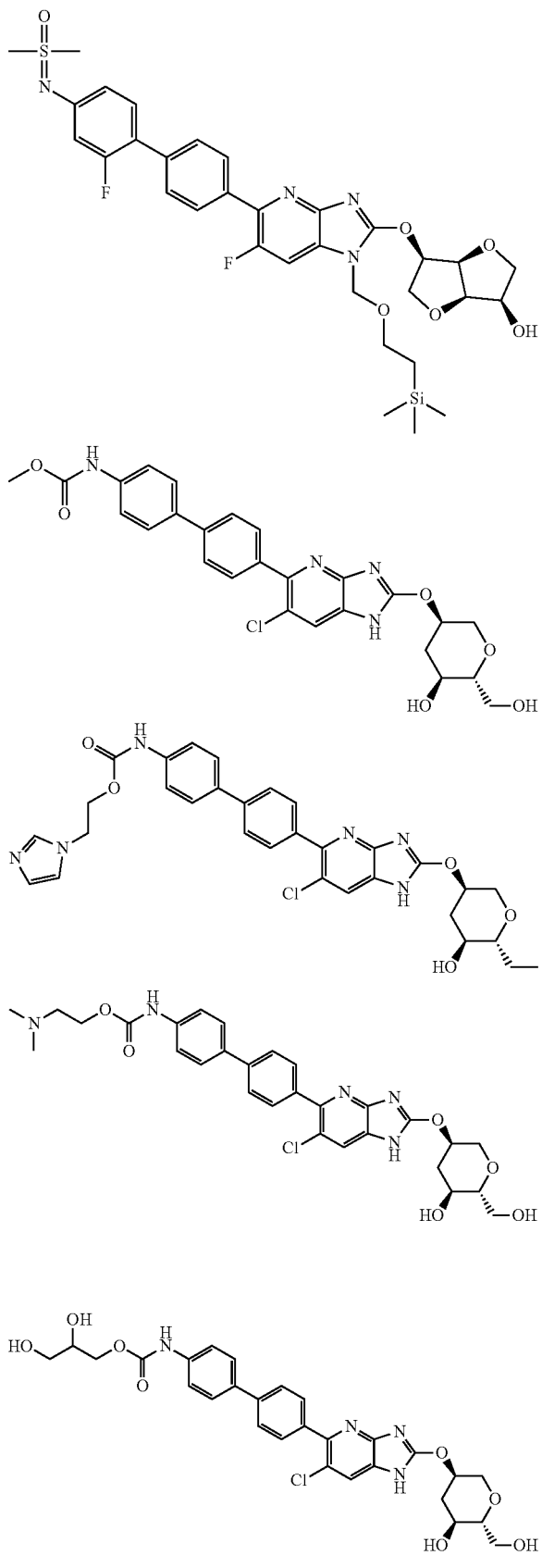

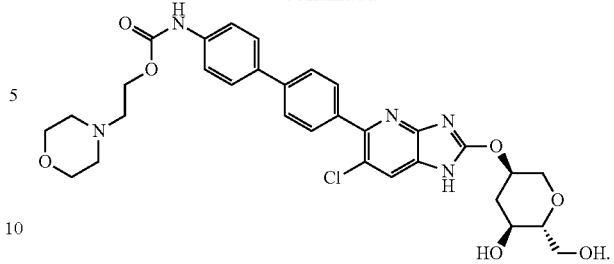

and

2. The compound according to claim 1 or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

3. The compound according to claim 2 or its pharmaceutically acceptable salt, wherein $R^2$ is substituted or unsubstituted cycloalkyl, or substituted or unsubstituted heterocyclyl.

4. The compound according to claim 2 or its pharmaceutically acceptable salt, wherein $R^2$ is aryl, heteroaryl, cycloalkyl, cycloalkenyl or heterocyclyl substituted with at least one group selected from halogen, —$PO(OH)_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

5. The compound according to claim 4 or its pharmaceutically acceptable salt, wherein $R^2$ is cycloalkyl or heterocyclyl substituted with at least one group selected from halogen, —$PO(OH)_2$, substituted or unsubstituted heteroaryl, substituted or unsubstituted heterocyclyl, substituted or unsubstituted alkylthio, substituted or unsubstituted carbamoyl, substituted or unsubstituted sulfamoyl and substituted or unsubstituted amino, and further optionally substituted with hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

6. The compound according to claim 2 or its pharmaceutically acceptable salt, wherein $R^2$ is aryl, heteroaryl, cycloalkyl, cycloalkenyl or heterocyclyl substituted with at least one halogen,
and further optionally substituted with —$PO(OH)_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

7. The compound according to claim 6 or its pharmaceutically acceptable salt, wherein $R^2$ is cycloalkyl or heterocyclyl substituted with at least one halogen, and further optionally substituted with —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, substituted or unsubstituted amino, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl.

8. The compound according to claim 5 or its pharmaceutically acceptable salt,
wherein R$^2$ is

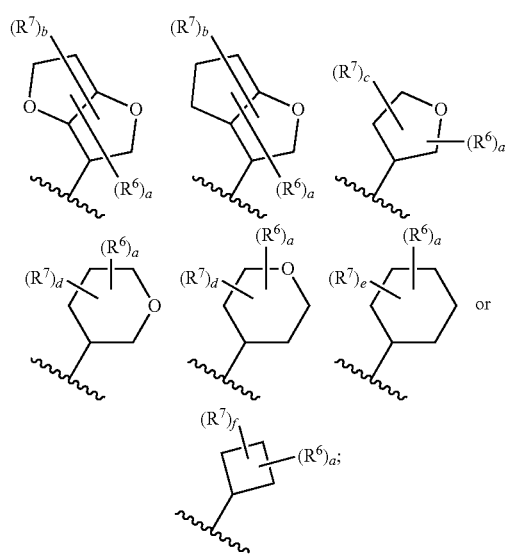

wherein R$^6$ is each independently halogen, —PO(OH)$_2$, substituted or unsubstituted heteroaryl, substituted or unsubstituted heterocyclyl, substituted or unsubstituted alkylthio, substituted or unsubstituted carbamoyl, substituted or unsubstituted sulfamoyl, or substituted or unsubstituted amino;
a is an integer from 1 to 3;
R$^7$ is each independently hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylsulfonyl, or substituted or unsubstituted acyl;
b is an integer from 0 to 8;
c is an integer from 0 to 6;
d is an integer from 0 to 8;
e is an integer from 0 to 10;
f is an integer from 0 to 6.

9. The compound according to claim 8 or its pharmaceutically acceptable salt, wherein R$^2$ is

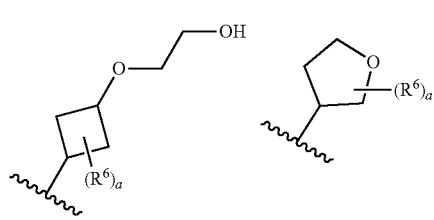

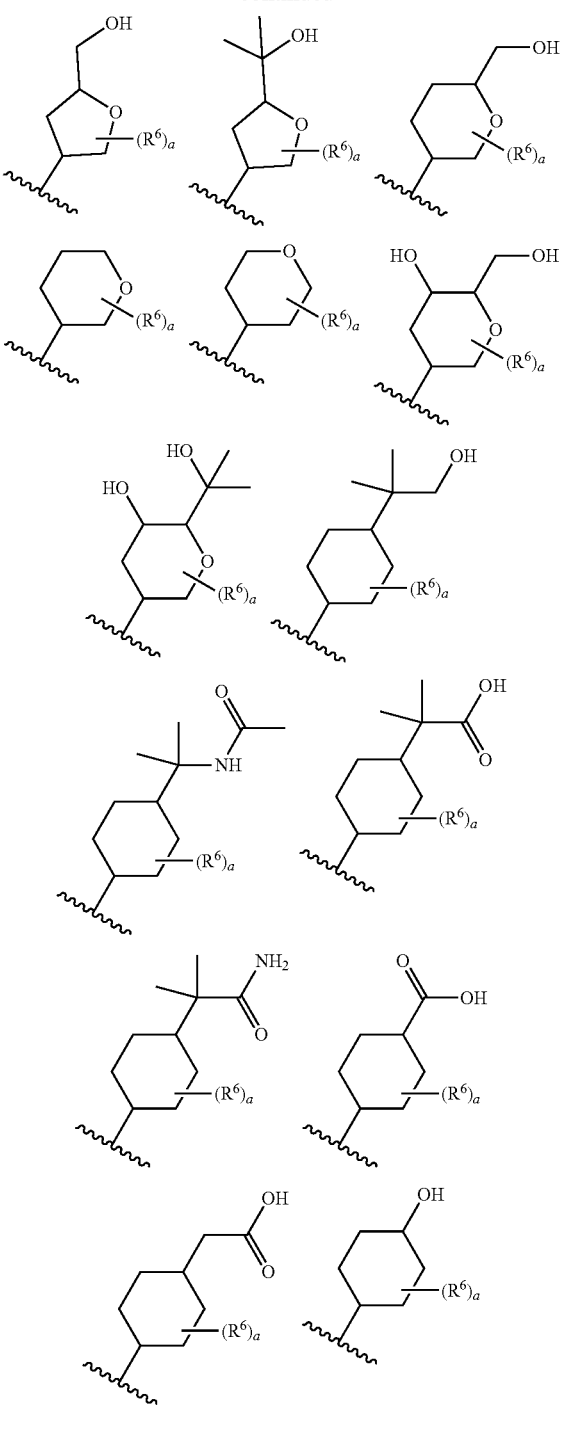

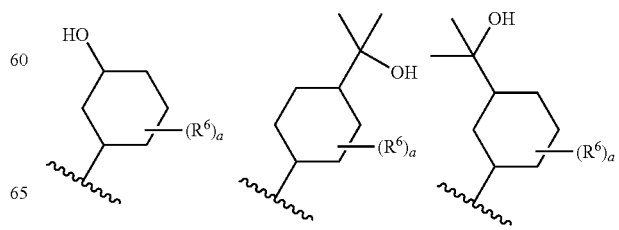

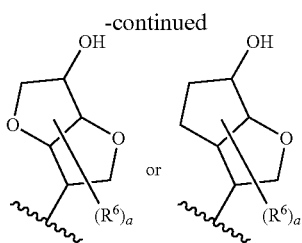

wherein R⁶ and a are as defined in claim 8.

10. The compound according to claim 8 or its pharmaceutically acceptable salt, wherein a is 1 or 2; and R⁶ is each independently halogen.

11. The compound according to claim 9 or its pharmaceutically acceptable salt, wherein a is 1 or 2; and R⁶ is each independently halogen.

12. The compound according to claim 1 or its pharmaceutically acceptable salt, wherein R³ is halogen, cyano, substituted or unsubstituted alkyl, or substituted or unsubstituted alkyloxy.

13. The compound according to claim 12 or its pharmaceutically acceptable salt, wherein R³ is halogen.

14. The compound according to claim 1 or its pharmaceutically acceptable salt, wherein R² is substituted or unsubstituted cycloalkyl, or substituted or unsubstituted heterocyclyl; and R³ is fluoro, cyano, substituted or unsubstituted alkyl, or substituted or unsubstituted alkyloxy.

15. The compound according to claim 14 or its pharmaceutically acceptable salt, wherein R² is

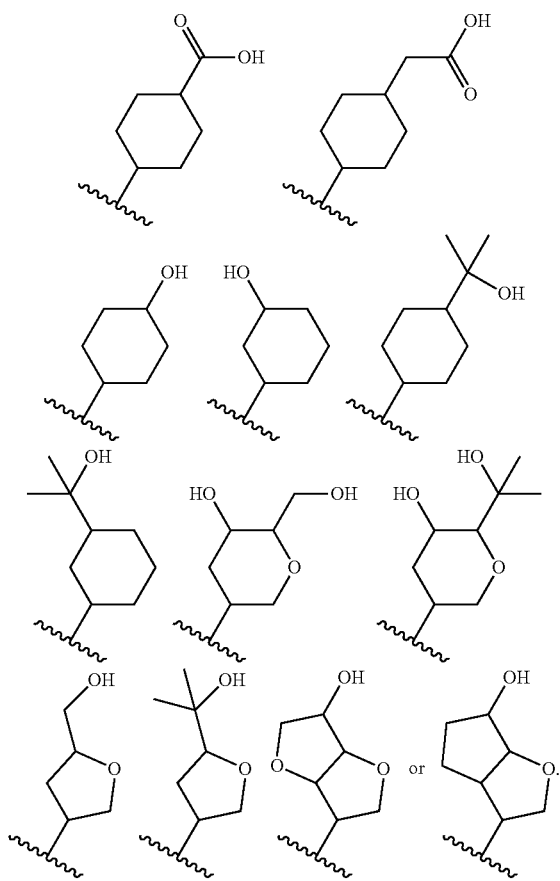

16. The compound according to claim 14, or its pharmaceutically acceptable salt, wherein R³ is fluoro.

17. The compound according to claim 1 or its pharmaceutically acceptable salt, wherein X is a single bond, substituted or unsubstituted aryl, substituted or unsubstituted heteroaryl, or substituted or unsubstituted heterocyclyl.

18. The compound according to claim 1 or its pharmaceutically acceptable salt, wherein Y is substituted or unsubstituted aryl, substituted or unsubstituted cycloalkenyl, or substituted or unsubstituted heterocyclyl.

19. The compound according to claim 1 or its pharmaceutically acceptable salt, wherein Z is $R^S R^{S'}(O=)S=N-$, $(R^N)N=S(=O)(R^S)-$, $R^O-C(=O)-N(R^N)-$, or $R^S(R^N R^{N'}N)(O=)S=N-$.

20. The compound according to claim 1 or its pharmaceutically acceptable salt, wherein T is $-N=$.

21. The compound according to claim 1 or its pharmaceutically acceptable salt, wherein R¹ is hydrogen.

22. The compound according to claim 1 or its pharmaceutically acceptable salt, wherein R⁴ is hydrogen.

23. The compound according to claim 1 or its pharmaceutically acceptable salt, wherein the compound is

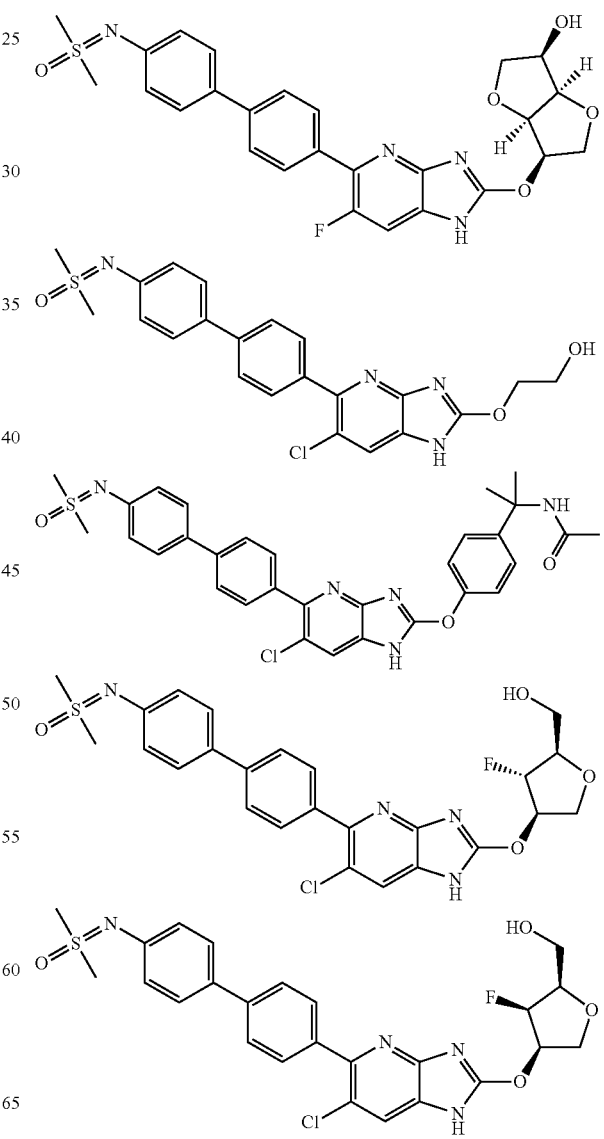

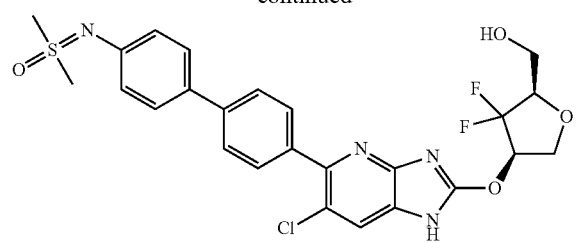
24. The compound according to claim 1 or its pharmaceutically acceptable salt, wherein the compound is 127
-continued

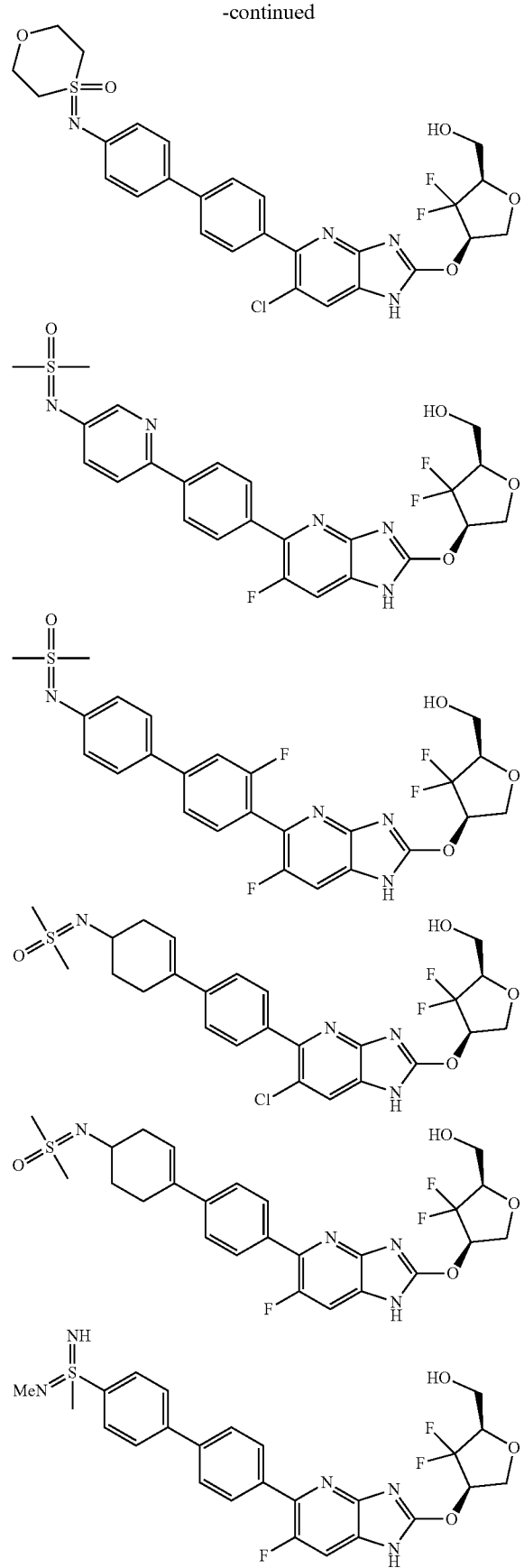

128
-continued

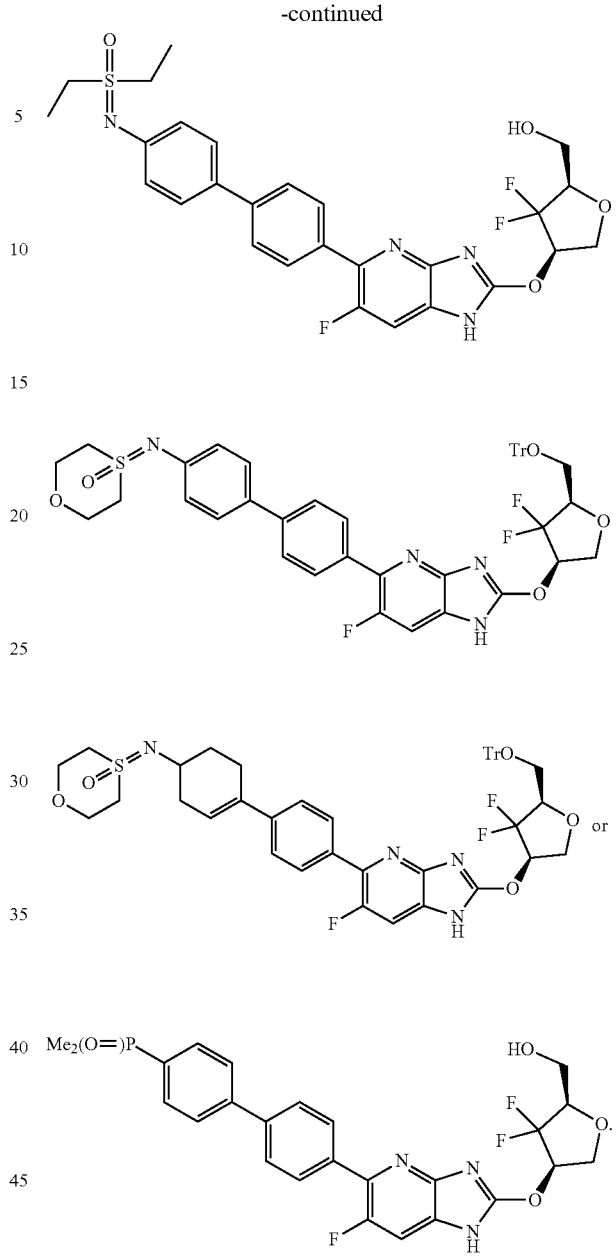

25. A pharmaceutical composition comprising the compound according to claim 1 or its pharmaceutically acceptable salt and a pharmaceutically acceptable additive.

26. The pharmaceutical composition according to claim 25, which has an activating effect on adenosine monophosphate-activated protein kinase.

27. The pharmaceutical composition according to claim 25, for the treatment of diabetes.

28. A method for treating diabetes, comprising administering an effective amount of the compound according to claim 1, or its pharmaceutically acceptable salt to a patient in need thereof.

29. The compound according to claim 1, or its pharmaceutically acceptable salt, for the treatment of diabetes.

* * * * *